United States Patent
Lieb et al.

(10) Patent No.: US 6,511,942 B1
(45) Date of Patent: Jan. 28, 2003

(54) 2,4,5-TRISUBSTITUTED PHENYLKETO-ENOLS FOR USE AS PESTICIDES AND HERBICIDES

(75) Inventors: Folker Lieb, Leverkusen (DE); Hermann Hagemann, Leverkusen (DE); Arno Widdig, Odenthal (DE); Michael Ruther, Monheim (DE); Reiner Fischer, Monheim (DE); Thomas Bretschneider, Lohmar (DE); Christoph Erdelen, Leichlingen (DE); Ulrike Wachendorff-Neumann, Neuwied (DE); Hans-Joachim Santel, Leverkusen (DE); Markus Dollinger, Leverkusen (DE); Alan Graff, Köln (DE); Norbert Mencke, Leverkusen (DE); Andreas Turberg, Erkrath (DE); Peter Dahmen, Neuss (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/496,616

(22) Filed: Feb. 2, 2000

Related U.S. Application Data

(62) Division of application No. 08/983,028, filed as application No. PCT/EP96/02606 on Jun. 17, 1996, now Pat. No. 6,110,872.

(30) Foreign Application Priority Data

Jun. 28, 1995 (DE) .......................... 195 23 471
Jan. 25, 1996 (DE) .......................... 196 02 524

(51) Int. Cl.[7] ............... A01N 43/08; A61K 31/34; C07D 307/02

(52) U.S. Cl. ............... 504/299; 514/473; 549/477

(58) Field of Search .................. 549/477; 504/299; 514/473

(56) References Cited

U.S. PATENT DOCUMENTS 5,094,681 A * 3/1992 Kramer et al. ............... 71/88
5,262,383 A * 11/1993 Fischer et al. ............... 504/195
5,462,913 A   10/1995 Fischer et al. ............... 504/138

(List continued on next page.)

FOREIGN PATENT DOCUMENTS

| | | |
|---|---|---|
| DE | 44 10 410 | 9/1995 |
| EP | 0 596 298 | 5/1994 |
| EP | 0 613 885 | 9/1994 |
| EP | 0 647 637 | 4/1995 |
| WO | WO 95/01358 | 1/1995 |
| WO | WO 95/01971 | 1/1995 |
| WO | WO 95/14013 | 5/1995 |
| WO | WO 95/20572 | 8/1995 |
| WO | WO 95/26954 | 10/1995 |

Primary Examiner—Bruck Kifle
(74) Attorney, Agent, or Firm—Norris McLaughlin & Marcus

(57) ABSTRACT

The invention relates to new phenyl-substituted cyclic ketoenols of the formula (I)

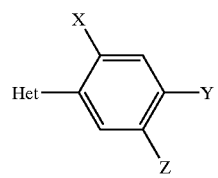

(I)

in which

Het represents one of the groups

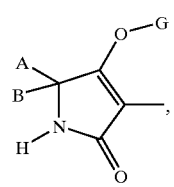

(1)

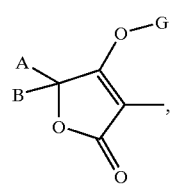

(2)

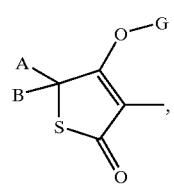

(3)

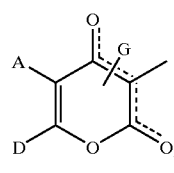

(4)

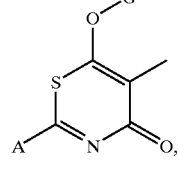

(5)

wherein A, B, D, G, X, Y and Z have the meaning given in the description, several processes and intermediate products for their preparation and their use as pest control agents and herbicides.

7 Claims, No Drawings

U.S. PATENT DOCUMENTS

| | | | |
|---|---|---|---|
| 5,504,057 A | 4/1996 | Fischer et al. | 504/283 |
| 5,589,469 A | 12/1996 | Fischer et al. | 514/91 |
| 5,602,078 A | 2/1997 | Fischer et al. | 504/283 |
| 5,616,536 A | 4/1997 | Fischer et al. | 504/225 |
| 5,622,917 A | 4/1997 | Fischer et al. | 504/283 |
| 5,677,449 A | 10/1997 | Fischer et al. | 544/165 |
| 5,683,965 A * | 11/1997 | Bachmann et al. | 504/238 |

* cited by examiner

2,4,5-TRISUBSTITUTED PHENYLKETO-ENOLS FOR USE AS PESTICIDES AND HERBICIDES

This application is a divisional of application Ser. No. 08/983,028, filed on Dec. 22, 1997 (now U.S. Pat. No. 6,110,872, which is a 371 of PCT/EP96/02606, filed on Jun. 17, 1996.)

The invention relates to new phenyl-substituted cyclic ketoenols, several processes and intermediate products for their preparation and their use as pest control agents and herbicides.

It has already been disclosed that certain phenyl-substituted cyclic ketoenols are active as insecticides, acaricides and/or herbicides.

Pharmaceutical properties have already been described for 3-acyl-pyrrolidine-2,4-diones (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). No biological activity has been described for these compounds.

EP-A-0 262 399 and GB-A-2 266 888 disclose compounds of similar structure (3-aryl-pyrrolidine-2,4-diones), of which, however, no herbicidal, insecticidal or acaricidal action has been disclosed. Known compounds which have a herbicidal, insecticidal or acaricidal action are unsubstituted, bicyclic 3-aryl-pyrrolidine-2,4-dione derivatives (EP-A-355 599 and EP-A-415 211) and substituted monocyclic 3-aryl-pyrrolidine-2,4-dione derivatives (EP-A-377 893 and EP-A-442 077).

Compounds which are furthermore known are polycyclic 3-arylpyrrolidine-2,4-dione derivatives (EP-A-442 073) and 1H-arylpyrrolidine-dione derivatives (EP-A-456 063, EP-A-521 334, EP-A-596 298, EP-A-613 884, EP-A-613 885, DE 44 40 594, WO 94/01 997 and WO 95/01 358).

It is known that certain substituted $\Delta^3$-dihydrofuran-2-one derivatives have herbicidal properties (cf. DE-A-4 014 420). The synthesis of the tetronic acid derivatives used as starting compounds (such as, for example, 3-(2-methyl-phenyl)-4-hydroxy-5-(4-fluorophenyl)-$\Delta^3$-dihydrofuran-2-one) is likewise described in DE-A-4 014 420. Compounds of similar structure, without an insecticidal and/or acaricidal activity being mentioned, are known from the publication Campbell et al., J. Chem. Soc., Perkin Trans. 1, 1985, (8) 1567–76. 3-Aryl-$\Delta^3$-dihydrofuranone derivatives having herbicidal, acaricidal and insecticidal properties are furthermore known from EP-A-528 156, EP-A 0 647 637 and WO 95/26345.

Certain phenyl-pyrone derivatives which are unsubstituted in the phenyl ring have already been disclosed (cf A. M. Chirazi, T. Kappe and E. Ziegler, Arch. Pharm. 309, 558 (1976) and K.-H. Boltze and K. Heidenbluth, Chem. Ber. 91, 2849), no possible usefulness of these compounds as pest control agents being mentioned. Phenyl-pyrone derivatives which are substituted in the phenyl ring and have herbicidal, acaricidal and insecticidal properties are described in EP-A-588 137.

Certain 5-phenyl-1,3-thiazine derivatives which are unsubstituted in the phenyl ring have already been disclosed (cf. E. Ziegler and E. Steiner, Monatsh. 95 147 (1964), R. Ketcham, T. Kappe and E. Ziegler, J. Heterocycl. Chem. 10, 223 (1973)), no possible use as pest control agents being mentioned for these compounds. 5-Phenyl-1,3-thiazine derivatives which are substituted in the phenyl ring and have a herbicidal, acaricidal and insecticidal action are described in WO 94/14 785.

However, the acaricidal and insecticidal activity and/or range of action and the plant tolerance of these compounds, in particular with respect to crop plants, is not always adequate.

New compounds of the formula (I)

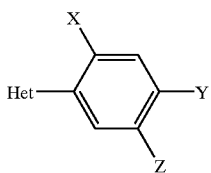

(I)

in which

X represents halogen, alkyl, alkenyl, alkinyl, alkoxy, halogenoalkyl, halogenoalkoxy, cyano or nitro, Y represents hydrogen, halogen, alkyl, alkoxy, halogenoalkyl, halogenoalkoxy, cyano or nitro, Z represents halogen, alkyl, alkoxy, halogenoalkyl, halogenoalkoxy, hydroxyl, cyano, nitro or in each case optionally substituted phenoxy, phenylthio, 5- to 6-membered hetaryloxy, 5- to 6-membered hetarylthio, phenylalkyloxy or phenylalkylthio or Y and Z, together with the carbon atom to which they are bonded, represent a cyclic radical which is optionally substituted and optionally interrupted by heteroatoms, wherein X has one of the abovementioned meanings, Het represents one of the groups

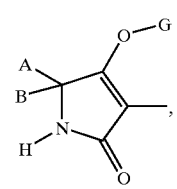

(1)

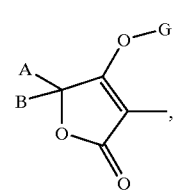

(2)

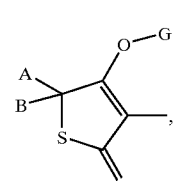

(3)

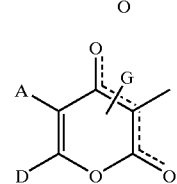

(4)

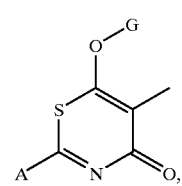

(5)

wherein

A represents hydrogen, or represents alkyl, alkenyl, alkoxyalkyl, polyalkoxyalkyl or alkylthioalkyl which are in each case optionally substituted by halogen, or represents in each case saturated or unsaturated and optionally substituted cycloalkyl or heterocyclyl, or represents aryl, arylalkyl or hetaryl which are in each case optionally substituted by halogen, alkyl, halogenoalkyl, alkoxy, halogenoalkoxy, cyano or nitro, B represents hydrogen, alkyl or alkoxyalkyl, or A and B, together with the carbon atom to which they are bonded, represent a saturated or unsaturated, optionally substituted carbocyclic or heterocyclic radical, D represents hydrogen, or represents an optionally substituted radical from the series consisting of alkyl, alkenyl, alkinyl, alkoxyalkyl, polyalkoxyalkyl, alkylthioalkyl, saturated or unsaturated cycloalkyl, saturated or unsaturated heterocyclyl, arylalkyl, aryl, hetarylalkyl or hetaryl, or A and D, together with the atoms to which they are bonded, represent a carbocyclic or heterocyclic radical which is in each case optionally substituted, G represents hydrogen (a), or represents one of the groups

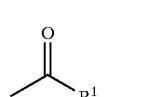
(b)

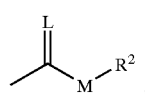
(c)

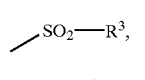
(d)

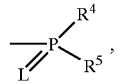
(e)

E
(f)

oder 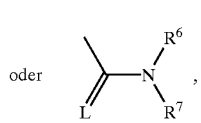
(g)

wherein

E represents one metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyalkyl which are in each case optionally substituted by halogen, or represents cycloalkyl or heterocyclyl which are in each case optionally substituted by halogen, alkyl or alkoxy, or represents in each case optionally substituted phenyl, phenylalkyl, hetaryl, phenoxyalkyl or hetaryloxyalkyl, $R^2$ represents alkyl alkenyl, alkoxyalkyl or polyalkoxyalkyl which are in each case optionally substituted by halogen, or represents in each case optionally substituted cycloalkyl, phenyl or benzyl, $R^3$, $R^4$ and $R^5$ independently of one another represent alkyl, alkoxy, alkylamino, dialkylamino, alkylthio, alkenylthio or cycloalkylthio which are in each case optionally substituted by halogen, or represent in each case optionally substituted phenyl, phenoxy or phenylthio, and $R^6$ and $R^7$ independently of one another represent hydrogen, or represent alkyl, cycloalkyl, alkenyl, alkoxy or alkoxyalkyl which are in each case optionally substituted by halogen, or represent in each case optionally substituted phenyl or benzyl, or, together with the N atom to which they are bonded, form a cyclic radical which optionally contains oxygen or sulphur and is optionally substituted, have now been found.

The compounds of the formula (I) can be in the form of geometric and/or optical rat isomers or isomer mixtures of varying composition, also depending on the nature of the substituents, and these can optionally be separated in the customary manner. The present invention relates both to the pure isomers and to the isomer mixtures, their preparation and use and compositions comprising them. For simplicity, however, reference is always made below to compounds of the formula (I), although this means both the pure compounds and, where appropriate, also mixtures with different contents of isomeric compounds.

Incorporating the meanings (1) to (5) of the group Het, the following main structures (I-1) to (I-5) result:

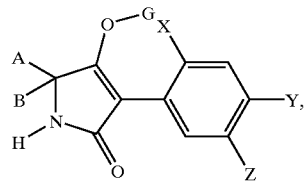
(I-1)

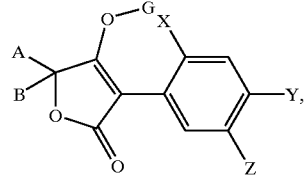
(I-2)

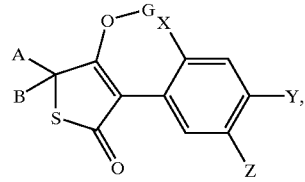
(I-3)

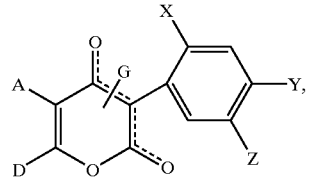
(I-4)

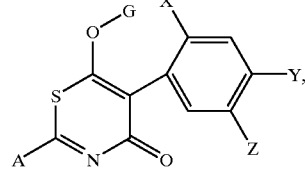
(I-5)

wherein

A, B, D, G, x, Y and Z have the abovementioned meaning.

Incorporating the various meanings (a), (b), (c), (d), (e), (f) and (g) of the group G, the following main structures (I-1-a) to (I-1-g) result if Het represents the group (1)

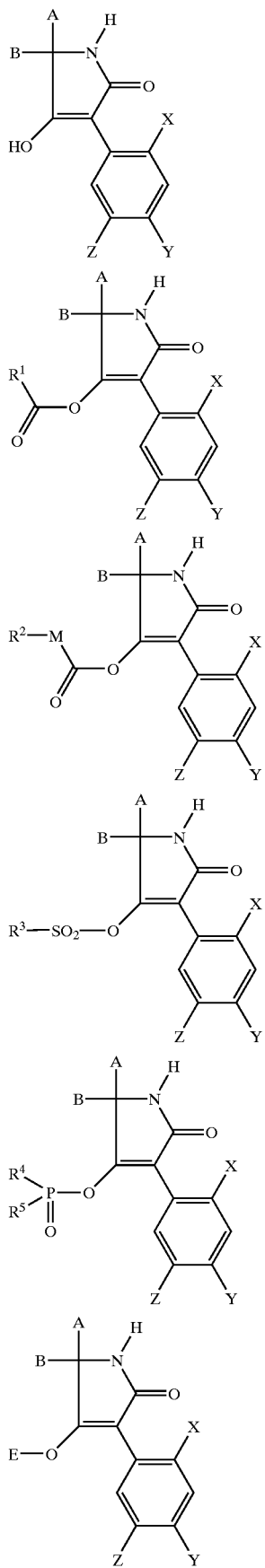
(I-1-a)
(I-1-b)
(I-1-c)
(I-1-d)
(I-1-e)
(I-1-f)
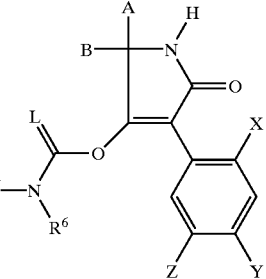
(I-1-g)
wherein
A, B, E, L, M, X, Y, Z, $R^1$, $R^2$, $R^3$, $R^4$, $R^5$, $R^6$ and $R^7$ have the abovementioned meanings.
Incorporating the various meanings (a), (b), (c), (d), (e), (f) and (g) of the group G, the following main structures (I-2-a) to (I-2-g) result if Het represents the group (2)
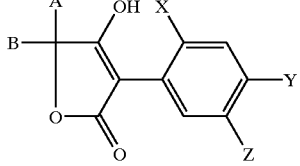
(I-2-a)
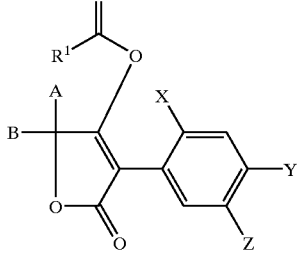
(I-2-b)
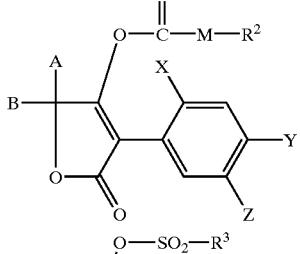
(I-2-c)
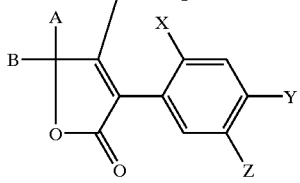
(I-2-d)
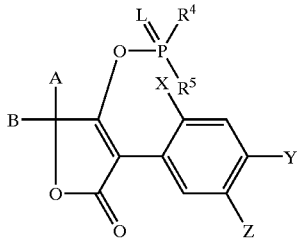
(I-2-e)

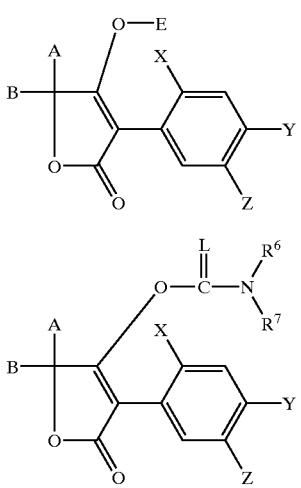
(I-2-f)

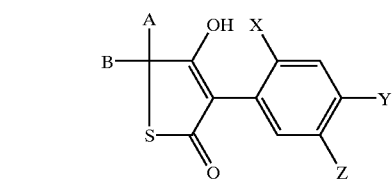
(I-2-g)

wherein

A, B, E, L, M, X, Y, Z, $R^1$, $R^2$, $R^3$, $R^4$, $R^5$, $R^6$ and $R^7$ have the abovementioned meaning.

Incorporating the various meanings (a), (b), (c), (d), (e), (f) and (g) of the group G, the following main structures (I-3-a) to (I-3-g) result if Het represents the group (3)

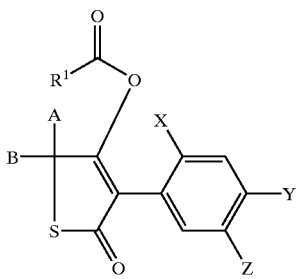
(I-3-a)

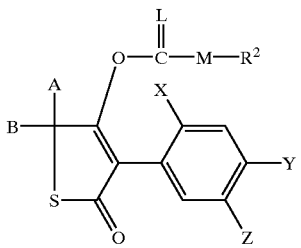
(I-3-b)

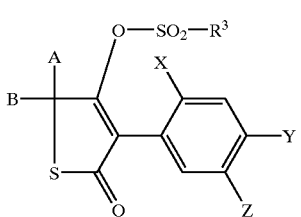
(I-3-c)

(I-3-d)

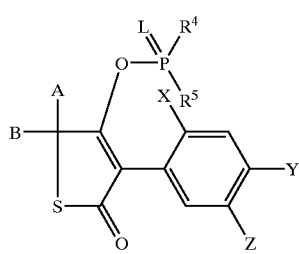
(I-3-e)

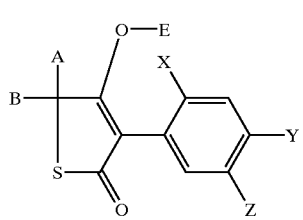
(I-3-f)

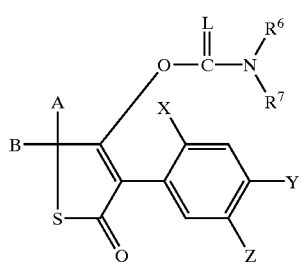
(I-3-g)

wherein

A, B, E, L, M, X, Y, Z. $R^1$, $R^2$, $R^3$, $R^4$, $R^5$, $R^6$ and $R^7$ have the abovementioned meaning.

The compounds of the formula (I-4) can be present in the two isomeric forms of the formulae $(I-4)_a$ and $(I-4)_b$, depending on the position of the substituent G

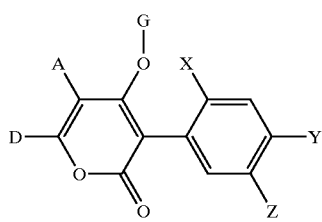
$(I-4)_a$ $(I-4)_b$ which is illustrated by the broken line in the formula (I-4).

The compounds of the formulae $(I-4)_a$ and $(I-4)_b$ can be present both in the form of mixtures and in the form of their pure isomers. Mixtures of the compounds of the formulae $(I-4)_a$ and $(I-4)_b$ can be separated, where appropriate, by physical methods in a manner known per se, for example by chromatographic methods.

For reasons of better clarity, in each case only one of the possible isomers is mentioned below. This does not mean that the compounds cannot be present, where appropriate, in the form of the isomer mixtures or in the other particular isomeric form.

Incorporating the various meanings (a), (b), (c), (d), (e), (f) and (g) of the group G, the following main structures (I-4-a) to (I-4-g) result if Het represents the group (4)

(I-4-a)
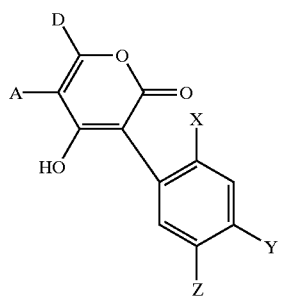

(I-4-b)
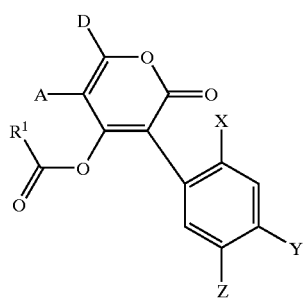

(I-4-c)
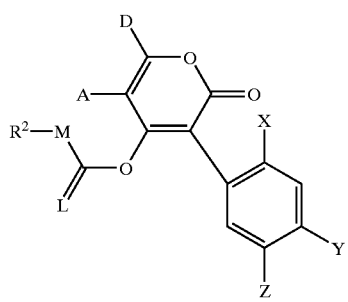

(I-4-d)
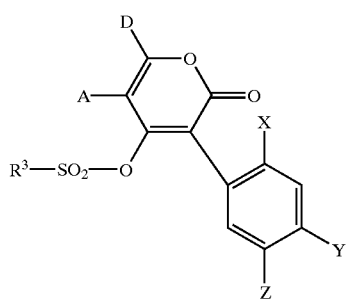

(I-4-e)
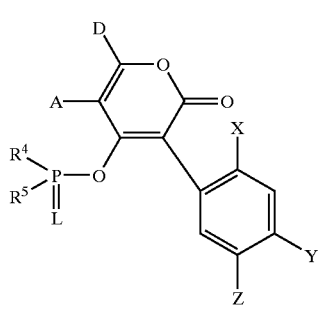

(I-4-f)
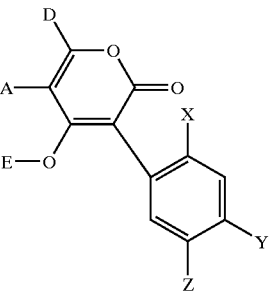

(I-4-g)
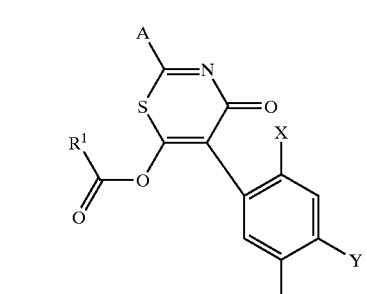

wherein
A, D, E, L, M, X, Y, Z, $R^1$, $R^2$, $R^3$, $R^4$, $R^5$, $R^6$ and $R^7$ have the abovementioned meanings.

Incorporating the various meanings (a), (b), (c), (d), (e), (f) and (g) of the group G, the following main structures (I-5-a) to (I-5-g) result if Het represents the group (5)

(I-5-a)
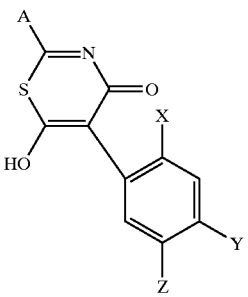

(I-5-b)
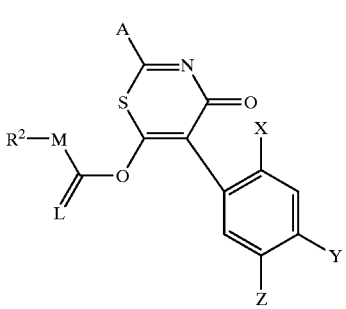

(I-5-c)

-continued (I-5-d)

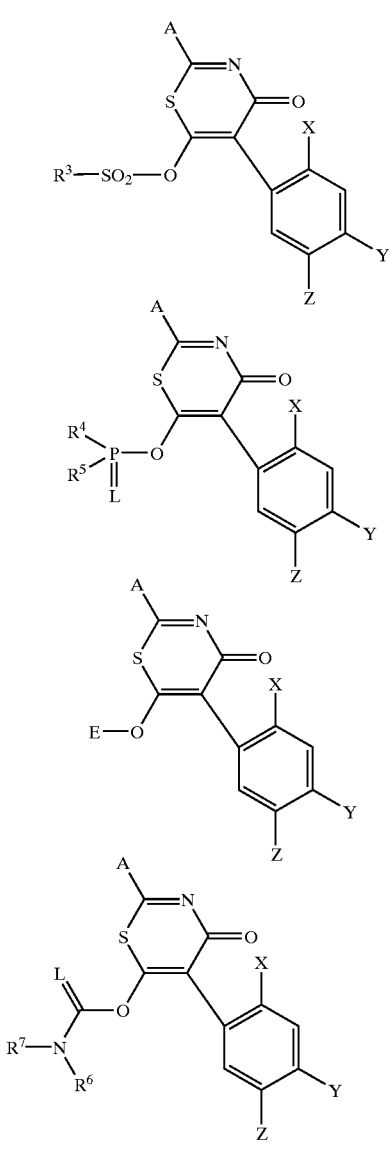

(I-5-e)

(I-5-f)

(I-5-g)

wherein
A, E, L, M, X, Y, Z, $R^1$, $R^2$, $R^3$, $R^4$, $R^5$, $R^6$ and $R^7$ have the abovementioned meanings.

It has furthermore been found that the new compounds of the formula (I) are obtained by one of the processes described below:

(A) compounds of the formula (I-1-a).

(I-1-a)

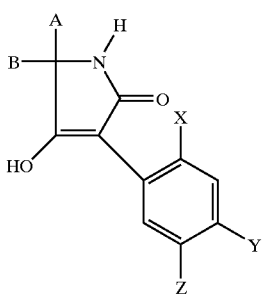

in which
A, B, X, Y and Z have the abovementioned meanings, are obtained when compounds of the formula (II)

(II)

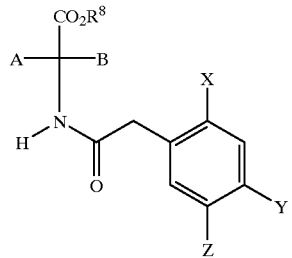

in which
A, B, X, Y and Z have the abovementioned meanings and
$R^8$ represents alkyl (preferably $C_1$–$C_6$-alkyl)

are subjected to an intramolecular condensation reaction in the presence of a diluent and in the presence of a base.

(B) It has furthermore been found that compounds of the formula (I-2-a)

(I-2-a)

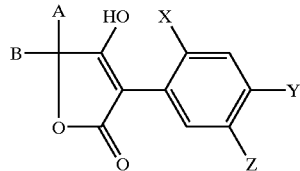

in which
A, B, X, Y and Z have the abovementioned meanings, are obtained when compounds of the formula (III)

(III)

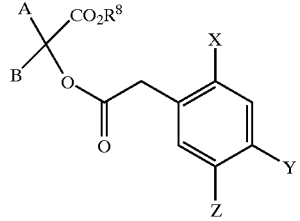

in which
A, B, X, Y, Z and $R^8$ have the abovementioned meanings, are subjected to an intramolecular condensation reaction in the presence of a diluent and in the presence of a base.

(C) It has furthermore been found that compounds of the formula (I-3-a)

(I-3-a)

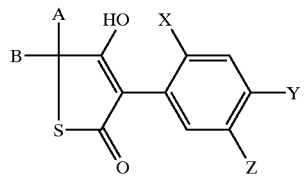

in which

A, B, X, Y and Z have the abovementioned meanings, are obtained when compounds of the formula (IV)

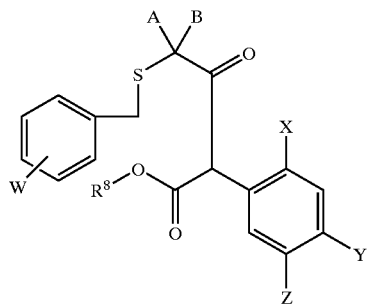

(IV)

in which

A, B. X, Y. Z and $R^8$ have the abovementioned meanings and

W represents hydrogen, halogen, alkyl (preferably $C_1$–$C_6$-alkyl) or alkoxy (preferably $C_1$–$C_8$-alkoxy), are subjected to intramolecular cyclization, if appropriate in the presence of a diluent and in the presence of an acid.

(D) It has furthermore been found that compounds of the formula (I-4-a)

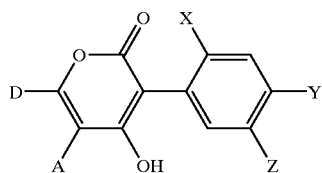

(I-4-a)

in which

A, D, X, Y and Z have the abovementioned meanings, are obtained when compounds of the formula (V)

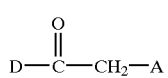

(V)

in which

A and D have the abovementioned meanings, or silylenol ethers thereof of the formula (Va)

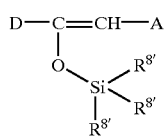

(Va)

in which

A and D have the abovementioned meaning and $R^{8'}$ represents alkyl (preferably methyl), are reacted with compounds of the formula (VI)

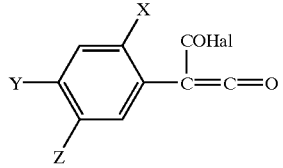

(VI)

in which

X, Y and Z have the abovementioned meanings and

Hal represents halogen (preferably chlorine or bromine), if appropriate in the presence of a diluent and if appropriate in the presence of an acid acceptor.

(E) It has furthermore been found that the compounds of the formula (I-5-a)

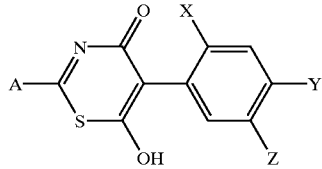

(I-5-a)

in which

A, X, Y and Z have the abovementioned meanings, are obtained when compounds of the formula (VII)

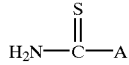

(VII)

in which

A has the abovementioned meaning, are reacted with compounds of the formula (VI)

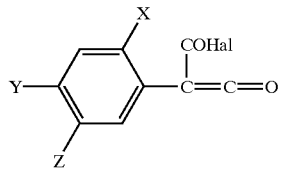

(VI)

in which

Hal, X, Y and Z have the abovementioned meanings, if appropriate in the presence of a diluent and if appropriate in the presence of an acid acceptor.

It has furthermore been found (F) that the compounds of the formulae (I-1-b) to (I-5-b) shown above, in which A, B, D, $R^1$, X, Y and Z have the abovementioned meanings, are obtained when compounds of the formulae (I-1-a) to (I-5-a) shown above, in which A, B, D, X, Y and Z have the abovementioned meanings, are reacted α) with acid halides of the formula (VIII)

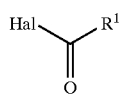
(VIII)

in which
R¹ has the abovementioned meaning and
Hal represents halogen (in particular chlorine or bromine), or β) with carboxylic acid anhydrides of the formula (IX)

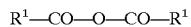
(IX)

in which
R¹ has the abovementioned meaning,
if appropriate in the presence of a diluent and if appropriate in the presence of an acid-binding agent;

(G) that the compounds of the formulae (I-1-c) to (I-5-c) shown above, in which A, B, D, R², M, X, Y and Z have the abovementioned meanings and L represents oxygen, are obtained when compounds of the formulae (I-1-a) to (I-5-a) shown above, in which A, B, D, X, Y and Z have the abovementioned meanings, in each case are reacted
with chloroformic acid esters or chloroformic acid thioesters of the formula (X)

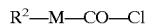
(X)

in which
R² and M have the abovementioned meanings,
if appropriate in the presence of a diluent and if appropriate in the presence of an acid-binding agent;

(H) that compounds of the formulae (I-1-c) to (I-5-c) shown above, in which A, B, D, R², M, X, Y and Z have the abovementioned meanings and L represents sulphur, are obtained when compounds of the formulae (I-1-a) to (I-5-a) shown above, in which A, B, D, X, Y and Z have the abovementioned meanings, in each case
α) are reacted with chloromonothioformic acid esters or chlorodithioformic acid esters of the formula (XI)

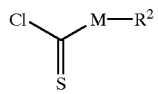
(XI)

in which
M and R² have the abovementioned meanings,
if appropriate in the presence of a diluent and if appropriate in the presence of an acid-binding agent, or
β) are reacted with carbon disulphide and then with compounds of the formula (XII)

(XII)

in which
R² has the abovementioned meaning and
Hal represents chlorine, bromine or iodine,
if appropriate in the presence of a diluent and if appropriate in the presence of a base, (I) that compounds of the formulae (I-1-d) to (I-5-d) shown above, in which A, B, D, R³, X, Y and Z have the abovementioned meanings, are obtained when compounds of the formulae (I-1-a) to (I-5-a) shown above, in which A, B, D, X, Y and Z have the abovementioned meanings, in each case are reacted with sulphonic acid chlorides of the formula (XIII)

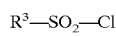
(XIII)

in which
R³ has the abovementioned meaning,
if appropriate in the presence of a diluent and if appropriate in the presence of an acid-binding agent, (J) that compounds of the formulae (I-1-e) to (I-5-e) shown above, in which A, B, D, L, R⁴, R⁵, X, Y and Z have the abovementioned meanings, are obtained when compounds of the formulae (I-1-a) to (I-4-a) shown above, in which A, B, D, X, Y and Z have the abovementioned meanings, in each case are reacted with phosphorus compounds of the formula (XIV)

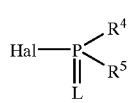
(XIV)

in which
L, R⁴ and R⁵ have the abovementioned meanings and
Hal represents halogen (in particular chlorine or bromine),
if appropriate in the presence of a diluent and if appropriate in the presence of an acid-binding agent, (K) that compounds of the formulae (I-1-f) to (I-5-f) shown above, in which A, B, D, E, X, Y and Z have the abovementioned meanings, are obtained when compounds of the formulae (I-1-a) to (I-5-a), in which A, B, D, X, Y and Z have the abovementioned meanings, in each case are reacted with metal compounds or amines of the formulae (XV) or (XVI)

(XV)

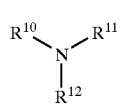
(XVI)

in which
Me represents a mono- or divalent metal (preferably an alkali metal or alkaline earth metal, such as lithium, sodium, potassium, magnesium or calcium),
t represents the number 1 or 2 and
R¹⁰, R¹¹ and R¹² independently of one another represent hydrogen or alkyl (preferably C₁–C₈-alkyl),
if appropriate in the presence of a diluent, (L) that compounds of the formulae (I-1-g) to (I-5-g) shown above, in which A, B, D, L, R⁶, R⁷, X, Y and Z have the abovementioned meanings, are obtained when compounds of the formulae (I-1-a) to (I-5-a) shown above, in which A, B, D, X, Y and Z have the abovementioned meanings, in each case
α) are reacted with isocyanates or isothiocyanates of the formula (XVII)

(XVII)

in which
R⁶ and L have the abovementioned meanings, if appropriate in the presence of a diluent and if appropriate in the presence of a catalyst, or β) are reacted with carbamic acid chlorides or thiocarbamic acid chlorides of the formula (XVIII)

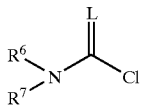

(XVIII)

in which

L, $R^6$ and $R^7$ have the abovementioned meanings, if appropriate in the presence of a diluent and if appropriate in the presence of an acid-binding agent.

It has furthermore been found that the new compounds of the formula (I) have a very good activity as pest control agents, preferably as insecticides, acaricides and herbicides, and furthermore have a very good plant tolerance, in particular with respect to crop plants.

Formula (I) provides a general definition of the compounds according to the invention. Preferred substituents and ranges of the radicals shown in the formulae mentioned above and below are explained below:

X preferably represents halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl, $C_1$–$C_4$-halogenoalkoxy, cyano or nitro, Y preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, Z preferably represents halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano or nitro, or phenoxy, phenylthio, thiazolyloxy, pyridinyloxy, pyrimidyloxy, pyrazolyloxy, phenyl-$C_1$–$C_4$-alkyloxy or phenyl-$C_1$–$C_4$-alkylthio which are in each case optionally substituted by halogen, $C_1$–$C_4$-alkyl, $C_1$–$C_4$-alkoxy, $C_1$–$C_4$-halogenoalkyl, $C_1$–$C_4$-halogenoalkoxy, nitro or cyano, or Y and Z, together preferably represent $C_3$–$C_4$-alkanediyl or $C_3$–$C_4$-alkenediyl which are optionally substituted by halogen, $C_1$–$C_6$-alkyl, $C_1$–$C_6$-alkoxy or $C_1$–$C_4$-halogenoalkyl and in which one to three members can optionally be replaced, independently of one another, by oxygen, sulphur, nitrogen or a carbonyl group, X having one of the abovementioned meanings.

Het preferably represents one of the groups

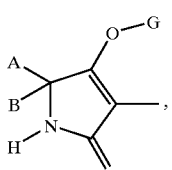

(1)

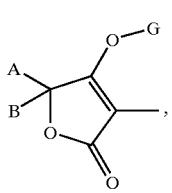

(2)

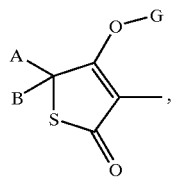

(3)

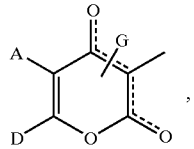

(4)

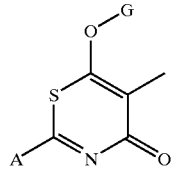

(5)

A preferably represents hydrogen, or represents $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkyl-thio-$C_1$–$C_6$-alkyl which are in each case optionally substituted by halogen, or represents $C_3$–$C_8$-cycloalkyl which is optionally substituted by halogen, $C_1$–$C_6$-alkyl or $C_1$–$C_6$-alkoxy and in which one or two methylene groups are optionally replaced by oxygen and/or sulphur, or represents phenyl, naphthyl, phenyl-$C_1$–$C_6$-alkyl, naphthyl-$C_1$–$C_6$-alkyl or hetaryl having 5 or 6 ring atoms and one to three heteroatoms from the series consisting of oxygen, sulphur and nitrogen, which are in each case optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro.

B preferably represents hydrogen, $C_1$–$C_{12}$-alkyl or $C_1$–$C_8$-alkoxy-$C_1$–$C_6$-alkyl or A, B and the carbon atom to which they are bonded preferably represent $C_3$–$C_{10}$-cycloalkyl or $C_5$–$C_{10}$-cycloalkenyl, wherein one methylene group is optionally replaced by oxygen or sulphur and which are optionally substituted by $C_1$–C8-alkyl, $C_3$–$C_{10}$-cycloalkyl, $C_1$–$C_8$-halogenoalkyl, $C_1$–$C_8$-alkoxy, $C_1$–C8-alkylthio, halogen or phenyl, or A, B and the carbon atom to which they are bonded preferably represent $C_5$–$C_6$-cycloalkyl which is substituted by an alkylenediyl group which optionally contains one or two oxygen and/or sulphur atoms or by an alkylenedioxyl group or by an alkylenedithioyl group, this substituent forming a further five- to eight-membered ring with the carbon atom to which it is bonded, or A, B and the carbon atom to which they are bonded preferably represent $C_3$–$C_8$-cycloalkyl or $C_5$–$C_8$-cycloalkenyl in which two substituents, together with the carbon atom to which they are bonded, represent $C_3$–$C_6$-alkanediyl, $C_3$–$C_6$-alkenediyl or $C_4$–$C_6$-alkanedienediyl which are in each case optionally substituted by $C_1$–$C_6$-alkyl, $C_1$–$C_6$-alkoxy or halogen and wherein in each case one methylene group is optionally replaced by oxygen or sulphur.

D preferably represents hydrogen, or represents $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl which are in each case optionally substituted by halogen, or represents $C_3$–$C_8$-cycloalkyl which is optionally substituted by halogen, $C_1$–$C_4$-alkyl, $C_1$–$C_4$-alkoxy or $C_1$–$C_4$-halogenoalkyl and in which one or two methylene groups which are not directly adjacent are optionally replaced by oxygen and/or sulphur, or represent phenyl, hetaryl having 5 to 6 ring atoms and one or two heteroatoms from the series consisting of oxygen, sulphur and nitrogen, phenyl-$C_1$–$C_6$-alkyl or hetaryl-$C_1$–$C_6$-alkyl having 5 to 6 ring atoms and one or two heteroatoms from the series consisting of oxygen, sulphur and nitrogen, which are in each case optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and D together preferably represent a $C_3$–$C_6$-alkanediyl, $C_3$–$C_6$-alkenediyl or $C_4$–$C_6$-alkadienediyl group in which in each case one methylene group is optionally replaced by oxygen or sulphur and which are in each case optionally substituted by halogen or $C_1$–$C_{10}$-alkyl, $C_1$–$C_6$-alkoxy, $C_1$–$C_6$-alkylthio, $C_3$–$C_7$-cycloalkyl, phenyl or benzyloxy which are in each case optionally substituted by halogen, or by a further $C_3$–$C_6$-alkanediyl, $C_3$–$C_6$-alkenediyl or $C_4$–$C_6$-alkadienediyl group which forms a fused-on ring and in which in each case one methylene group is optionally replaced by oxygen or sulphur and which are optionally substituted by $C_1$–$C_6$-alkyl, or A and D together represent a $C_3$–$C_6$-alkanediyl or $C_3$–$C_6$-alkenediyl group which in each case optionally contains one of the following groups

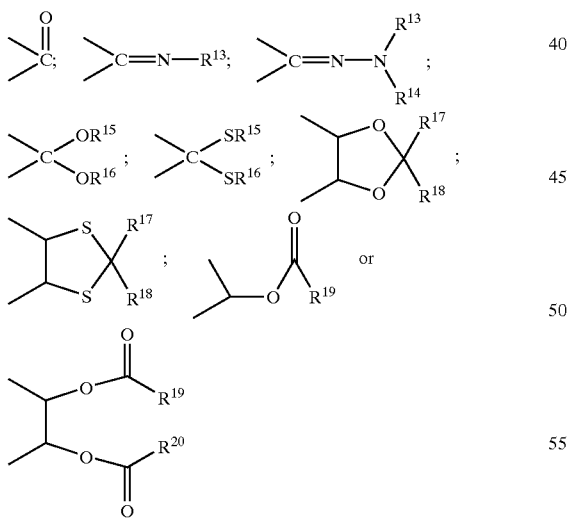

G preferably represents hydrogen (a), or represents one of the groups

-continued

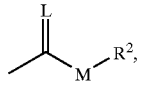

(c)

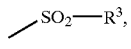

(d)

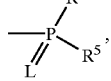

(e)

E or

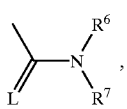

(f)

(g)

in which

E represents one metal ion equivalent or an ammonium ion,

L represents oxygen or sulphur and

M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl which are in each case optionally substituted by halogen, or represents $C_3$–$C_8$-cycloalkyl which is optionally substituted by halogen, $C_1$–$C_6$-alkyl or $C_1$–$C_6$-alkoxy and in which one or two methylene groups are optionally replaced by oxygen and/or sulphur, or represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogeno-alkoxy, $C_1$–$C_6$-alkylthio or $C_1$–$C_6$-alkylsulphonyl, or represents phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents 5- or 6-membered hetaryl having one or two heteroatoms from the series consisting of oxygen, sulphur and nitrogen which is optionally substituted by halogen or $C_1$–$C_6$-alkyl, or represents phenoxy-$C_1$–$C_6$-alkyl which is optionally substituted by halogen or $C_1$–$C_6$-alkyl or represents 5- or 6-membered hetaryloxy-$C_1$–$C_6$-alkyl which has one or two heteroatoms from the series consisting of oxygen, sulphur and nitrogen and is optionally substituted by halogen, amino or $C_1$–$C_6$-alkyl.

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl which are in each case optionally substituted by halogen, or represents $C_3$–$C_8$-cycloalkyl which is optionally substituted by halogen, $C_1$–$C_6$-alkyl or $C_1$–$C_6$-alkoxy, or represents phenyl or benzyl which are in each case optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy.

$R^3$ preferably represents $C_1$–$C_8$-alkyl which is optionally substituted by halogen, or phenyl or benzyl which are in each case optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ and $R^5$ independently of one another preferably represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio which are in each case optionally substituted by halogen, or represent phenyl, phenoxy or phenylthio which are in each case optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, or represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl which are in each case optionally substituted by halogen, or represent phenyl or benzyl which are in each case optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical which is optionally substituted by $C_1$–$C_6$-alkyl and in which one methylene group is optionally replaced by oxygen or sulphur.

$R^{13}$ preferably represents hydrogen, or $C_1$–$C_8$-alkyl or $C_1$–$C_8$-alkoxy which are in each case optionally substituted by halogen, or represents $C_3$–$C_8$-cycloalkyl which is optionally substituted by halogen, $C_1$–$C_4$-alkyl or $C_1$–$C_4$-alkoxy and in which one methylene group is optionally replaced by oxygen or sulphur, or represents phenyl, phenyl-$C_1$–$C_4$-alkyl or phenyl-$C_1$–$C_4$-alkoxy which are in each case optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$R^{14}$ preferably represents hydrogen or $C_1$–$C_8$-alkyl, or $R^{13}$ and $R^{14}$ together preferably represent $C_4$–$C_6$-alkanediyl.

$R^{15}$ and $R^{16}$ are identical or different and preferably represent $C_1$–$C_6$-alkyl, or $R_{15}$ and $R_{16}$ together preferably represent a $C_2$–$C_4$-alkanediyl radical which is optionally substituted by $C_1$–$C_6$-alkyl or by phenyl which is optionally substituted by halogen, $C_1$–$C_4$-alkyl, $C_1$–$C_4$-halogenoalkyl, $C_1$–$C_4$-alkoxy, $C_1$–$C_4$-halogenoalkoxy, nitro or cyano.

$R^{17}$ and $R^{18}$ independently of one another preferably represent hydrogen, or represent $C_1$–$C_8$-alkyl which is optionally substituted by halogen, or represent phenyl which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, or $R^{17}$ and $R^{18}$, together with the carbon atom to which they are bonded, represent $C_5$–$C_7$-cycloalkyl which is optionally substituted by $C_1$–$C_4$-alkyl and in which one methylene group is optionally replaced by oxygen or sulphur.

$R^{19}$ and $R^{20}$ independently of one another preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

X particularly preferably represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Y particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Z particularly preferably represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxy, cyano or nitro, or phenoxy or benzyloxy which are in each case optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, or Y and Z, together particularly preferably represent $C_3$–$C_4$-alkanediyl or $C_3$–$C_4$-alkenediyl which are optionally substituted by fluorine, chlorine, bromine, $C_1$–$C_4$-alkyl, $C_1$–$C_4$-alkoxy or $C_1$–$C_2$-halogenoalkyl and in which one or two members which are not directly adjacent can optionally be replaced, independently of one another, by oxygen, sulphur or nitrogen, X having one of the abovementioned meanings.

Het particularly preferably represents one of the groups

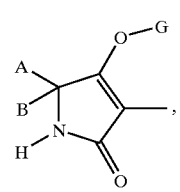

(1)

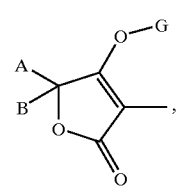

(2)

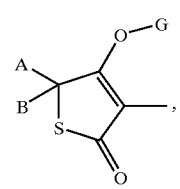

(3)

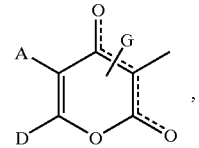

(4)

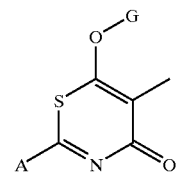

(5)

A particularly preferably represents hydrogen, or represents $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl which are in each case optionally substituted by fluorine or chlorine, or represents $C_3$–$C_7$-cycloalkyl which is optionally substituted by fluorine, chlorine, $C_1$–$C_4$-alkyl or $C_1$–$C_4$-alkoxy and in which one or two methylene groups are optionally replaced by oxygen and/or sulphur, or represents phenyl, furanyl, pyridyl, imidazolyl, triazolyl, pyrazolyl, indolyl, thiazolyl, thienyl or phenyl-$C_1$–$C_4$-alkyl which are in each case optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro.

B particularly preferably represents hydrogen, $C_1$–$C_{10}$-alkyl or $C_1$–$C_6$-alkoxy-$C_1$–$C_4$-alkyl or A, B and the carbon atom to which they are bonded particularly preferably represent $C_3$–$C_8$-cycloalkyl or $C_5$–$C_8$-cycloalkenyl, wherein in each case one methylene group is optionally replaced by oxygen or sulphur and which are optionally substituted by $C_1$–$C_6$-alkyl, $C_3$–$C8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom to which they are bonded particularly preferably represent $C_5$–$C_6$-cycloalkyl which is substituted by an alkylenediyl group which optionally contains one or two oxygen or sulphur atoms or by an alkylenedioxyl group or by an alkylenedithiol group, this substituent, together with the carbon atom to which it is bonded, forming a further five- to seven-membered ring, or A, B and the carbon atom to which they are bonded particularly preferably represent $C_3$–$C_6$-cycloalkyl or $C_5$–$C_6$-cycloalkenyl in which two substituents, together with the carbon atom to which they are bonded, represent $C_3$–$C_5$-alkanediyl, $C_3$–$C_5$-alkenediyl or butadienediyl which are in each case optionally substituted by $C_1$–$C_4$-alkyl, $C_1$–$C_4$-alkoxy, fluorine, chlorine or bromine, wherein in each case one methylene group is optionally replaced by oxygen or sulphur.

D particularly preferably represents hydrogen, or represents $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alk-oxy-$C_2$–$C_6$-alkyl or $C_1$–$C_8$-alkylthio-$C_2$–$C_6$-alkyl which are in each case optionally substituted by fluorine or chlorine, or represents $C_3$–$C_7$-cycloalkyl which is optionally substituted by fluorine, chlorine, $C_1$–$C_4$-alkyl, $C_1$–$C_4$-alkoxy or $C_1$–$C_2$-halogenoalkyl and in which one or two methylene groups which are not directly adjacent are optionally replaced by oxygen and/or sulphur, or represents phenyl, furanyl, imidazolyl, pyridyl, thiazolyl, pyrazolyl, pyrimidyl, pyrrolyl, thienyl, triazolyl or phenyl-$C_1$–$C_4$-alkyl which are in each case optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, or A and D together particularly preferably represent a $C_3$–$C_5$-alkanediyl or $C_3$–$C_5$-alkenediyl group wherein in each case one carbon atom is optionally replaced by oxygen or sulphur and which are optionally substituted by fluorine, chlorine or by $C_1$–$C_6$-alkyl, $C_1$–$C_4$-alkoxy, $C_1$–$C_4$-alkylthio, $C_3$–$C_6$-cycloalkyl, phenyl or benzyloxy which are in each case optionally substituted by fluorine or chlorine, or which in each case optionally contain one of the following groups:

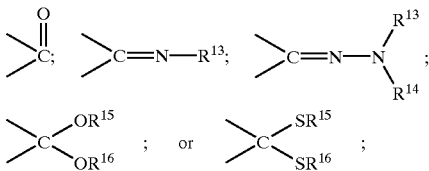

G particularly preferably represents hydrogen (a), or represents one of the groups

 (b)

 (c)

 (d)

 (e)

E (f)
or

 (g)

in which
E represents one metal ion equivalent or an ammonium ion,
L represents oxygen or sulphur and
M represents oxygen or sulphur.
$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl which are in each case optionally substituted by fluorine or chlorine, or represents $C_3$–$C_7$-cycloalkyl which is optionally substituted by fluorine, chlorine, $C_1$–$C_5$-alkyl or $C_1$–$C_5$-alkoxy and in which one or two methylene groups are optionally replaced by oxygen and/or sulphur, or represents phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, or represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents pyrazolyl, thiazolyl, pyridyl, pyrimidyl, furanyl or thienyl which are in each case optionally substituted by fluorine, chlorine, bromine or $C_1$–$C_4$-alkyl, or represents phenoxy-$C_1$–$C_5$-alkyl which is optionally substituted by fluorine, chlorine, bromine or $C_1$–$C_4$-alkyl, or represents pyridyloxy-$C_1$–$C_5$-alkyl, pyrimidyloxy-$C_1$–$C_5$-alkyl or thiazolyl-oxy-$C_1$–$C_5$-alkyl which are in each case optionally substituted by fluorine, chlorine, bromine, amino or $C_1$–$C_4$-alkyl.

$R^2$ particularly preferably represents $C_1$–$C_{16}$-alkyl, $C_2$–$C_{16}$-alkenyl, $C_1$–$C_6$-alk-oxy-$C_2$–$C_6$-alkyl or poly-$C_1$–$C_6$-alkoxy-$C_2$–$C_6$-alkyl which are in each case optionally substituted by fluorine or chlorine, or represents $C_3$–$C_7$-cycloalkyl which is optionally substituted by fluorine, chlorine, $C_1$–$C_4$-alkyl or $C_1$–$C_4$-alkoxy, or represents phenyl or benzyl which are in each case optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy.

$R^3$ particularly preferably represents $C_1$–$C_6$-alkyl which is optionally substituted by fluorine or chlorine, or phenyl or benzyl which are in each case optionally substituted by fluorine, chlorine, bromine, $C_1$–$C_4$-alkyl, $C_1$–$C_4$-alkoxy, $C_1$–$C_2$-halogenoalkoxy, $C_1$–$C_2$-halogenoalkyl, cyano or nitro.

$R^4$ and $R^5$ independently of one another particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio which are in each case optionally substituted by fluorine or chlorine, or represent phenyl, phenoxy or phenylthio which are in each case optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl which are in each case optionally substituted by fluorine or chlorine, or represent phenyl or benzyl which are in each case optionally substituted by fluorine, chlorine, bromine, $C_1$–$C_5$-halogenoalkyl, $C_1$–$C_5$-alkyl or $C_1$–$C_5$-alkoxy, or together represent a $C_3$–$C_6$-alkylene radical which is optionally substituted by $C_1$–$C_4$-alkyl and in which one methylene group is optionally replaced by oxygen or sulphur.

$R^{13}$ particularly preferably represents hydrogen, or $C_1$–$C_6$-alkyl or $C_1$–$C_6$-alkoxy which are in each case optionally substituted by fluorine or chlorine, or represents $C_3$–$C_7$-cycloalkyl which is optionally substituted by fluorine, $C_1$–$C_2$-alkyl or $C_1$–$C_2$-alkoxy and in which one methylene group is optionally replaced by oxygen or sulphur, or represents phenyl, phenyl-$C_1$–$C_3$-alkyl or phenyl-$C_1$–$C_2$-alkyloxy which are in each case optionally substituted by fluorine, chlorine, bromine, $C_1$–$C_5$-alkyl, $C_1$–$C_5$-alkoxy, $C_1$–$C_2$-halogenoalkyl, $C_1$–$C_2$-halogenoalkoxy, nitro or cyano.

$R^{14}$ particularly preferably represents hydrogen or $C_1$–$C_6$-alkyl, or $R^{13}$ and $R^{14}$ together particularly preferably represent $C_4$–$C_6$-alkanediyl.

$R^{15}$ and $R^{16}$ are identical or different and particularly preferably represent $C_1$–$C_4$-alkyl, or $R^{15}$ and $R^{16}$ together particularly preferably represent a $C_2$–$C_3$-alkanediyl radical which is optionally substituted by $C_1$–$C_4$-alkyl or by phenyl which is optionally substituted by fluorine, chlorine, bromine, $C_1$–$C_2$-alkyl, $C_1$–$C_2$-halogenoalkyl, $C_1$–$C_2$-alkoxy, $C_1$–$C_2$-halogenoalkoxy, nitro or cyano.

X especially preferably represents fluorine, chlorine, bromine, methyl, ethyl, propyl, butyl, iso-butyl, iso-propyl, tert-butyl, methoxy, ethoxy, propoxy, iso-propoxy, trifluoromethyl, trifluoromethoxy, difluoromethoxy, cyano or nitro, Y especially preferably represents hydrogen, fluorine, chlorine, bromine, methyl, ethyl, propyl, iso-propyl, butyl, iso-butyl, tert-butyl, methoxy, ethoxy, propoxy, iso-propoxy, trifluoromethyl, trifluoromethoxy, difluoromethoxy, cyano or nitro, Z especially preferably represents fluorine, chlorine, bromine, methyl, ethyl, propyl, butyl, iso-butyl, iso-propyl, tert-butyl, methoxy, ethoxy, propoxy, iso-propoxy, trifluoromethyl, trifluoromethoxy, difluoromethoxy, cyano or nitro, or Y and Z, together especially preferably represent $C_3$–$C_4$-alkanediyl which is optionally substituted by fluorine, chlorine, methyl, ethyl, propyl, iso-propyl, methoxy, ethoxy, propoxy, iso-propoxy or trifluoromethyl and in which two members which are not directly adjacent are optionally replaced by oxygen, X having one of the abovementioned meanings.

Het especially preferably represents one of the groups

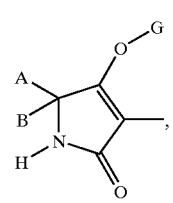
(1)

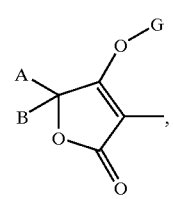
(2)

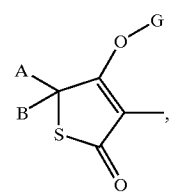
(3)

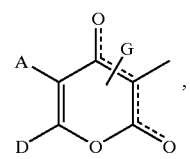
(4)

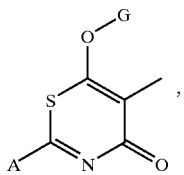

A especially preferably represents hydrogen, or represents $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl which are in each case optionally substituted by fluorine or chlorine, or represents $C_3$–$C_6$-cycloalkyl which is optionally substituted by fluorine, chlorine, methyl or methoxy and in which one or two methylene groups are optionally replaced by oxygen and/or sulphur, or represents phenyl, pyridyl or benzyl which are in each case optionally substituted by fluorine, chlorine, bromine, methyl, ethyl, n-propyl, iso-propyl, methoxy, ethoxy, trifluoromethyl, trifluoromethoxy, cyano or nitro.

B especially preferably represents hydrogen, $C_1$–$C_8$-alkyl or $C_1$–$C_4$-alkoxy-$C_1$–$C_2$-alkyl or A, B and the carbon atom to which they are bonded especially preferably represent $C_3$–$C_8$-cycloalkyl or $C_5$–$C_8$-cycloalkenyl, wherein in each case one methylene group is optionally replaced by oxygen or sulphur and which are optionally substituted by methyl, ethyl, n-propyl, iso-propyl, butyl, iso-butyl, sec-butyl, tert-butyl, cyclohexyl, trifluoromethyl, methoxy, ethoxy, n-propoxy, iso-propoxy, butoxy, iso-butoxy, sec-butoxy, tert-butoxy, methylthio, ethylthio, fluorine, chlorine or phenyl, or A, B and the carbon atom to which they are bonded especially preferably represent $C_5$–$C_6$-cycloalkyl which is substituted by an alkylenediyl group which optionally contains an oxygen or sulphur atom or by an alkylene-dioxyl group, this substituent forming a further five- or six-membered ring with the carbon atom to which it is bonded, or A, B and the carbon atom to which they are bonded especially preferably represent $C_3$–$C_6$-cycloalkyl or $C_5$–$C_6$-cycloalkenyl in which two substituents, together with the carbon atoms to which they are bonded, represent $C_3$–$C_4$-alkanediyl, $C_3$–$C_4$-alkenediyl or butadienediyl, wherein in each case one methylene group is optionally replaced by oxygen or sulphur.

D especially preferably represents hydrogen, or represents $C_1$–$C_8$-alkyl, $C_3$–C4-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl which are in each case optionally substituted by fluorine or chlorine and in which one or two methylene groups which are not directly adjacent are optionally replaced by oxygen and/or sulphur, or represent phenyl, furanyl, pyridyl, thienyl or benzyl which are in each case optionally substituted by fluorine, chlorine, bromine, methyl, ethyl, n-propyl, iso-propyl, methoxy, ethoxy, trifluoromethyl, trifluoromethoxy, cyano or nitro, or A and D together especially preferably represent a $C_3$–$C_5$-alkanediyl or $C_3$–$C_5$-alkenediyl group wherein in each case one methylene group is optionally replaced by oxygen or sulphur and which are optionally substituted by fluorine, chlorine or by $C_1$–$C_6$-alkyl, $C_1$–$C_4$-alkoxy, $C_1$–$C_4$-alkylthio, $C_3$–$C_6$-cycloalkyl, phenyl or benzyloxy which are in each case optionally substituted by fluorine or chlorine.

G especially preferably represents hydrogen (a), or represents one of the groups

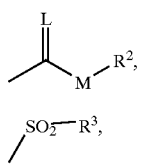

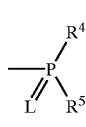

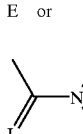

E or

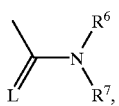

in which

E represents one metal ion equivalent or an ammonium ion,

L represents oxygen or sulphur and

M represents oxygen or sulphur.

$R^1$ especially preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl which are in each case optionally substituted by fluorine or chlorine, or represents $C_3$–$C_6$-cycloalkyl which is optionally substituted by fluorine, chlorine, methyl, ethyl, n-propyl, i-propyl, n-butyl, i-butyl, tert-butyl, methoxy, ethoxy, n-propoxy or iso-propoxy and in which one or two methylene groups are optionally replaced by oxygen and/or sulphur, or represents phenyl which is optionally substituted by fluorine, chlorine, bromine, cyano, nitro, methyl, ethyl, n-propyl, i-propyl, methoxy, ethoxy, trifluoromethyl, trifluoromethoxy, methylthio, ethylthio, methylsulphonyl or ethylsulphonyl, or represents benzyl which is optionally substituted by fluorine, chlorine, bromine, methyl, ethyl, n-propyl, i-propyl, methoxy, ethoxy, trifluoromethyl or trifluoromethoxy, or represents furanyl, thienyl or pyridyl which are in each case optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyl oxy-$C_1$–$C_4$-alkyl or thiazolyl-oxy-$C_1$–$C_4$-alkyl which are in each case optionally substituted by fluorine, chlorine, amino, methyl or ethyl.

R² especially preferably represents C₁–C₁₄-alkyl, C₂–C₁₄-alkenyl, C₁–C₄-alk-oxy-C₂–C₆-alkyl or poly-C₁–C₄-alkoxy-C₂–C₆-alkyl which are in each case optionally substituted by fluorine or chlorine,
or represents C₃–C₆-cycloalkyl which is optionally substituted by fluorine, chlorine, methyl, ethyl, n-propyl, iso-propyl or methoxy,
or represents phenyl or benzyl which are in each case optionally substituted by fluorine, chlorine, cyano, nitro, methyl, ethyl, n-propyl, i-propyl, methoxy, ethoxy, trifluoromethyl or trifluoromethoxy.

R³ especially preferably represents methyl, ethyl, propyl, iso-prpyl, butyl or tert-butyl which are optionally substituted by fluorine or chlorine, or phenyl or benzyl which are in each case optionally substituted by fluorine, chlorine, bromine, methyl, ethyl, iso-propyl, tert-butyl, methoxy, ethoxy, iso-propoxy, trifluoromethyl, trifluoromethoxy, cyano or nitro.

R⁴ and R⁵ independently of one another especially preferably represent C₁–C₄-alkyl, C₁–C₄-alkoxy, C₁–C₄-alkylamino, di-(C₁–C₄-alkyl)amino or C₁–C₄-alkylthio which are in each case optionally substituted by fluorine or chlorine, or represent phenyl, phenoxy or phenylthio which are in each case optionally substituted by fluorine, chlorine, bromine, nitro, cyano, methyl, methoxy, trifluoromethyl or trifluoromethoxy.

R⁶ and R⁷ independently of one another especially preferably represent hydrogen, or represent C₁–C₄-alkyl, C₃–C₆-cycloalkyl, C₁–C₄-alkoxy, C₃–C₄-alkenyl or C₁–C₄-alkoxy-C₂–C₄-alkyl which are in each case optionally substituted by fluorine or chlorine, or represent phenyl or benzyl which are in each case optionally substituted by fluorine, chlorine, bromine, methyl, methoxy or trifluoromethyl, or together represent a C₅–C₆-alkylene radical which is optionally substituted by methyl or ethyl and in which one methylene group is optionally replaced by oxygen or sulphur.

The abovementioned general definitions of radicals and explanations or those given in preferred ranges can be combined with one another as desired, that is to say also between the particular ranges and preferred ranges. They apply accordingly to the end products and to the precursors and intermediate products.

The compounds of the formula (I) in which a combination of the meanings given above as preferred (preferably) is present are preferred according to the invention.

The compounds of the formula (I) in which a combination of the meanings given above as particularly preferred is present are particularly preferred according to the invention.

The compounds of the formula (I) in which a combination of the meanings given above as especially preferred is present are especially preferred according to the invention.

Saturated or unsaturated hydrocarbon radicals such as alkyl or alkenyl, also in combination with heteroatoms, such as, for example, in alkoxy, can in each case be straight-chain or branched where possible.

Optionally substituted radicals can be mono- or polysubstituted, and the substituents can be identical or different in the case of polysubstitutions.

The following compounds of the formula (I-1-a) may be mentioned specifically, in addition to the compounds mentioned in the preparation examples:

TABLE 1

X = CH₃; Y = CH₃; Z = CH₃

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |

—(CH₂)₂—
—(CH₂)₄—
—(CH₂)₅—
—(CH₂)₆—
—(CH₂)₇—
—(CH₂)₂—O—(CH₂)₂—
—(CH₂)₂—S—(CH₂)₂—
—CH₂—CHCH₃—(CH₂)₃—
—(CH₂)₂—CHCH₃—(CH₂)₂—
—(CH₂)₂—CHC₂H₅—(CH₂)₂—
—(CH₂)₂—CHC₃H₇—(CH₂)₂—
—(CH₂)₂—CHi-C₃H₇—(CH₂)₂—
—(CH₂)₂—CHOCH₃—(CH₂)₂—
—(CH₂)₂—CHOC₂H₅—(CH₂)₂—
—(CH₂)₂—CHOC₃H₇—(CH₂)₂—
—(CH₂)₂—CHiO-C₃H₇—(CH₂)₂—
—(CH₂)₂—C(CH₃)₂—(CH₂)₂—
—CH₂—(CHCH₃)₂—(CH₂)₂—

—CH₂—CH—(CH₂)₂—CH—
         └—CH₂—┘

—CH₂—CH————CH—CH₂—
         └—(CH₂)₄—┘

—CH₂—CH————CH—(CH₂)₂—
         └—(CH₂)₃—┘

TABLE 1-continued

[Structure: pyrrolinone with OH, A, B substituents on 5-position, phenyl with X, Y, Z substituents]

X = CH₃; Y = CH₃; Z = CH₃

| A | B |
|---|---|
| | [indanyl] |
| | [tetrahydronaphthyl] |

Table 2: A and B have the same meaning as in Table 1, with X=CH₃; Y=Cl; Z=CH₃

Table 3: A and B have the same meaning as in Table 1, with X=Cl; Y=Cl; Z=Cl

The following compounds of the formula (I-2-a) may be mentioned specifically in addition to the compounds mentioned in the preparation examples:

TABLE 4

[Structure: furanone with OH, A, B substituents, phenyl with X, Y, Z substituents]

X = CH₃; Y = CH₃; Z = CH₃

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| [cyclopropyl] | CH₃ |
| [cyclopentyl] | CH₃ |

TABLE 4-continued

[Structure: furanone with OH, A, B substituents, phenyl with X, Y, Z substituents]

X = CH₃; Y = CH₃; Z = CH₃

| A | B |
|---|---|
| [cyclohexyl] | CH₃ |

—(CH₂)₂—
—(CH₂)₄—
—(CH₂)₅—
—(CH₂)₆—
—(CH₂)₇—
—(CH₂)₂—O—(CH₂)₂—
—(CH₂)₂—S—(CH₂)₂—
—CH₂—CHCH₃—(CH₂)₃—
—(CH₂)₂—CHCH₃—(CH₂)₂—
—(CH₂)₂—CHC₂H₅—(CH₂)₂—
—(CH₂)₂—CHC₃H₇—(CH₂)₂—
—(CH₂)₂—CHi—C₃H₇—(CH₂)₂—
—(CH₂)₂—CHOCH₃—(CH₂)₂—
—(CH₂)₂—CHOC₂H₅—(CH₂)₂—
—(CH₂)₂—CHOC₃H₇—(CH₂)₂—
—(CH₂)₂—CHiO—C₃H₇—(CH₂)₂—
—(CH₂)₂—C(CH₃)₂—(CH₂)₂—
—CH₂—(CHCH₃)₂—(CH₂)₂—

—CH₂—CH—(CH₂)₂—CH—
            |_____CH₂_____|

—CH₂—CH————CH—CH₂—
       |____(CH₂)₄____|

—CH₂—CH————CH—(CH₂)₂—
       |____(CH₂)₃____|

[indanyl]

[tetrahydronaphthyl]

Table 5: A and B have the same meaning as in Table 4, with X=CH₃; Y=Cl; Z=CH₃

Table 6: A and B have the same meaning as in Table 4, with X=Cl; Y=Cl; Z=Cl

The following compounds of the formula (I-3-a) may be mentioned specifically in addition to the compounds mentioned in the preparation examples:

TABLE 7

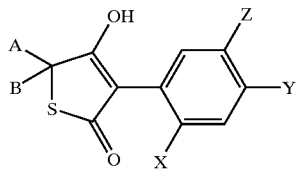

X = CH₃; Y = CH₃; Z = CH₃

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHiO—C₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH—CH₂— (with bridging CH₂) | |
| —CH₂—CH—CH—CH₂— (with bridging (CH₂)₄) | |
| —CH₂—CH—CH—(CH₂)₂— (with bridging (CH₂)₃) | |

TABLE 7-continued

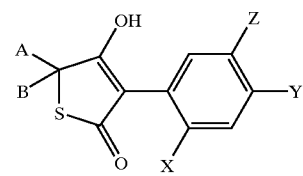

X = CH₃; Y = CH₃; Z = CH₃

| A | B |
|---|---|
| indanyl | |
| tetrahydronaphthyl | |

Table 8: A and B have the same meaning as in Table 7, with X=CH₃; Y=Cl; Z=CH₃

Table 9: A and B have the same meaning as in Table 7, with X=Cl; Y=Cl; Z=Cl

The following compounds of the formula (I-4-a) may be mentioned specifically in addition to the compounds mentioned in the preparation examples:

TABLE 10

X = CH₃; Y = CH₃; Z = CH₃

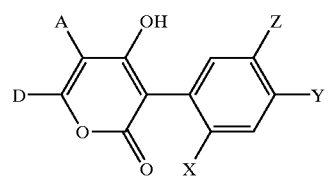

| A | D |
|---|---|
| H | CH₃ |
| H | C(CH₃)₃ |
| H | C(CH₃)₂CH₂Cl |
| CH₃ | CH₃ |
| CH₃ | CH₂CHCH₃CH₂CH₃ |
| H | CH=C(CH₃)₂ |
| CH₃ | 4-F-C₆H₄ |
| CH₃ | 4-Cl-C₆H₄ |
| CH₃ | 2,4-F₂-C₆H₃ |

TABLE 10-continued

X = CH₃; Y = CH₃; Z = CH₃

| A | D |
|---|---|
| CH₃ | 3,4-dichlorophenyl |
| CH₃ | 4-OCF₃-phenyl |
| H | phenyl |
| CH₃ | 2-furyl |
| CH₃ | 2-thienyl |
| CH₃ | 2-pyridyl |
| CH₃ | 3-pyridyl |
| CH₃ | 4-pyridyl |
| H | 2,4-dimethyl-5-thiazolyl |
| CH₃ | C₅H₉ |
| CH₃ | C₃H₅ |
| H | C₃H₄Cl |
| (CH₂)₃ | |
| (CH₂)₄ | |
| C(CH₃)₂OC(CH₃)₂ | |

Table 11: A and D have the same meaning as in Table 10, with X=CH₃; Y=Cl; Z=CH₃

Table 12: A and D have the same meaning as in Table 10, with X=Cl; Y=Cl; Z=Cl

The following compounds of the formula (I-5-a) may be mentioned specifically in addition to the compounds mentioned in the preparation examples:

TABLE 13

X = CH₃; Y = CH₃; Z = CH₃

| A |
|---|
| CH₃ |
| CH(CH₃)₂ |
| phenyl |
| 4-F-phenyl |
| 3-Cl-4-F-phenyl |
| 2-F-phenyl |

Table 14: A has the same meaning as in Table 13, with X=CH₃; Y=Cl; Z=CH₃

Table 15: A has the same meaning as in Table 13, with X=Cl; Y=Cl; Z=Cl

If ethyl N-[(4,5-dichloro-2-methyl)-phenylacetyl]-1-amino-4-ethyl-cyclohexane-carboxylate is used as the starting substance according to process (A), the course of the process according to the invention can be represented by the following equation:

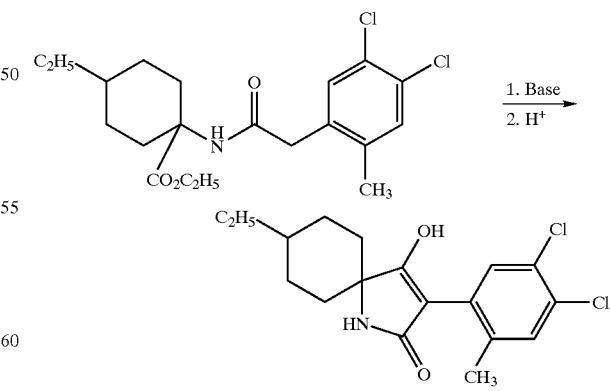

If ethyl O-[(2,5-dichloro-4-methyl)-phenylacetyl]-hydroxyacetate is used according to process (B), the course of the process according to the invention can be represented by the following equation:

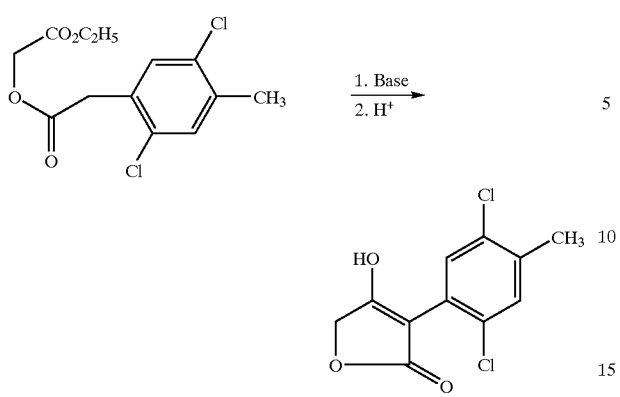

If ethyl 2-[(2-chloro-4,5-dimethyl)-phenyl]-4-(4-methoxy)-benzylmercapto-4-methyl-3-oxo-valerate is used according to process (C), the course of the process according to the invention can be represented by the following equation:

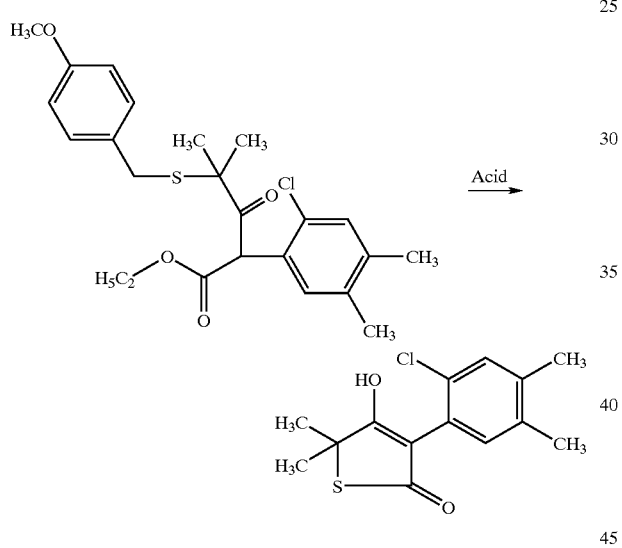

If, for example, (chlorocarbonyl)-2-[(4,5-dichloro-2-methyl)-phenyl]-ketene and acetone are used as starting compounds according to process (D), the course of the process according to the invention can be represented by the following equation:

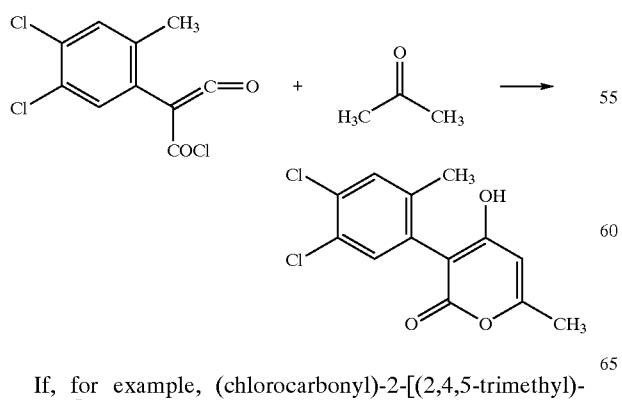

If, for example, (chlorocarbonyl)-2-[(2,4,5-trimethyl)-phenyl]-ketene and thiobenzamide are used as starting compounds according to process (E), the course of the process according to the invention can be represented by the following equation:

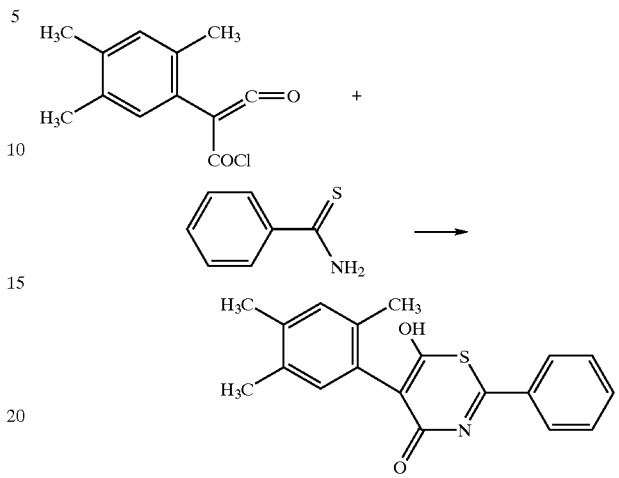

If 3-[(2,5-dichloro-4-methyl)-phenyl]-5,5-dimethyl-pyrrolidine-2,4-dione and pivaloyl chloride are used as starting substances according to process (Fα), the course of the process according to the invention can be represented by the following equation:

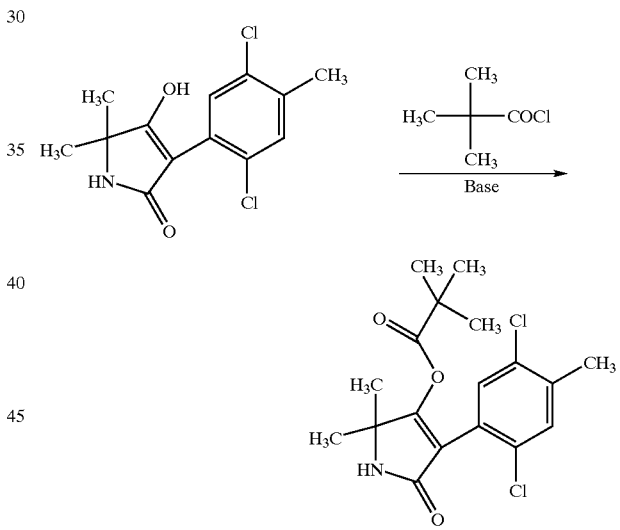

3-[(2,4,5-trichloro)-phenyl]-4-hydroxy-5-phenyl-$\Delta^3$-dihydrofuran-2-one and acetic anhydride are used as starting compounds according to process (F) (variant β), the course of the process according to the invention can be represented by the following equation:

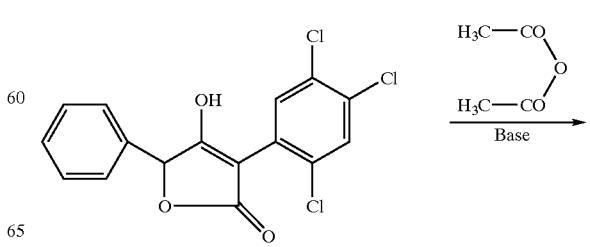

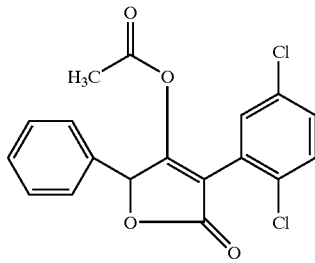

If 8-[(2,4-dichloro-5-methyl)-phenyl]-5,5-pentamethylene-pyrrolidine-2,4-dione and ethoxyethyl chloroformate are used as starting compounds according to process (G), the course of the process according to the invention can be represented by the following equation:

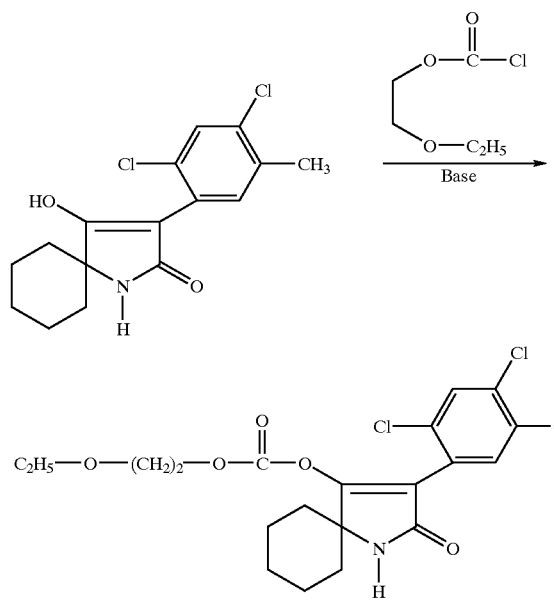

If 3-[(2-bromo-4,5-dimethyl)-phenyl]-4-hydroxy-6-(3-pyridyl)-pyrone and methyl chloromonothioformate are used as starting substances according to process (H) (variant α), the course of the reaction can be represented as follows:

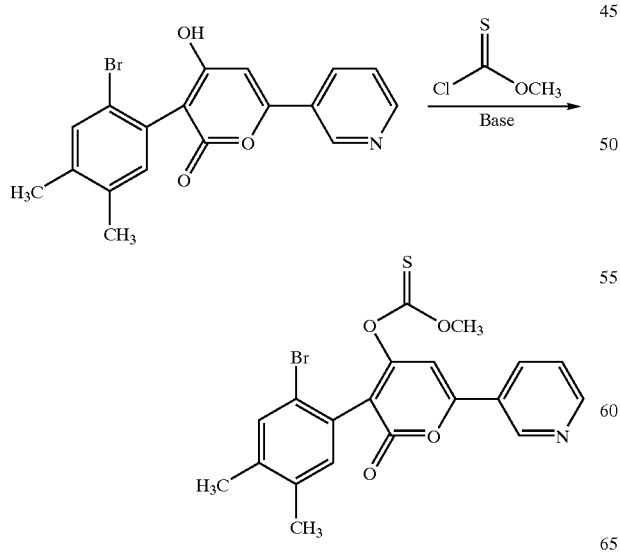

If 5-[(5-chloro-2-fluoro-4-methyl)-phenyl]-6-hydroxy-2-(4-chlorophenyl)-thiazin-4-one, carbon disulphide and methyl iodide are used as starting components according to process (H) (variant β), the course of the reaction can be represented as follows:

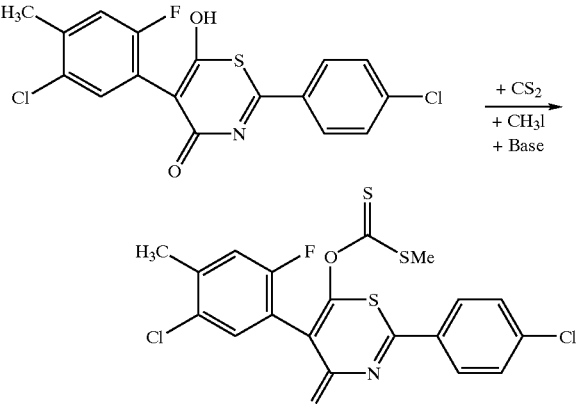

If 2-[(2,4,5-trimethyl)-phenyl]-5,5-[(3-methyl)-pentamethylene]-pyrrolidine-2,4-dione and methanesulphonyl chloride are used as starting substances according to process (I), the course of the reaction can be represented by the following equation:

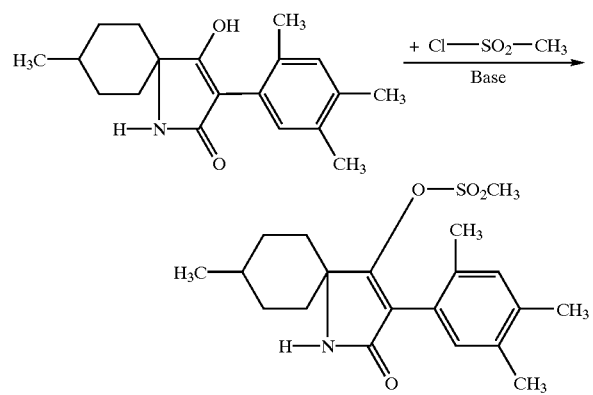

If 2-[(2-chloro-4,5-dimethyl)-phenyl]4-hydroxy-5-methyl-6-(2-pyridyl)-pyrone and methanethio-phosphonic acid chloride 2,2,2-trifluoroethyl ester are used as starting substances according to process (J), the course of the reaction can be represented by the following equation:

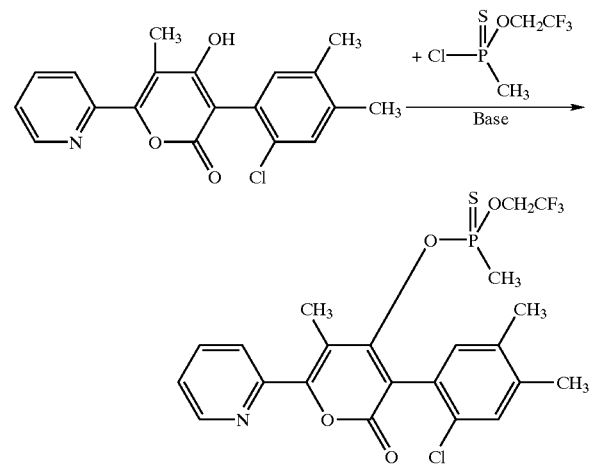

If 3-[(2,4,5-trichloro)-phenyl]-5-cyclopropyl-5-methyl-pyrrolidine-2,4-dione and NaOH are used as components according to process (K), the course of the process according to the invention can be represented by the following equation:

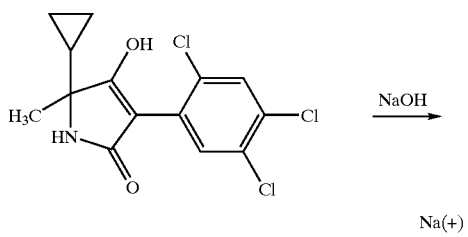

If 3-[(2-chloro-4-bromo-5-methyl)-phenyl]-4-hydroxy-5,5-tetramethylene-Δ³-dihydro-furan-2-one and ethyl isocyanate are used as starting substances according to process (L) (variant α), the course of the reaction can be represented by the following equation:

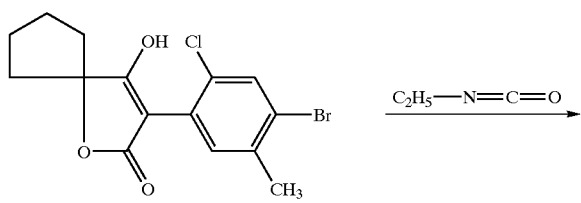

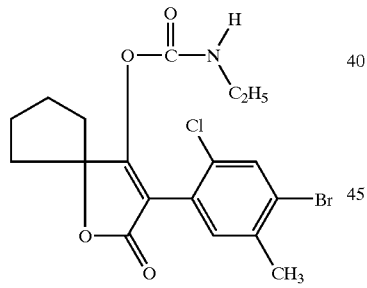

If 3-[(2-chloro-4,5-dimethyl)-phenyl]-5-methyl-pyrrolidine-2,4-dione and dimethylcarbamoyl chloride are used as starting substances according to process (L) (variant β), the course of the reaction can be represented by the following equation:

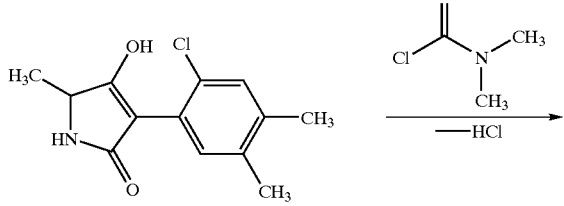

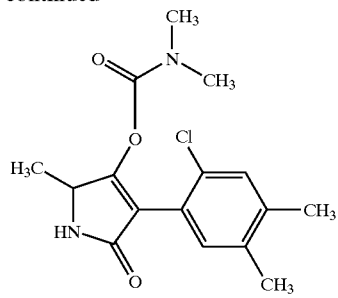

The compounds of the formula (II)

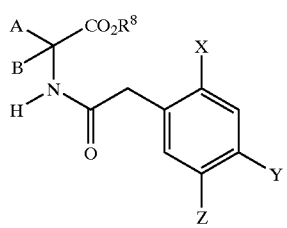

(II)

in which

A, B, X, Y, Z and $R^8$ have the abovementioned meanings, required as starting substances in process (A) according to the invention are new.

The acylamino acid esters of the formula (II) are obtained, for example, when amino acid derivatives of the formula (XIX)

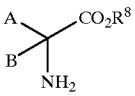

(XIX)

in which

A, B and $R^8$ have the abovementioned meanings, are acylated with substituted phenylacetic acid halides of the formula (XX)

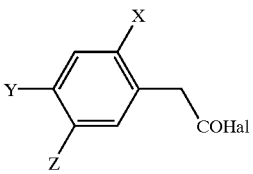

(XX)

in which

X, Y and Z have the abovementioned meanings and

Hal represents chlorine or bromine (Chem. Reviews 52, 237–416 (1953); Bhattacharya, Indian J. Chem. 6 341–5, 1968)

or when acylamino acids of the formula (XXI)

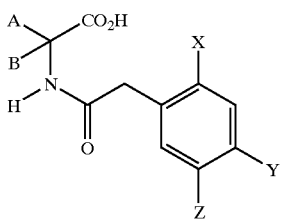
(XXI)

in which

A, B, X, Y and Z have the abovementioned meanings,
are esterified (Chem. Ind. (London) 1568 (1968)).

The compounds of the formula (XXI)

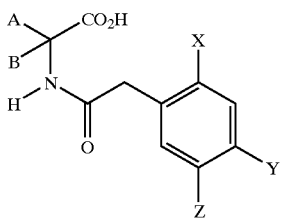
(XXI)

in which

A, B, X, Y and Z have the abovementioned meanings,
are new.

The compounds of the formula (XXI) are obtained when amino acids of the formula (XXII)

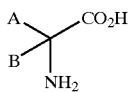
(XXII)

in which

A and B have the abovementioned meanings,
are acylated with substituted phenylacetic acid halides of the formula (XX)

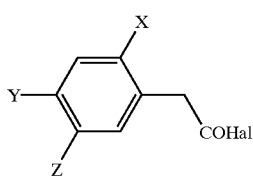
(XX)

in which

X, Y and Z have the abovementioned meanings and

Hal represents chlorine or bromine,
in a Schotten-Baumann reaction (Organikum, VEB Deutscher Verlag der Wissenschaften, Berlin 1977, page 505).

The compounds of the formula (XX) are new in some cases and they can be prepared by known processes.

The compounds of the formula (XX) are obtained, for example, by a procedure in which substituted phenylacetic acids of the formula (XXII)

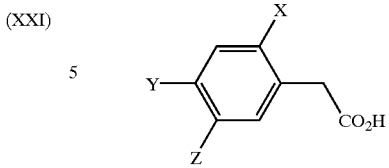
(XXIII)

in which

X, Y and Z have the abovementioned meaning,
are reacted with halogenating agents (for example thionyl chloride, thionyl bromide, oxalyl chloride, phosgene, phosphorus trichloride; phosphorus tribromide or phosphorus pentachloride), if appropriate in the presence of a diluent (for example optionally chlorinated aliphatic or: aromatic hydrocarbons, such as toluene or methylene chloride), at temperatures from –20° C. to 150° C., preferably from –10° C. to 100° C.

The compounds of the formula (XXIII) are new in some cases, and they can be preapred by processes known from the literature (Organikum 15th edition, page 533, VEB Deutscher Verlag der Wissenschaften, Berlin 1977). The compounds of the formula (XXIII) are obtained, for example, by a procedure in which substituted phenylacetic acid esters of the formula (XXIV)

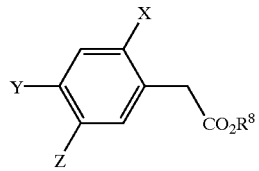
(XXIV)

in which

X, Y, Z and $R^8$ have the abovementioned meaning,
are hydrolysed in the presence of an acid (for example an inorganic acid, such as hydrochloric acid) or a base (for example an alkali metal hydroxide, such as sodium hydroxide or potassium hydroxide) and if appropriate a diluent (for example an aqueous alcohol, such as methanol or ethanol) at temperatures between 0° C. and 150° C., preferably between 20° C. and 100° C.

The compounds of the formula (XXIV) are new in some cases and they can be prepared by processes which are known in principle.

The compounds of the formula (XXIV) are obtained, for example, by a procedure in which substituted 1,1,1-trichloro-2-phenylethanes of the formula (XXV)

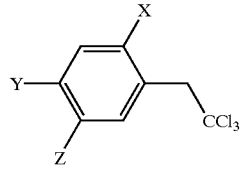
(XXV)

in which

X, Y and Z have the abovementioned meaning,
are reacted first with alcoholates (for example alkali metal alcoholates, such as sodium methylate or sodium ethylate) in the presence of a diluent (for example the alcohol derived from the alcoholate) at temperatures between 0° C. and 150°

C., preferably between 20° C. and 120° C., and then with an acid (preferably an inorganic acid, such as, for example, sulphuric acid) at temperatures between −20° C. and 150° C., preferably 0° C. and 100° C. (cf. DE 3 314 249).

The compounds of the formula (XXV) are new in some cases and they can be prepared by processes which are known in principle.

The compounds of the formula (XXV) are obtained, for example, when anilines of the formula (XXVI)

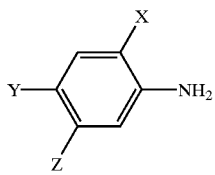

(XXVI)

in which

X, Y and Z have the abovementioned meaning,
are reacted with vinylidene chloride (CH$_2$=CCl$_2$) in the presence of an alkyl nitrite of the formula (XXVII)

R$^{21}$—ONO (XXVII)

in which

R$^{21}$ represents alkyl, preferably C$_1$–C$_6$-alkyl,
in the presence of copper(II) chloride and if appropriate in the presence of a diluent (for example an aliphatic nitrile, such as acetonitrile), at a temperature of −20° C. to 80° C., preferably 0° C. to 60° C.

The compounds of the formula (XXVI) and (XXVII) are known compounds of organic chemistry. Copper(II) chloride and vinylidene chloride have been known and commercially obtainable for a long time.

The compounds of the formula (XIX) and (XXII) are known in some cases and/or they can be prepared by known processes (see, for example, Compagnon, Miocque Ann. Chim. (Paris) [14] 5, pages 11–22, 23–27 (1970)).

The substituted cyclic aminocarboxylic acids of the formula (XXIIa) in which A and B form a ring are in general obtainable by the Bucherer-Bergs synthesis or by the Strecker synthesis and are in each case obtained in these syntheses in different isomer forms. Thus, under the conditions of the Bucherer-Bergs synthesis, the isomers (for simplicity called β below) in which the radicals R and the carboxyl group are equatorial are predominantly obtained, while under the conditions of the Strecker synthesis the isomers (for simplicity called α below) in which the amino group and the radicals R are equatorial are predominantly obtained.

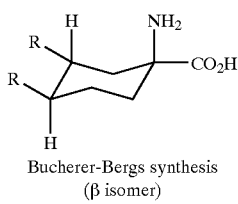

Bucherer-Bergs synthesis
(β isomer)

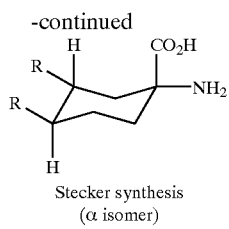

Stecker synthesis
(α isomer)

(L. Munday, J. Chem. Soc. 4372 (1961); J. T. Eward, C. Jitrangeri, Can. J. Chem. 53, 3339 (1975)).

Furthermore, the starting substances of the formula (II)

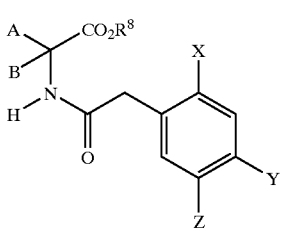

(II)

in which

A, B, X, Y, Z and R$^8$ have the abovementioned meanings,
used in the above process (A) can be prepared when aminonitriles of the formula (XXVIII)

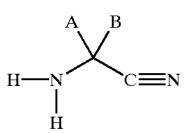

(XXVIII)

in which

A and B have the abovementioned meanings,
are reacted with substituted phenylacetic acid halides of the formula (XX)

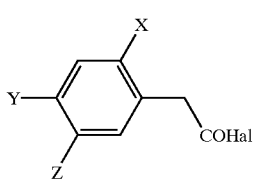

(XX)

in which

X, Y, Z and H have the abovementioned meanings,
to give compounds of the formula (XXIX)

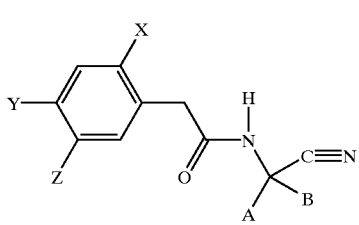

(XXIX)

in which

A, B, X, Y and Z have the abovementioned meanings,
and these are then subjected to acid alcoholysis.

The compounds of the formula (XXIX) are likewise new.
The compounds of the formula (III)

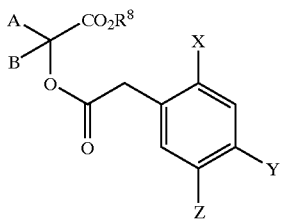 (III)

in which

A, B. X, Y, Z and $R^8$ have the abovementioned meanings,
required as starting substances in process (B) according to the invention are new.

They can be prepared in a simple manner by methods which are known in principle.

The compounds of the formula (III) are obtained, for example, when 2-hydroxycarboxylic acid esters of the formula (XXX)

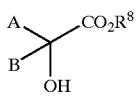 (XXX)

in which

A, B and $R^8$ have the abovementioned meanings,
are acylated with substituted phenylacetic acid halides of the formula (XX)

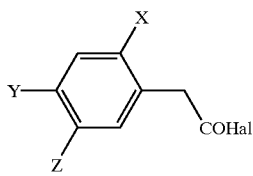 (XX)

in which

X, Y, Z and Hal have the abovementioned meanings (Chem. Reviews 52, 237–416 (1953)).

Compounds of the formula (III) are furthermore obtained when substituted phenylacetic acids of the formula (XXIII)

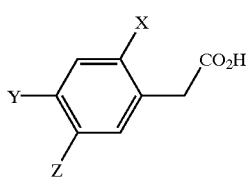 (XXIII)

in which

X, Y and Z have the abovementioned meanings,
are alkylated with α-halogenocarboxylic acid esters of the formula (XXXI)

 (XXXI)

in which

A, B and $R^8$ have the abovementioned meanings and
Hal represents chlorine or bromine.

The compounds of the formula (XXXI) are commercially obtainable.

The compounds of the formula (IV)

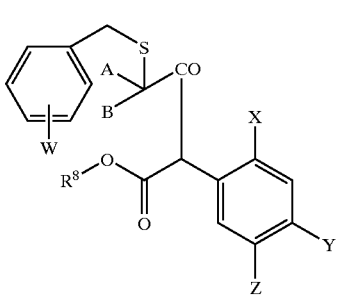 (IV)

in which

A, B, W, X, Y, Z and $R^8$ have the abovementioned meanings, required as starting substances in the above process (C) are new.

They can be prepared by methods which are known in principle.

The compounds of the formula (IV) are obtained, for example, when substituted phenylacetic acid esters of the formula (XXIV)

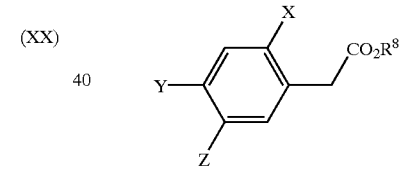 (XXIV)

in which

X, Y, $R^8$ and Z have the abovementioned meanings,
are acylated with 2-benzylthio-carboxylic acid halides of the formula (XXXII)

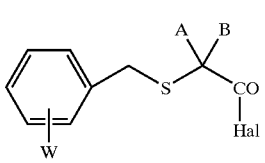 (XXXII)

in which

A, B and W have the abovementioned meanings and
Hal represents halogen (in particular chlorine or bromine),
in the presence of strong bases (see, for example, M. S. Chambers, E. J. Thomas, D. J. Williams, J. Chem. Soc. Chem. Commun., (1987), 1228).

The benzylthio-carboxylic acid halides of the formula (XXXII) are known in some cases and/or they can be prepared by known processes (J. Antibiotics (1983), 26, 1589).

The halogenocarbonylketenes of the formula (VI) required as starting substances in process (D) are new. They can be prepared in a simple manner by methods which are known in principle (cf., for example, Org. Prep. Proced. Int., 7, (4), 155–158, 1975 and DE 1 945 703). The compounds of the formula (VI)

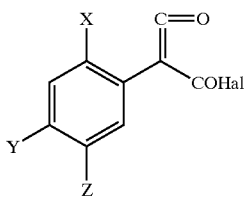

(VI)

in which

X, Y and Z have the abovementioned meanings and

Hal represents chlorine or bromine, are obtained when substituted phenylmalonic acids of the formula (XXXII)

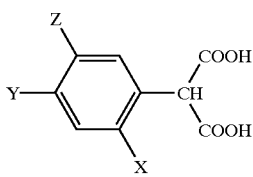

(XXXIII)

in which

X, Y and Z have the abovementioned meanings, are reacted with acid halides, such as, for example, thionyl chloride, phosphorus(V) chloride, phosphorus(III) chloride, oxalyl chloride, phosgene or thionyl bromide, if appropriate in the presence of catalysts, such as, for example, diethylformamide, methyl-stearylformamide or triphenylphosphine, and if appropriate in the presence of bases, such as, for example, pyridine or triethylamine, at a temperature between −20° C. and 200° C., preferably between 0° C. and 150° C.

The substituted phenylmalonic acids of the formula (XXXIII) are new. However, they can be prepared in a simple manner by known processes (cf., for example, Organikum, VEB Deutscher Verlag der Wissenschaften, Berlin 1977, page 517 et seq.), for example from substituted phenylmalonic acid esters of the formula (XXXIV)

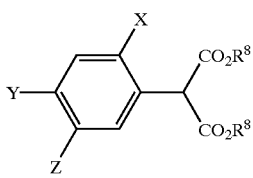

(XXXIV)

in which

X, Y, Z and $R^8$ have the abovementioned meaning, by hydrolysis.

The carbonyl compounds of the formula (V) or silylenol ethers thereof of the formula (Va)

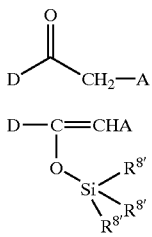

(V)

(Va)

in which

A, D and $R^{8'}$ have the abovementioned meanings, required as starting substances for process (E) according to the invention are commercially obtainable compounds which are generally known or accessible by known processes.

The preparation of the ketene acid chlorides of the formula (VI) required as starting substances for carrying out process (E) according to the invention has already been described in the case of process (D) according to the invention. The thioamides of the formula (VII)

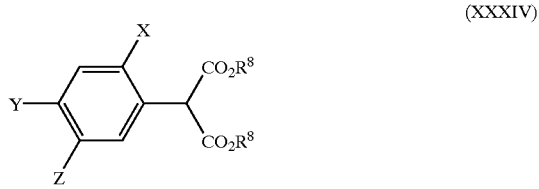

(VII)

in which

A has the abovementioned meaning, required for carrying out process (E) according to the invention are compounds which are generally known in organic chemistry.

The malonic acid esters of the formula (XXXIV)

(XXXIV)

in which $R^8$, X, Y and Z have the abovementioned meanings, are new and can be prepared by generally known methods of organic chemistry (cf., for example, Tetrahedron Lett. 27, 2763(1986) and Organikum VEB Deutscher Verlag der Wissenschaften, Berlin 1977, page 587 et seq.).

The acid halides of the formula (VIII), carboxylic acid anhydrides of the formula (IX), chloroformic acid esters or chloroformic acid thioesters of the formula (X), chloromonothioformic acid esters or chlorodithioformic acid esters of the formula (XI), alkyl halides of the formula (XII), sulphonic acid chlorides of the formula (XIII), phosphorus compounds of the formula (XIV) and metal hydroxides, metal alkoxides or amines of the formula (XV) and (XVI) and isocyanates of the formula (XVII) and carbamic acid chlorides of the formula (XVIII) furthermore required as starting substances for carrying out processes (F), (G), (H), (I), (J), (K) and (L) according to the invention are generally known compounds of organic or inorganic chemistry.

The compounds of the formulae (V), (VII) to (XVIII), (XIX), (XXII), (XXVIII), (XXX), (XXXI), (XXXII), (XXXIII) and (XXXIV) are furthermore known from the patent applications cited above and/or can be prepared by the methods mentioned therein.

Process (A) is characterized in that compounds of the formula (II) in which A, B, X, Y, Z and $R^8$ have the abovementioned meanings are subjected to intramolecular condensation in the presence of a diluent and in the presence of a base.

Diluents which can be employed in process (A) according to the invention are all the organic solvents which are inert towards the reaction participants. Solvents which can preferably be used are hydrocarbons, such as toluene and xylene, and furthermore ethers, such as dibutyl ether, tetrahydrofuran, dioxane, glycol dimethyl ether and diglycol dimethyl ether, and also polar solvents, such as dimethyl sulphoxide, sulpholane, dimethylformamide and N-methyl-pyrrolidone, as well as alcohols, such as methanol, ethanol, propanol, iso-propanol, butanol, iso-butanol and tert-butanol.

All the customary proton acceptors can be employed as the base (deprotonating agent) in carrying out process (A) according to the invention. Proton acceptors which can preferably be used are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). Alkali metals, such as sodium or potassium, can moreover be used. Alkali metal and alkaline earth metal amides and hydrides, such as sodium amide, sodium hydride and calcium hydride, and in addition also alkali metal alcoholates, such as sodium methylate, sodium ethylate and potassium tert-butylate, can furthermore be employed.

The reaction temperature can be varied within a substantial range when carrying out process (A) according to the invention. The reaction is in general carried out at temperatures between 0° C. and 250° C., preferably between 50° C. and 150° C.

Process (A) according to the invention is in general carried out under normal pressure.

In carrying out process (A) according to the invention, the reaction component of the formula (II) and the deprotonating base are in general employed in equimolar to about twice the equimolar amounts. However, it is also possible to use one or other of the components in a larger excess (up to 3 mol).

Process (B) is characterized in that compounds of the formula (III) in which A, B, X, Y, Z and $R^8$ have the abovementioned meanings are subjected to intramolecular condensation in the presence of a diluent and in the presence of a base.

Diluents which can be employed in process (B) according to the invention are all the organic solvents which are inert towards the reaction participants. Solvents which can preferably be used are hydrocarbons, such as toluene and xylene, and furthermore ethers, such as dibutyl ether, tetrahydrofuran, dioxane, glycol dimethyl ether and diglycol dimethyl ether, and also polar solvents, such as dimethyl sulphoxide, sulpholane, dimethylformamide and N-methyl-pyrrolidone. Alcohols, such as methanol, ethanol, propanol, iso-propanol, butanol, iso-butanol and tert-butanol, can furthermore be employed.

All the customary proton acceptors can be employed as the base (deprotonating agent) in carrying out process (B) according to the invention. Proton acceptors which can preferably be used are alkali metal and alkaline earth metal oxides, hydroxides and carbonates, such as sodium hydroxide, potassium hydroxide, magnesium oxide, calcium oxide, sodium carbonate,, potassium carbonate and calcium carbonate, which can also be employed in the presence of phase transfer catalysts, such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). Alkali metals, such as sodium or potassium, can moreover be used. Alkali metal and alkaline earth metal amides and hydrides, such as sodium amide, sodium hydride and calcium hydride, and in addition also alkali metal alcoholates, such as sodium methylate, sodium ethylate and potassium tert-butylate, can furthermore be employed.

The reaction temperature can be varied within a substantial range when carrying out process (B) according to the invention. The reaction Is in general carried out at temperatures between 0° C. and 250° C., preferably between 50° C. and 150° C.

Process (B) according to the invention is in general carried out under normal pressure.

In carrying out process (B) according to the invention, the reaction components of the formula (III) and the deprotonating bases are in general employed in approximately equimolar amounts. However, it is also possible to use one or other of the components in a larger excess (up to 3 mol).

Process (C) is characterized in that compounds of the formula (IV) in which A, B, W, X, Y, Z and $R^8$ have the abovementioned meaning are subjected to intramolecular cyclization in the presence of an acid and if appropriate in the presence of a diluent.

Diluents which can be employed in process (C) according to the invention are all the organic solvents which are inert towards the reaction participants. Solvents which can preferably be used are hydrocarbons, such as toluene and xylene, and furthermore halogenated hydrocarbons, such as methylene chloride, chloroform, ethylene chloride, chlorobenzene and dichlorobenzene, and also polar solvents, such as dimethyl sulphoxide, sulpholane, dimethylformamide and N-methyl-pyrrolidone. Alcohols, such as methanol, ethanol, propanol, iso-propanol, butanol, iso-butanol and tert-butanol, can furthermore be employed.

If appropriate, the acid employed can also serve as the diluent.

Acids which can be employed in process (C) according to the invention are all the customary inorganic and organic acids, such as, for example, hydrogen halide acids, sulphuric acid and alkyl-, aryl- and haloalkylsulphonic acids, and halogenated alkylcarboxylic acids, such as, for example, trifluoroacetic acid, are used in particular.

The reaction temperature can be varied within a substantial range in carrying out process (C) according to the invention. The reaction is in general carried out at temperatures between 0° C. and 250° C., preferably between 5° C. and 150° C.

Process (C) according to the invention is in general carried out under normal pressure.

In carrying out process (C) according to the invention, the reaction components of the formula (IV) and the acid are employed, for example, in equimolar amounts. Where appropriate, however, it is also possible to employ the acid in catalytic amounts.

Process (D) according to the invention is characterized in that carbonyl compounds of the formula (V) or silylenol ethers thereof of the formula (Va) are reacted with ketene acid halides of the formula (VI), if appropriate in the presence of a diluent and if appropriate in the presence of an acid acceptor.

Diluents which can be employed in process (D) according to the invention are all the organic solvents which are inert towards the reaction participants. Solvents which can preferably be used are hydrocarbons, such as o-dichlorobenzene, tetralin, toluene and xylene, and furthermore ethers, such as dibutyl ether, glycol dimethyl ether and diglycol dimethyl ether, and also polar solvents, such as dimethyl sulphoxide, sulpholane, dimethylformamide or N-methyl-pyrrolidone.

All the customary acid acceptors can be used as acid acceptors in carrying out process (D) according to the invention.

Acid acceptors which can preferably be used are tertiary amines, such as triethylamine, pyridine, diazabicyclooctane (DABCO), diazabicycloundecene (DBU), diazabicyclononene (DBN), Hunig base or N,N-dimethyl-aniline.

The reaction temperature can be varied within a substantial range in carrying out process (D) according to the invention. The reaction is expediently carried out at temperatures between 0C and 250° C., preferably between 50° C. and 220° C.

Process (D) according to the invention is preferably carried out under normal pressure.

In carrying out process (D) according to the invention, the reaction components of the formulae (V) and (VI) and if appropriate the acid acceptor are in general employed in approximately equimolar amounts. However, it is also possible to use one or other of the components in a larger excess (up to 5 mol).

Process (E) according to the invention is characterized in that thioamides of the formula (VII) are reacted with ketene acid halides of the formula (VI), if appropriate in the presence of a diluent and if appropriate in the presence of an acid acceptor.

Diluents which can be employed in process variant (E) according to the invention are all the inert organic solvents. Solvents which can preferably be used are hydrocarbons, such as o-dichlorobenzene, tetralin, toluene and xylene, and furthermore ethers, such as dibutyl ether, glycol dimethyl ether and diglycol dimethyl ether, and also polar solvents, such as dimethyl sulphoxide, sulpholane, dimethylformamide and N-methyl-pyrrolidone.

All the customary acid acceptors can be used as acid acceptors in carrying out process (E) according to the invention.

Acid acceptors which can preferably be used are tertiary amines, such as triethylamine, pyridine, diazabicyclooctane (DABCO), diazabicycloundecene (DBU), diazabicyclononene (DBN), Hunig base or N,N-dimethyl-aniline.

The reaction temperature can be varied within a substantial range in carrying out process (E) according to the invention. The reaction is expediently carried out at temperatures between 0° C. and 250° C., preferably between 20° C. and 220° C.

Process (E) according to the invention is expediently carried out under normal pressure.

In carrying out process (E) according to the invention, the reaction components of the formulae (VII) and (VI) and if appropriate the acid acceptors are in general employed in approximately equimolar amounts. However, it is also possible to use one or other of the components in a larger excess (up to 5 mol).

Process (Fα) is characterized in that compounds of the formulae (I-1-a) to (I-5-a) are in each case reacted with carboxylic acid halides of the formula (VIII), if appropriate in the presence of a diluent and if appropriate in the presence of an acid-binding agent.

Diluents which can be employed in process (Fα) according to the invention are all the solvents which are inert towards the acid halides. Solvents which can preferably be used are hydrocarbons, such as benzine, benzene, toluene, xylene and tetralin, and furthermore halogenated hydrocarbons, such as methylene chloride, chloroform, carbon tetrachloride, chlorobenzene and o-dichlorobenzene, and also ketones, such as acetone and methyl isopropyl ketone, and furthermore ethers, such as diethyl ether, tetrahydrofuran and dioxane, and moreover carboxylic acid esters, such as ethyl acetate, and also strongly polar solvents, such as dimethylformamide, dimethyl sulphoxide and sulpholane. If the stability of the acid halide to hydrolysis allows, the reaction can also be carried out in the presence of water.

Possible acid-binding agents in the reaction by process (Fα) according to the invention are all the customary acid acceptors. Acid acceptors which can preferably be used are tertiary amines, such as triethylamine, pyridine, diazabicyclooctane (DABCO), diazabicycloundecene (DBU), diazabicyclononene (DBN), Hünig base and N,N-dimethyl-aniline, and furthermore alkaline earth metal oxides, such as magnesium oxide and calcium oxide, and also alkali metal and alkaline earth metal carbonates, such as sodium carbonate, potassium carbonate and calcium carbonate, as well as alkali metal hydroxides, such as sodium hydroxide and potassium hydroxide.

The reaction temperature can be varied within a substantial range in process (Fα) according to the invention. The reaction is in general carried out at temperatures between −20° C. and +150° C., preferably between 0° C. and 100° C.

In carrying out process (Fα) according to the invention, the starting substances of the formulae (I-1-a) to (I-5-a) and the carboxylic acid halide of the formula (VIII) are in general used in amounts which are in each case approaching equivalent amounts. However, it is also possible to employ the carboxylic acid halide in a larger excess (up to 5 mol). Working up is carried out by customary methods.

Process (Fβ) is characterized in that compounds of the formulae (I-1-a) to (I-5-a) are in each case reacted with carboxylic acid anhydrides of the formula (IX), if appropriate in the presence of a diluent and if appropriate in the presence of an acid-binding agent.

Diluents which can be used in process (Fβ) according to the invention are preferably those diluents which are also preferably possible in the case where acid halides are used. A carboxylic acid anhydride employed in excess can moreover also simultaneously function as the diluent.

Possible acid-binding agents which are added, if appropriate, in process (Fβ) are preferably those acid-binding agents which are also preferably possible when acid halides are used.

The reaction temperature can be varied within a substantial range in process (Fβ) according to the invention. The reaction is in general carried out at temperatures between −20° C. and +150° C., preferably between 0° C. and 100° C.

In carrying out process (Fβ) according to the invention, the starting substances of the formulae (I-1-a) to (I-5-a) and the carboxylic acid anhydride of the formula (IX) are in general used in amounts which are in each case approaching equivalent amounts. However, it is also possible to employ the carboxylic acid anhydride in a larger excess (up to 5 mol). Working up is carried out by customary methods.

In general, a procedure is followed in which the diluent and the carboxylic acid anhydride present in excess as well as the carboxylic acid formed are removed by distillation or by washing with an organic solvent or with water.

Process (G) is characterized in that compounds of the formulae (I-1-a) to (I-5-a) are in each case reacted with chloroformic acid esters or chloroformic acid thioesters of the formula (X), if appropriate in the presence of a diluent and if appropriate in the presence of an acid-binding agent.

Possible acid-binding agents in process (G) according to the invention are all the customary acid acceptors. Acid acceptors which can preferably be used are tertiary amines, such as triethylamine, pyridine, DABCO, DBU, DBA, Hunig base and N,N-dimethyl-aniline, and furthermore alkaline earth metal oxides, such as magnesium oxide and calcium oxide, and also alkali metal and alkaline earth metal carbonates, such as sodium carbonate, potassium carbonate and calcium carbonate, as well as alkali metal hydroxides, such as sodium hydroxide and potassium hydroxide.

Diluents which can be employed in process (G) according to the invention are all the solvents which are inert towards the chloroformic acid esters or chloroformic acid thioesters. Solvents which can preferably be used are hydrocarbons, such as benzine, benzene, toluene, xylene and tetralin, and furthermore halogenated hydrocarbons, such as methylene chloride, chloroform, carbon tetrachloride, chlorobenzene and o-dichlorobenzene, and also ketones, such as acetone and methyl isopropyl ketone, and moreover ethers, such as diethyl ether, tetrahydrofuran and dioxane, and furthermore carboxylic acid esters, such as ethyl acetate, and also nitrites, such as acetonitrile, as well as strongly polar solvents, such as dimethylformamide, dimethyl sulphoxide and sulpholane.

The reaction temperature can be varied within a substantial range in carrying out process (G) according to the invention. The reaction temperature is in general between −20° C. and +100° C., preferably between 0° C. and 50° C.

Process (G) according to the invention is in general carried out under normal pressure.

In carrying out process (G) according to the invention, the starting substances of the formulae (I-1-a) to (I-5-a) and the corresponding chloroformic acid esters or chloroformic acid thioesters of the formula (X) are in general used in amounts which are in each case approaching equivalent amounts. However, it is also possible to employ one or other of the components in a larger excess (up to 2 mol). Working up is carried out by customary methods. A procedure is in general followed in which, salts which have precipitated out are removed and the reaction mixture which remains is concentrated by stripping off the diluent.

Process (H) according to the invention is characterized in that compounds of the formulae (I-1-a) to (I-5-a) are in each case reacted with (Hα) compounds of the formula (XI) in the presence of a diluent and if appropriate in the presence of an acid-binding agent, or (Hβ) carbon disulphide and then with alkyl halides of the formula (XII), if appropriate in the presence of a diluent and if appropriate in the presence of a base.

In preparation process (Hα), about 1 mol of chloromonothioformic acid ester or chlorodithioformic acid ester of the formula (XI) is reacted per mol of starting compound of the formulae (I-1-a) to (I-5-a) at 0 to 120° C., preferably at 20 to 60° C.

Possible diluents which are added, if appropriate, are all the inert polar organic solvents, such as ethers, amides, sulphones, sulphoxides and also halogenoalkanes.

Dimethyl sulphoxide, tetrahydrofuran, dimethylformamide or methylene chloride are preferably employed.

If the enolate salt of the compounds (I-1-a) to (I-5-a) is prepared in a preferred embodiment by addition of strong deprotonating agents, such as, for example, sodium hydride or potassium tert-butylate, further addition of acid-binding agents can be omitted.

If acid-binding agents are employed, then customary inorganic or organic bases are possible, and examples which may be mentioned are sodium hydroxide, sodium carbonate, potassium carbonate, pyridine and triethylamine.

The reaction can be carried out under normal pressure or under increased pressure, and is preferably carried out under normal pressure. Working up is carried out by customary methods.

In preparation process (Hβ), in each case the equimolar amount or an excess of carbon disulphide is added per mol of starting compounds of the formulae (I-1-a) to (I-5-a). The reaction here is preferably carried out at temperatures from 0 to 50° C., and in particular at 20 to 30° C.

It is often expedient first to prepare the corresponding salt from the compounds of the formulae (I-1-a) to (I-5-a) by addition of a base (such as, for example, potassium tert-butylate or sodium hydride). The compounds (I-1-a) to (I-5-a) are in each case reacted with carbon disulphide until the formation of the intermediate compound has ended, for example after stirring at room temperature for several hours.

All the customary proton acceptors can be employed as bases in process (Hβ). Proton acceptors which can preferably be used are alkali metal hydrides, alkali metal alcoholates, alkali metal or alkaline earth metal carbonates or bicarbonates or nitrogen bases. Examples which may be mentioned are sodium hydride, sodium methanolate, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

All the customary solvents can be used as diluents in this process.

Solvents which can preferably be used are aromatic hydrocarbons, such as benzene or toluene, alcohols, such as methanol, ethanol, isopropanol or ethylene glycol, nitrites, such as acetonitrile, ethers, such as tetrahydrofuran or dioxane, amides, such as dimethylformamide, or other polar solvents, such as dimethyl sulphoxide or sulpholane.

Further reaction with the alkyl halide of the formula (XII) is preferably carried out at 0 to 70° C., and in particular at 20 to 50° C. At least the equimolar amount of alkyl halide is employed in this reaction.

The reaction is carried out under normal pressure or under increased pressure, preferably under normal pressure.

Working up is again carried out by customary methods.

Process (I) according to the invention is characterized in that compounds of the formulae (I-1-a) to (I-5-a) are in each case reacted with sulphonic acid chlorides of the formula (XIII), if appropriate in the presence of a diluent and if appropriate in the presence of an acid-binding agent.

In preparation process (I), about 1 mol of sulphonic acid chloride of the formula (XIII) is reacted per mol of starting compound of the formula (I-1-a to I-5-a) at −20 to 150° C., preferably at 0 to 70° C.

Process (I) is preferably carried out in the presence of a diluent.

Possible diluents are all the inert polar organic solvents, such as ethers, amides, ketones, carboxylic acid esters, nitrites, sulphones, sulphoxides or halogenated hydrocarbons, such as methylene chloride.

Dimethyl sulphoxide, tetrahydrofuran, dimethylformamide and methylene chloride are preferably employed.

If the enolate salt of the compounds (I-1-a) to (I-5-a) is prepared in a preferred embodiment by addition of strong deprotonating agents (such as, for example, sodium hydride or potassium tert-butylate), further addition of acid-binding agents can be omitted.

If acid-binding agents are employed, then customary inorganic or organic bases are possible, and examples which may be mentioned are sodium hydroxide, sodium carbonate, potassium carbonate, pyridine and triethylamine.

The reaction can be carried out under normal pressure or under increased pressure, and is preferably carried out under normal pressure. Working up is carried out by customary methods.

Process (J) according to the invention is characterized in that compounds of the formulae (I-1-a) to (I-5-a) are in each case reacted with phosphorus compounds of the formula (XIV), if appropriate in the presence of a diluent and if appropriate in the presence of an acid-binding agent.

In preparation process (J), 1 to 2, preferably 1 to 1.3, mol of the phosphorus compound of the formula (XIV) are reacted per mol of the compounds (I-1-a) to (I-5-a) at temperatures between $-40°$ C. and $150°$ C., preferably between $-10$ and $110°$ C., to give compounds of the formulae (I-1-e) to (I-6-e).

Process (J) is preferably carried out in the presence of a diluent.

Possible diluents are all the inert polar organic solvents, such as ethers, carboxylic acid esters, halogenated hydrocarbons, ketones, amides, nitrites, sulphones, sulphoxides and the like.

Acetonitrile, dimethyl sulphoxide, tetrahydrofuran, dimethylformamide and methylene chloride are preferably employed.

Possible acid-binding agents, which are added if appropriate, are the customary inorganic or organic bases, such as hydroxides, carbonates or amines. Examples which may be mentioned are sodium hydroxide, sodium carbonate, potassium carbonate, pyridine and triethylamine.

The reaction can be carried out under normal pressure or under increased pressure, and is preferably carried out under normal pressure. Working up is carried out by customary methods of organic chemistry. The end products are preferably purified by crystallization, chromatographic purification or by so-called "incipient distillation", i.e. removal of the volatile constituents in vacuo.

Process (K) is characterized in that compounds of the formulae (I-1-a) to (I-5-a) are in each case reacted with metal hydroxides or metal alkoxides of the formula (XV) or amines of the formula (XVI), if appropriate in the presence of a diluent.

Diluents which can be employed in process (K) according to the invention are preferably ethers, such as tetrahydrofuran, dioxane or diethyl ether, or else alcohols, such as methanol, ethanol or isopropanol, or alternatively water. Process (K) according to the invention is in general carried out under normal pressure. The reaction temperature is in general between $-20°$ C. and $100°$ C., preferably between $0°$ C. and $50°$ C.

Process (L) according to the invention is characterized in that compounds of the formulae (I-1-a) to (I-5-a) are in each case reacted with (Lα) compounds of the formula (XVII), if appropriate in the presence of a diluent and if appropriate in the presence of a catalyst, or with (Lβ) compounds of the formula (XVIII) if appropriate in the presence of a diluent and if appropriate in the presence of an acid-binding agent.

In preparation process (Lα), about 1 mol of isocyanate of the formula (XVII) is reacted per mol of starting compound of the formulae (I-1-a) to (I-5-a) at 0 to $100°$ C., preferably at 20 to $50°$ C.

Process (Lα) is preferably carried out in the presence of a diluent.

Possible diluents are all the inert organic solvents, such as aromatic hydrocarbons, halogenated hydrocarbons, ethers, amides, nitrites, sulphones or sulphoxides.

If appropriate, catalysts can be added to accelerate the reaction. Catalysts which can very advantageously be employed are organotin compounds, such as, for example, dibutyltin dilaurate.

The reaction is preferably carried out under normal pressure.

In preparation process (Lβ), about 1 mol of carbamic acid chloride of the formula (XVIII) is reacted per mol of starting compound of the formulae (I-1-a) to (I-5-a) at 0 to $150°$ C., preferably at 20 to $70°$ C.

Possible diluents, which are added if appropriate, are all the inert polar organic solvents, such as ethers, carboxylic acid esters, nitrites, ketones, amides, sulphones, sulphoxides or halogenated hydrocarbons.

Dimethyl sulphoxide, tetrahydrofuran, dimethylformamide or methylene chloride are preferably employed.

If the enolate salt of the compound (I-1-a) to (I-5-a) is prepared in a preferred embodiment by addition of strong deprotonating agents (such as, for example, sodium hydride or potassium tert-butylate), further addition of acid-binding agents can be omitted.

If acid-binding agents are employed, customary inorganic or organic bases are possible, and examples which may be mentioned are sodium hydroxide, sodium carbonate, potassium carbonate, triethylamine or pyridine.

The reaction can be carried out under normal pressure or under increased pressure, and is preferably carried out under normal pressure. Working up is carried out by customary methods.

The active compounds are suitable for controlling animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dernaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon soistitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Omithodoros sppw, *Dermanyssus gallinae, Ebrophyes ribis, Phyllocoptruta oleivora,* Boophilus spp., Rhipicephalus spp., Amblyomma spp., Hyalomma spp., Ixodes spp., Psoroptes spp., Chorioptes sppw, Sarcoptes spp., Tarsonemus sppt, *Bryobia praetiosa,* Panonychus spp. and Tetranychus spp.

The active compounds according to the invention are distinguished by a high insecticidal and acaricidal activity.

They can be employed particularly successfully against insects which are harmful to plants, such as, for example, against the larvae of the mustard beetle (*Phaedon cochleariae*) or against the larvae of the rice green leafhopper (*Nephotetfix cincticeps*) and against the larvae of the cabbage moth (*Plutella maculipennis*).

The active compounds according to the invention can furthermore be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The dosages of the active compounds according to the invention necessary for combating weeds are between 0.001 and 10 kg/ha, preferably between 0.005 and 5 kg/ha.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop fields, on ornamental and sports lawns and meadow areas and for the selective combating of weeds in annual cultures.

The active compounds according to the invention are particularly suitable for selectively combating monocotyledon weeds in dicotyledon crops by the pre- and post-emergence method. For example, they can be employed very successfully for combating harmful grasses in cotton or sugar beet.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example, ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example, non-ionic and anionic emulsifiers, such as polyoxyethylene fatty acid esters, polyoxyethylene fatty alcohol ethers, for example alkylaryl polyglycol ethers, alkyl sulphonates, alkyl sulphates, aryl sulphonates as well as albumen hydrolysis products; as dispersing agents there are suitable: for example, lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms prepared from these formulations as a mixture with other active compounds, such as insecticides, baits, sterilizing agents, acaricides, nematicides, fungicides, growth-regulating substances or herbicides. The insecticides include, for example, phosphoric acid esters, carbamates, carboxylic acid esters, chlorinated hydrocarbons, phenylureas, substances produced by microorganisms, and the like.

Particularly favourable mixing partners are, for example, the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxy-phenyl)acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides bronopol, dichlorophen, nitrapyrin, nickel dimethyldithiocarbamate, kasugamycin, octhilinon, furan-carboxylic acid, oxytetracyclin, probenazol, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis,* bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuiran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, rmoxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyraclofos, pyrachlophos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides for example anilides, such as, for example, diflufenican and propanil; arylcarboxylic acids such as, for example, dichloropicolinic acid, dicamba and picloram; aryloxyalkanoic acids, such as, for example, 2,4 D, 2,4 DB, 2,4 DP, fluroxypyr, MCPA, MCPP and triclopyr; aryloxy-phenoxyalkanoic acid esters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlortoluron, diuron, fluometuron, isoproturon, linuron and methabenz-thiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as, for example, mefenacet; sulfonylureas, such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as, for example, butylate, cycloate, di-allate, EPTC, esprocarb, molinate, prosulfocarb, thiobencarb and tri-allate; triazines, such as, for example, atrazine, cyanazine, simazine, simetryn, terbutryn and terbutylazine; triazinones, such as, for example, hexazinone, metamitron and metribuzin; others, such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms, prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are used in a customary manner appropriate for the use form.

When used against hygiene pests and pests of stored products, the active compound is distinguished by an outstanding residual action on wood and clay and by a stability to alkali on limed substrates.

The active compounds according to the invention have an action not only against plant and hygiene pests and pests of stored products, but also in the veterinary medicine sector against animal parasites (ectoparasites), such as hard ticks, soft ticks, mange mites, harvest mites, flies (biting and licking), parasitic fly larvae, lice, hair lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for, example, Trimenopon spp., Menopon spp., Trinoton spp., Bovicola spp., Werneckiella spp., Lepikentron spp., Damalina spp., Trichodectes spp., Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp, Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattrida, for example, *Blatta orientalis, Periplaneta americana, Blattela germanica* and Supella.spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trmbicula spp., Listrophorus spp., Acarus spp. Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they show an outstanding activity against *Boophilus microplus* and *Lucilia cuprina*.

The active compounds of the formula (I) according to the invention are also suitable for combating arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice. By combating these arthropods cases of death and reductions in productivity (for meat, milk, wool, hides, eggs, honey etc) should be diminished, so that more economic animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intramuscular, subcutaneous, intravenous, intraperitoneal etc), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices, etc.

When used for livestock, poultry, pets and the like, the active compounds of the formula (I) can be used as formulations (for example powders, emulsions, compositions capable of flow) which comprise the active compounds in an amount of 1 to 80% by weight, directly or after 100 to 10,000-fold dilution, or they can be used as a chemical bath.

It has furthermore been found that the compounds of the formula I according to the invention display a high insecticidal action against insects which destroy industrial materials.

The following insects may be mentioned as examples and preferred—but without being limited:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus Brunneus, Lyctus africanus, Lyctus planicollis, Lyctus linearis, Lyctus pubescens, Trogoxylon aequale, Minthes rugicollis,* Xyleborus spec., Tryptodendron spec, *Apate monachus, Bostrychus capucins, Heterobostrychus brunneus, Sinoxylon* spec. and *Dinoderus minutus.*

Hymenopterans, such as

*Sirex Juvencus, Urocerus gigas, Urocerus gigas taignus* and *Urocerus augur.*

Termites, such as *Kalotermes flavicollis, Cryptotermes brevis, Heterotermes indicola, Reticulitermes flavipes, Reticulitermes santonensis, Reticuitermes lucifugus, Mastotermes darwiniensis, Zootermopsis nevadensis* and *Coptotermes formosanus.*

Bristle-tails such as Lepisma saccharina.

Industrial materials in the present connection are to be understood as meaning non-living materials, such as, preferably, plastics, adhesives, sizes, papers and cards, leather, wood and processed wood products, and lacquers and paints.

Material to be preserved from insect damage which is quite particularly preferred is wood and processed wood products.

Wood and processed wood products which can be protected by the agents according to the invention or mixtures comprising these are to be understood as meaning, for example: building timber, wooden beams, railway sleepers, bridge components, boat gangplanks, wooden vehicles, crates, pallets, containers, telegraph masts, wood lagging, wooden windows and doors, plywood, chipboards, joinery or wood products used quite generally in house construction or building joinery.

The active compounds can be used as such or in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, water repellant, optionally siccatives and UV stabilizers, and if appropriate dyestuffs and pigments, as well as other processing auxiliaries.

The insecticidal compositions or concentrates used for preservation of wood and derived timber products comprise the active compound according to the invention in a concentration of 0.0001 to 95% by weight, in particular 0.001 to 60% by weight.

The amount of composition or concentrate employed depends on the nature and the occurrence of the insects and on the medium. The optimum amount employed for the use can in each case be determined by a series of tests. In general, however, it is sufficient to employ 0.0001 to 20% by weight, preferably 0.001 to 10% by weight, of the active compound based on the material to be preserved.

The solvent and/or diluent used is an organochemical solvent or solvent mixture and/or an oily or oil-like organochemical solvent or solvent mixture of low volatility and/or a polar organochemical solvent or solvent mixture and/or water and, if appropriate, an emulsifier and/or wetting agent.

Oily or oil-like solvents having an evaporation number above 35 and a flash point above 30° C., preferably above 45° C., are preferably employed as organochemical solvents. Corresponding mineral oils or aromatic fractions thereof or solvent mixtures containing mineral oil, preferably white spirit, petroleum and/or alkylbenzene, are used as such water-insoluble, oily and oil-like solvents of low volatility.

Mineral. oils having a boiling range from 170 to 220° C., white spirit having a boiling range from 170 to 220° C., spindle oil having a boiling range from 250 to 350° C., petroleum or aromatics having a boiling range from 160 to 280° C., terpentine oil and the like are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are employed.

The organic oily or oil-like solvents of low volatility having an evaporation number above 35 and a flash point above 30° C., preferably above 45° C., can be replaced in part by organochemical solvents of high or medium volatility, provided that the solvent mixture likewise has an evaporation number above 35 and. a flash point above 30° C., preferably above 45° C., and that the insecticide/fungicide mixture is soluble or can be emulsified in this solvent mixture.

According to a preferred embodiment, some of the organochemical solvent or solvent mixture is replaced by an aliphatic polar organochemical solvent or solvent mixture. Aliphatic organochemical solvents containing hydroxyl and/or ester and/or ether groups, such as, for example, glycol ethers, esters or the like, are preferably used.

Organochemical binders which are the synthetic resins and/or binding drying oils which are water-dilutable and/or soluble or dispersible or emulsifiable in the organochemical solvents employed and are known per se, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin or silicone resin, drying plant and/or drying oils and/or binders which dry by physical means and are based on a naturally occurring and/or synthetic resin.

The synthetic resin used as the binder can be employed in the form of an emulsion, dispersion or solution. Bitumen or bituminous substances can also be used as binders in an amount of up to 10% by weight. In addition, dyestuffs, pigments, water-repellant agents, odour correctants and inhibitors or corrosion prevention agents and the like which are known per se can be employed.

Preferably, according to the invention, the composition or concentrate comprises at least one alkyd resin or modified alkyd resin and/or one drying plant oil as an organochemical binder. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl)adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether, or ketones, such as benzophenone or ethylenebenzophenone.

Water in particular is also a possible solvent or diluent, if appropriate mixed with one or more of the abovementioned organochemical solvents or diluents, emulsifiers and dispersing agents.

Particularly effective wood preservation is achieved by impregnation processes on a large industrial scale, for example vacuum, a double vacuum or pressure processes.

If appropriate, the ready-to-use compositions can also comprise other insecticides, and if appropriate also one or more fungicides.

Possible additional admixing partners are, preferably, the insecticides and fungicides mentioned in WO 94/29268. The compounds mentioned in this document are an express constituent of the present application.

Especially preferred admixing partners can be insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octylisothiazolin-3-one and 4,5-dichloro-N-octylisothiazolin-3-one.

The preparation and the use of the active compounds according to the invention can be seen from the following examples.

Preparation Examples

EXAMPLE (I-1-a-1)

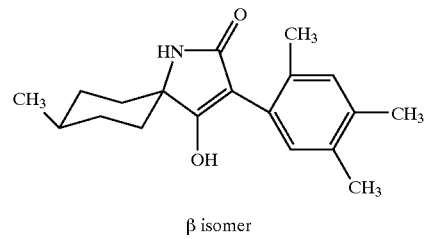

β isomer 25.0 g (0.072 mol) of the compound according to Example (II-2) in 150 ml of anhydrous toluene are added dropwise to 18.5 g (0.165 mol) of potassium tert-butylate in 57 ml of anhydrous tetrahydrofuran (THF) at the reflux temperature and the mixture is stirred under reflux for 1.5 hours. For working up, 220 ml of water are added, the aqueous phase is separated off, the toluene phase is extracted with 110 ml of water and the aqueous phases are combined, washed with toluene and acidified with about 26 ml of concentrated HCl at 10 to 20° C. The product is filtered off with suction, washed, dried and washed by stirring in methyl tert-butyl (MTB) ether/n-hexane.

Yield: 18.0 g (79% of theory), melting point: 159° C.

The following compounds of the formula (I-1-a) are obtained analogously and in accordance with the general information on the preparation:

TABLE 1

(I-1-a)

![Structure I-1-a]

| Example No. | X | Y | Z | A | B | Melting point °C. | Isomer |
|---|---|---|---|---|---|---|---|
| I-1-a-2 | CH₃ | CH₃ | CH₃ | —(CH₂)₂—CHOCH₃—(CH₂)₂— | | >220 | β |
| I-1-a-3 | Cl | Cl | Cl | —(CH₂)₂—CHCH₃—(CH₂)₂— | | >220 | β |
| I-1-a-4 | CH₃ | Cl | CH₃ | —(CH₂)₂—CHCH₃—(CH₂)₂ | | >220 | β |
| I-1-a-5 | CH₃ | CH₃ | CH₃ | —(CH₂)₂—O—(CH₂)₂— | | >220 | |
| I-1-a-6 | CH₃ | Br | Cl | —(CH₂)₂—CHCH₃—(CH₂)₂— | | >220 | β |
| I-1-a-7 | Br | CH₃ | Cl | —(CH₂)₂—CHCH₃—(CH₂)₂— | | 221 | β |
| I-1-a-8 | Cl | —O—CF₂—O— | | —(CH₂)₂—CHCH₃—(CH₂)₂— | | 180 dec. | β |
| I-1-a-9 | Br | —(CH₂)₃— | | —(CH₂)₂—CHCH₃—(CH₂)₂— | | >220 | β |
| I-1-a-10 | Cl | CH₃ | Cl | —(CH₂)₂—CHOCH₃—(CH₂)₂— | | 208 | β |
| I-1-a-11 | Br | CH₃ | CH₃ | —(CH₂)₂—CHCH₃—(CH₂)₂— | | >220 | β |
| I-1-a-12 | CH₃ | Br | CH₃ | —(CH₂)₂—CHCH₃—(CH₂)₂— | | 208 | β |
| I-1-a-13 | Cl | Cl | CH₃ | —(CH₂)₂—CHCH₃—(CH₂)₂— | | 206 | β |
| I-1-a-14 | Cl | Br | CH₃ | —(CH₂)₂—CHCH₃—(CH₂)₂— | | >220 | β |
| I-1-a-15 | Br | CH₃ | CH₃ | —(CH₂)₂—CHCH₃—(CH₂)₂— | | >220 | β |

EXAMPLE (I-1-b-1)

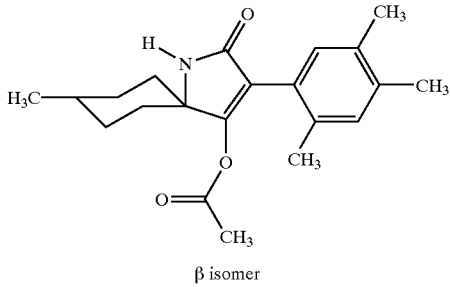

β isomer 1.13 ml (0.015 mol) of acetyl chloride in 5 ml of absolute methylene chloride are added to 4.5 g (0.015 mol) of the compound according to Example (I-1-a-1) and 2.1 ml (15 mmol) of triethylamine in 70 ml of absolute methylene chloride at 0 to 10° C. The mixture is stirred at room temperature until, according to monitoring by thin layer chromatography, the reaction has ended. For working up, the mixture is washed twice with 50 ml of 0.5 N sodium hydroxide solution, dried over magnesium sulphate and evaporated. The crude product is recrystallized from MTB ether/n-hexane.

Yield: 3.4 g (66% of theory), melting point: 209° C.

The following compounds of the formula (I-b-1) are obtained analogously and in accordance with the general information on the preparation:

TABLE 2

(I-1-b)

| Example No. | X | Y | Z | A | B | R¹ | Melting point √ C. | Isomer |
|---|---|---|---|---|---|---|---|---|
| I-1-b-2 | CH₃ | CH₃ | CH₃ | —(CH₂)₂—CHCH₃—(CH₂)₂— | | i-C₃H₇ | 208 | β |
| I-1-b-3 | CH₃ | CH₃ | CH₃ | —(CH₂)₂—CHOCH₃—(CH₂)₂— | | i-C₃H₇ | 152 | β |
| I-1-b-4 | CH₃ | CH₃ | CH₃ | —(CH₂)₂—CHOCH₃—(CH₂)₂— | | i-C₃H₇ | 194 | α* |
| I-1-b-5 | Cl | Cl | Cl | —(CH₂)₂—CHCH₃—(CH₂)₂— | | i-C₃H₇ | >220 | β |
| I-1-b-6 | CH₃ | CH₃ | CH₃ | —(CH₂)₂—O—(CH₂)₂— | | i-C₃H₇ | >220 | — |
| I-1-b-7 | CH₃ | CH₃ | CH₃ | —(CH₂)₂—CHCH₃—(CH₂)₂— | | i-C₃H₇ | 213 | β |

TABLE 2-continued (I-1-b)

| Example No. | X | Y | Z | A B | R[1] | Melting point ° C. | Isomer |
|---|---|---|---|---|---|---|---|
| I-1-b-8 | CH₃ | CH₃ | CH₃ | —(CH₂)₂—CHCH₃—(CH₂)₂— | i-C₄H₉ | 208 | β |
| I-1-b-9 | Cl | Br | CH₃ | —(CH₂)₂—CHCH₃—(CH₂)₂— | i-C₃H₇ | 187 | β |
| I-1-b-10 | Br | CH₃ | CH₃ | —(CH₂)₂—CHCH₃—(CH₂)₂— | i-C₃H₇ | 151 | β |
| I-1-b-11 | Br | CH₃ | Cl | —(CH₂)₂—CHCH₃—(CH₂)₂— | i-C₄H₉ | 217 | β |
| I-1-b-12 | Br | CH₃ | Cl | —(CH₂)₂—CHCH₃—(CH₂)₂— | i-C₃H₇ | 198 | β |
| I-1-b-13 | CH₃ | Br | Cl | —(CH₂)₂—CHCH₃—(CH₂)₂— | i-C₄H₉ | 194 | β |
| I-1-b-14 | CH₃ | Br | Cl | —(CH₂)₂—CHCH₃—(CH₂)₂— | i-C₃H₇ | >220 | β |

EXAMPLE (I-1-c-1)

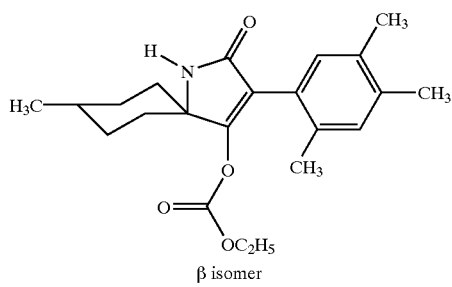

β isomer 1.5 ml (15 mmol) of ethyl chloroformate in 5 ml of absolute methylene chloride are added dropwise to 4.5 g (0.015 mol) of the compound according to Example (I-1-a-1) and 2.1 ml of triethylamine in 70 ml of absolute methylene chloride at 0 to 10° C. and the mixture is stirred at room temperature until, according to monitoring by thin layer chromatography, the reaction has ended. For working up, the mixture is washed twice with 50 ml of 0.5 N sodium hydroxide solution, dried over magnesium sulphate and evaporated.

Yield: 3.3 g (59% of theory), melting point: 193° C.

The following compounds of the formula (I-1-c) are obtained analogously and in accordance with the general information on the preparation:

TABLE 3

(I-1-c)

| Example No. | X | Y | Z | A B | L | M | R[2] | Melting point ° C. | Isomer |
|---|---|---|---|---|---|---|---|---|---|
| I-1-c-2 | CH₃ | CH₃ | CH₃ | —(CH₂)₂—CHOCH₃—(CH₂)₂— | O | O | i-C₄H₉ | 119 | β |
| I-1-c-3 | CH₃ | CH₃ | CH₃ | —(CH₂)₂—CHOCH₃—(CH₂)₂— | O | O | i-C₄H₉ | 207 | α* |
| I-1-c-4 | CH₃ | Br | Cl | —(CH₂)₂—CHCH₃—(CH₂)₂— | O | O | C₂H₅ | >220 | β |
| I-1-c-5 | CH₃ | CH₃ | CH₃ | —(CH₂)₂—O—(CH₂)₂— | O | O | i-C₄H₉ | 205 | — |
| I-1-c-6 | Cl | Cl | Cl | —(CH₂)₂—CHCH₃—(CH₂)₂— | O | O | i-C₄H₉ | 215 | β |
| I-1-c-7 | CH₃ | Cl | CH₃ | —(CH₂)₂—CHCH₃—(CH₂)₂— | O | O | C₂H₅ | 210 | β |
| I-1-c-8 | CH₃ | Cl | CH₃ | —(CH₂)₂—CHCH₃—(CH₂)₂— | O | O | i-C₄H₉ | 214 | β |
| I-1-c-9 | Cl | Br | CH₃ | —(CH₂)₂—CHCH₃—(CH₂)₂— | O | O | C₂H₅ | 223 | β |

*The α isomers were separated off from the isomer mixtures as secondary products by chromatographic separation.

EXAMPLE II-1

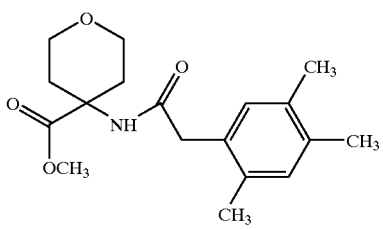

17.5 g of the compound according to Example (XXIX-1) in about 100 ml of methylene chloride are cautiously added dropwise to 30.3 g (0.308 mol) of concentrated sulphuric acid at 30 to 40° C. and the mixture is stirred at this temperature for 2 hours. 41 ml of absolute methanol are then added dropwise such that an internal temperature of about 40° C. is established, and the mixture is stirred at 40 to 70° C. for a further 6 hours.

For working up, the mixture is poured onto 0.29 kg of ice, extracted with methylene chloride, washed with aqueous sodium bicarbonate solution, dried and evaporated. The crude product is purified by column chromatography over silica gel using the mobile phase methylene chloride/ethyl acetate 2:1.

Yield: 13.1 g (67% of theory), melting point: 147° C.

EXAMPLE (II-2)

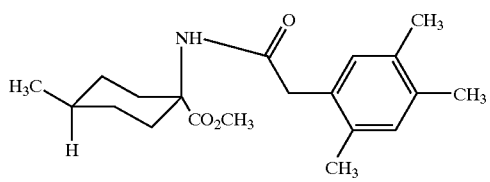

β isomer 40.9 g (0.23 mol) of 2,4,5-trimethylphenylacetic acid and 33.6 ml (0.461 mol) of thionyl chloride are stirred at room temperature for 30 minutes and then at 50° C. until the evolution of gas has ended. Excess thionyl chloride is removed at 50° C. in vacuo. 50 ml of absolute toluene are then added and the mixture is evaporated again. The residue is taken up in 100 ml of absolute THF (solution 1).

Solution 1 is added to 47.9 g of methyl cis-4-methylcyclohexylamine-1-carboxylate and 64.6 ml (0.460 mol) of triethylamine in 600 ml of absolute THF at 0 to 10° C. and the mixture is then stirred at room temperature for 1 hour. It is then filtered with suction, washed with absolute THF and evaporated. The residue is taken up in methylene chloride and the mixture is washed with 0.5 N HCl, dried and evaporated. The crude product is purified by column chromatography over silica gel using methylene chloride/ethyl acetate 7:1.

Yield: 25 g (32% of theory), melting point: 158° C.

The following compounds of the formula (II) are prepared analogously to Examples (11-1) and (11-2) and in accordance with the general information on the preparation.

TABLE 4

(II)

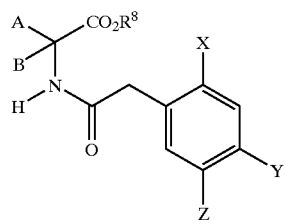

| Example No. | X | Y | Z | A | B | $R^8$ | Melting point ° C. | Isomer |
|---|---|---|---|---|---|---|---|---|
| II-3 | $CH_3$ | $CH_3$ | $CH_3$ | —$(CH_2)_2$—$CHOCH_3$—$(CH_2)_2$— | | $CH_3$ | 161 | β |
| II-4 | $CH_3$ | Cl | $CH_3$ | —$(CH_2)_2$—$CHCH_3$—$(CH_2)_2$— | | $CH_3$ | 192 | β |
| II-5 | Cl | Cl | Cl | —$(CH_2)_2$—$CHCH_3$—$(CH_2)_2$— | | $CH_3$ | 194 | β |
| II-6 | Cl | Br | $CH_3$ | —$(CH_2)_2$—$CHCH_3$—$(CH_2)_2$— | | $CH_3$ | 196 | β |
| II-7 | Cl | CN | $CH_3$ | —$(CH_2)_2$—$CHCH_3$—$(CH_2)_2$— | | $CH_3$ | 163 | β |
| II-8 | Br | Cl | $CH_3$ | —$(CH_2)_2$—$CHCH_3$—$(CH_2)_2$— | | $CH_3$ | 170 | β |
| II-9 | Br | $CH_3$ | $CH_3$ | —$(CH_2)_2$—$CHCH_3$—$(CH_2)_2$— | | $CH_3$ | 158 | β |
| II-10 | $CH_3$ | Br | Cl | —$(CH_2)_2$—$CHCH_3$—$(CH_2)_2$— | | $CH_3$ | 197 | β |
| II-11 | F | Cl | $OCH_3$ | i-$C_3H_7$ | $CH_3$ | $CH_3$ | 109–111 | — |
| II-12 | Cl | —O—$CF_2$—O— | | —$(CH_2)_2$—$CHCH_3$—$(CH_2)_2$— | | $CH_3$ | 164 | β |
| II-13 | Cl | Cl | $CH_3$ | —$(CH_2)_2$—$CHCH_3$—$(CH_2)_2$— | | $CH_3$ | 189 | β |
| II-14 | $CH_3$ | Br | $CH_3$ | —$(CH_2)_2$—$CHCH_3$—$(CH_2)_2$— | | $CH_3$ | 171 | β |
| II-15 | $CH_3$ | Cl | $CH_3$ | —$(CH_2)_2$—$CHOCH_3$—$(CH_2)_2$— | | $CH_3$ | 173 | β |
| II-16 | $CH_3$ | Br | $CH_3$ | —$(CH_2)_2$—$CHOCH_3$—$(CH_2)_2$— | | $CH_3$ | 183 | β |
| II-17 | Br | $CH_3$ | $CH_3$ | —$(CH_2)_2$—$CHOCH_3$—$(CH_2)_2$— | | $CH_3$ | 142 | β |
| II-18 | Cl | Br | $CH_3$ | —$(CH_2)_2$—$CHOCH_3$—$(CH_2)_2$— | | $CH_3$ | | β |
| II-19 | $CH_3$ | $CH_3$ | $CH_3$ | $CH_3$ | $CH_3$ | $CH_3$ | 159 | — |
| II-20 | $CH_3$ | $CH_3$ | $CH_3$ | i-$C_3H_7$ | $CH_3$ | $CH_3$ | | |
| II-21 | Cl | $CH_3$ | Cl | —$(CH_2)_2$—$CHCH_3$—$(CH_2)_2$— | | $CH_3$ | 150 | β |
| II-22 | Br | $CH_3$ | Cl | —$(CH_2)_2$—$CHOCH_3$—$(CH_2)_2$— | | $CH_3$ | | β |
| II-23 | Cl | Cl | F | —$(CH_2)_2$—$CHCH_3$—$(CH_2)_2$— | | $CH_3$ | 171 | β |
| II-24 | Cl | Cl | F | —$(CH_2)_2$—$CHOCH_3$—$(CH_2)_2$— | | $CH_3$ | 182 | β |
| II-25 | Br | —$(CH_2)_3$— | | —$(CH_2)_2$—$CHCH_3$—$(CH_2)_2$— | | $CH_3$ | 168 | β |

EXAMPLE (XXIX-1)

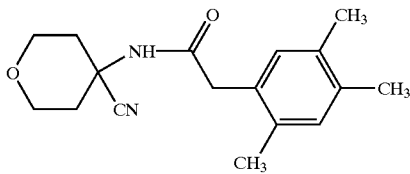

Starting from 17.8 g of 2,4,5-trimethylphenylacetic acid, solution 1 is prepared as in Example (II-2).

Solution 1 is added dropwise to 16.8 g of 1-aminotetrahydropyran-1-carboxylic acid nitrile (70% pure) and 16.8 ml (0.12 mol) of triethylamine in 150 ml of absolute THF at 0 to 10° C. and the mixture is stirred at room temperature for a further hour. It is then evaporated, the residue is taken up in methylene chloride and the mixture is washed with 0.5 N HCl, dried and evaporated. The crude product is recrystallized from MTB ether/n-hexane.

Yield: 17.5 g (61% of theory), melting point: 156° C.

EXAMPLE (I-2-a-1)

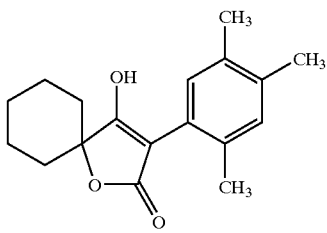

8.42 g (75 mmol) of potassium tert-butylate are initially introduced into 50 ml of dimethylformamide, a solution of 16.6 g (50 mmol) of 1-ethyloxycarbonyl-cyclohexyl 2,4,5-trimethyl-phenylacetate according to Example (III-1) in 50 ml of dimethylformamide is added dropwise at 0 to 10° C. and the mixture is stirred overnight at room temperature.

For working up, the reaction mixture is added dropwise in 500 ml of ice-cold 1 N HCl and the product which has precipitated out is filtered off with suction, washed with water and dried in a vacuum drying cabinet. For further purification, the crude product is boiled up further with n-hexane/acetone.

Yield: 9.2 g (64% of theory) of melting point: 209–212° C.

The following compounds of the formula (I-2-a) are obtained analogously and in accordance with the general information on the preparation:

TABLE 5

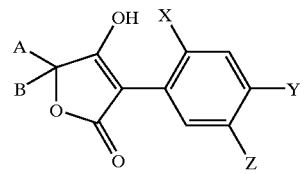

(I-2-a)

| Example No. | X | Y | Z | A | B | Melting point ° C. |
|---|---|---|---|---|---|---|
| I-2-a-2 | CH₃ | CH₃ | CH₃ | —(CH₂)₂—CHCH₃—(CH₂)₂— | | 190–193 |
| I-2-a-3 | CH₃ | CH₃ | CH₃ | —(CH₂)₂—CHOCH₃—(CH₂)₂— | | 167–170 |
| I-2-a-4 | CH₃ | Cl | CH₃ | —(CH₂)₅— | | 241–243 |
| I-2-a-5 | Cl | Cl | Cl | —(CH₂)₅— | | 288 |
| I-2-a-6 | CH₃ | Br | Cl | —(CH₂)₅— | | 242–243 |
| I-2-a-7 | CH₃ | Br | Cl | —(CH₂)₂—CHOCH₃—(CH₂)₂— | | 153–154 |
| I-2-a-8 | Cl | Br | CH₃ | —(CH₂)₅— | | 232–233 |
| I-2-a-9 | Cl | Br | CH₃ | —(CH₂)₂—CHOCH₃—(CH₂)₂— | | 167–177 |
| I-2-a-10 | F | Cl | OCH₃ | CH₃ | CH₃ | 118–120 |
| I-2-a-11 | Cl | —O—CF₂—O— | | —(CH₂)₅— | | 247 |
| I-2-a-12 | Cl | CN | CH₃ | —(CH₂)₅— | | 220–225 |

EXAMPLE (I-2-b-1)

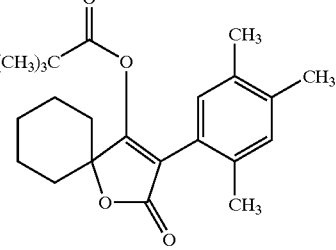

2.86 g (10 mmol) of the compound according to Example I-2-a-1 are initially introduced into 40 ml of methylene chloride, 1.52 g (15 mmol) of triethylamine are added, a solution of 1.57 g (13 mmol) of pivaloyl chloride in 40 ml of methylene chloride is added dropwise, while cooling with ice, and the mixture is subsequently stirred at room temperature for 1 to 2 hours. For working up, the mixture is washed successively with 10% strength citric acid, 1N NaOH and NaCl solution and the organic phase is dried over MgSO₄ and evaporated. For further purification, the crude product is stirred further with a little petroleum ether.

Yield: 3.0 g (81% of theory) of melting point: 128–132° C.

The following compounds of the formula (I-2-b) are obtained analogously and in accordance with the general information on the preparation:

TABLE 6

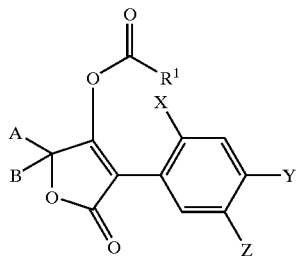

(I-2-b)

| Example No. | X | Y | Z | A | B | R¹ | Melting point °C. |
|---|---|---|---|---|---|---|---|
| I-2-b-2 | CH₃ | CH₃ | CH₃ | —(CH₂)₅— | | i-C₃H₇— | 85–88 |
| I-2-b-3 | CH₃ | CH₃ | CH₃ | —(CH₂)₂—CHCH₃—(CH₂)₂— | | t-C₄H₉— | 139–143 |
| I-2-b-4 | CH₃ | CH₃ | CH₃ | —(CH₂)₂—CHOCH₃—(CH₂)₂— | | i-C₃H₇— | 114–118 |
| I-2-b-5 | CH₃ | CH₃ | CH₃ | —(CH₂)₂—CHOCH₃—(CH₂)₂— | | t-C₄H₉— | 125–129 |
| I-2-b-6 | Cl | Cl | Cl | —(CH₂)₅— | | t-C₄H₉— | 149 |
| I-2-b-7 | Cl | Cl | Cl | —(CH₂)₅— | | t-C₄H₉—CH₂— | 133 |
| I-2-b-8 | CH₃ | Br | Cl | —(CH₂)₅— | | t-C₄H₉—CH₂— | 146–147 |
| I-2-b-9 | CH₃ | Br | Cl | —(CH₂)₅— | | t-C₄H₉— | 168 |
| I-2-b-10 | CH₃ | Br | Cl | —(CH₂)₂—CHOCH₃—(CH₂)₂— | | i-C₃H₇— | 132–133 |
| I-2-b-11 | CH₃ | Br | Cl | —(CH₂)₂—CHOCH₃—(CH₂)₂— | | t-C₄H₉— | 145–149 |
| I-2-b-12 | CH₃ | Cl | CH₃ | —(CH₂)₅— | | t-C₄H₉— | 160 |
| I-2-b-13 | CH₃ | Cl | CH₃ | —(CH₂)₅— | | t-C₄H₉—CH₂— | 157 |
| I-2-b-14 | Cl | Br | CH₃ | —(CH₂)₅— | | t-C₄H₉—CH₂— | 161–162 |
| I-2-b-15 | Cl | Br | CH₃ | —(CH₂)₅— | | t-C₄H₉— | 170 |
| I-2-b-16 | Cl | Br | CH₃ | —(CH₂)₂—CHOCH₃—(CH₂)₂— | | i-C₃H₇— | 98–99 |
| I-2-b-17 | Cl | Br | CH₃ | —(CH₂)₂—CHOCH₃—(CH₂)₂— | | t-C₄H₉— | 139–140 |
| I-2-b-18 | Cl | —O—CF₂—O— | | —(CH₂)₅— | | t-C₄H₉— | 125 |

EXAMPLE (III-1)

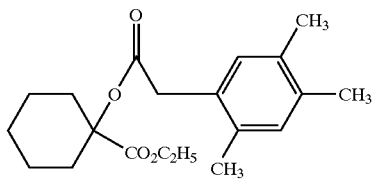

8.9 g (50 mmol) of 2,4,5-trimethyl-phenylacetic acid are initially introduced into 50 ml of toluene, 11.9 g (100 mmol) of thionyl chloride are added and the mixture is stirred at 80° C. until the evolution of hydrogen chloride has ended and is then evaporated. The crude acid chloride is boiled in 50 ml of toluene together with 8.6 g (50 mmol) of ethyl 1-hydroxy-cyclohexanecarboxylate overnight and the mixture is then evaporated.

Yield: 18.6 g (quantitative) of 1-ethoxycarbonyl-cyclohexyl 2,4,6-trimethylphenylacetate as a colourless oil.

The following compounds of the formula (III) are obtained analogously and in accordance with the general instructions for preparation:

TABLE 7

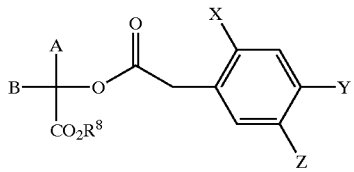

(III)

| Example No. | X | Y | Z | A | B | R⁸ | Melting point °C. |
|---|---|---|---|---|---|---|---|
| III-2 | CH₃ | CH₃ | CH₃ | —(CH₂)₂—CHCH₃—(CH₂)₂— | | C₂H₅ | oil |
| III-3 | CH₃ | CH₃ | CH₃ | —(CH₂)₂—CHOCH₃—(CH₂)₂— | | C₂H₅ | oil |
| III-4 | CH₃ | Cl | CH₃ | —(CH₂)₅— | | C₂H₅ | oil |
| III-5 | Cl | Cl | Cl | —(CH₂)₅— | | C₂H₅ | oil |
| III-6 | CH₃ | Br | Cl | —(CH₂)₅— | | C₂H₅ | oil |
| III-7 | CH₃ | Br | Cl | —(CH₂)₂—CHOCH₃—(CH₂)₂— | | C₂H₅ | oil |
| III-8 | Cl | Br | CH₃ | —(CH₂)₅— | | C₂H₅ | oil |

TABLE 7-continued (III)

| Example No. | X | Y | Z | A | B | R[8] | Melting point °C. |
|---|---|---|---|---|---|---|---|
| III-9 | Cl | Br | $CH_3$ | —$(CH_2)_2$—$CHOCH_3$—$(CH_2)_2$— | | $C_2H_5$ | oil |
| III-10 | F | Cl | $OCH_3$ | $CH_3$ | $CH_3$ | $C_2H_5$ | oil |
| III-11 | Cl | —O—$CF_2$—O— | | | —$(CH_2)_5$— | $C_2H_5$ | oil |
| III-12 | Cl | CN | $CH_3$ | —$(CH_2)_5$— | | $C_2H_5$ | oil |

EXAMPLE (I-3-a-1)

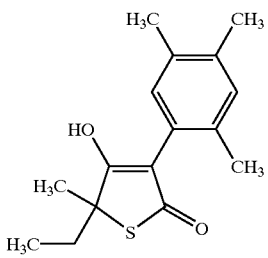

26.0 g (60.7 mmol) of the compound according to Example (IV-1) are heated under reflux with 55 ml of trifluoroacetic acid in 110 ml of toluene for 3 hours. Excess trifluoroacetic acid is removed in vacuo, 400 ml of water and 120 ml of MTB ether are added to the residue and the pH is brought to 14 with NaOH. The mixture is extracted twice with MTB ether and the aqueous phase is acidified with concentrated HCl and extracted 3 times with MTB ether. The organic phases are dried and concentrated. Yield 8.8 g (52% of theory), melting point 160 to 162° C.

EXAMPLE (I-3-b-1)

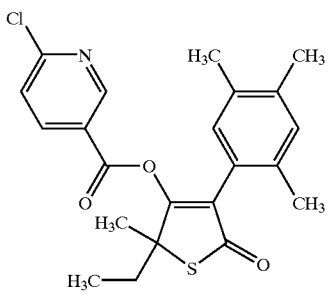

1.0 g (3.6 mmol) of the compound according to Example I-3-a-1 are initially introduced into 15 ml of absolute methylene chloride, and 0.75 ml of triethylamine is added. A solution of 0.82 g (4.68 mmol) of 6-chloronicotinyl chloride in 3 ml of absolute methylene chloride is added dropwise, while cooling with ice. The mixture is stirred at room temperature for 2 hours. It is washed twice with 10% strength citric acid and the combined aqueous phases are extracted with methylene chloride. The combined organic phases are washed twice with 1 N NaOH and the aqueous alkaline phases are extracted with methylene chloride. Finally, the combined organic phases are dried and concentrated and the residue is stirred with petroleum ether. Yield 1.37 g (91% of theory), melting point 123 to 126° C.

The compounds of the formula I-3-b listed in the following table were prepared analogously to Example I-3-b-1 and in accordance with the general description.

I-3-b

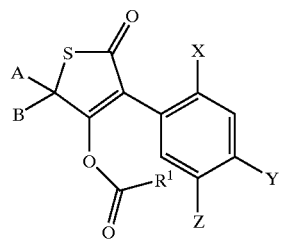

| Example No. | X | Y | Z | A | B | R[1] | Melting point °C. |
|---|---|---|---|---|---|---|---|
| I-3-b-2 | $CH_3$ | $CH_3$ | $CH_3$ | $C_2H_5$ | $CH_3$ | $t$-$C_4H_9$ | oil |
| I-3-b-3 | $CH_3$ | $CH_3$ | $CH_3$ | $C_2H_5$ | $CH_3$ | Cyclopropyl | oil |
| I-3-b-4 | $CH_3$ | $CH_3$ | $CH_3$ | $C_2H_5$ | $CH_3$ | Cl—$CH_2$—$C(CH_3)_2$ | oil |

EXAMPLE (I-3-c-1)

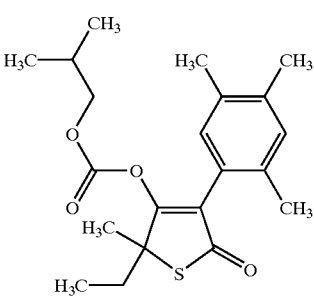

Preparation 1.0 g (3.6 mmol) of the compound according to Example I-3-a-1 are initially introduced into 15 ml of absolute methylene chloride, and 0.75 ml (1.5 equivalents) of triethylamine is added. A solution of 0.61 ml (0.64 g; 4.68 mmol) of isobutyl 6-chloroformate in 3 ml of absolute methylene chloride is a added dropwise, while cooling with ice. The mixture is stirred at room temperature for 2 hours. It is washed twice with 10% strength citric acid and the combined aqueous phases are extracted with methylene chloride. The combined organic phases are washed twice with 1 N NaOH and the aqueous alkaline phases are extracted with methylene chloride. Finally, the combined organic phases are dried and concentrated.

Yield 1.32 g (97% of theory), oil $^1$H-NMR (400 MHz, DMSO):

δ=0.60–0.70 m, 6H, CH(C$\underline{H}_3$)$_2$
1.00–1.05 m, 3H, CH$_2$C$\underline{H}_3$
1.50–1.60 m, 1H, C$\underline{H}$(CH$_3$)$_2$
1.70–1.76 d, 3H, C(C$\underline{H}_3$)
1.90–2.02 m, 2H, C$\underline{H}_2$CH$_3$
2.05–2.20 m, 9H, ArC$\underline{H}_3$
3.65–3.72 m, 2H, OC$\underline{H}_2$
6.75–6.80 d, 1H, ortho Ar—$\underline{H}$
7.01 s, 1H, meta Ar—$\underline{H}$

EXAMPLE (I-3-c-2)

The compound of the formula (I-3-c-2) was obtained analogously to Example (I-3-c-1) as an oil:

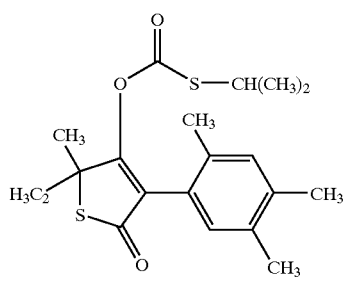

(I-3-c-2)

EXAMPLE (IV-1)

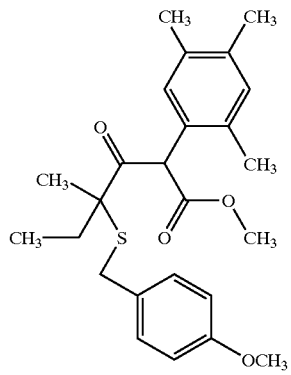

A: 25 g (98 mmol) of the compound of the formula (XXXII-1)

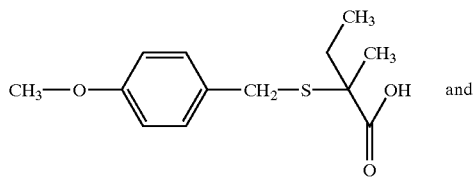

(XXXII-1)

1 drop of dimethylformamide are stirred with 17.5 g (147 mmol) of thionyl chloride in 100 ml of toluene at room temperature for 5 minutes and then at 100° C. until the evolution of gas has ended. Volatile constituents are removed under a high vacuum.

B: 72 ml (118 mmol) of butyllithium (1.6 M) are added dropwise to 18 ml (130 mmol) of diisopropylamine in 100 ml of THF, while cooling with ice, and the mixture is stirred at this temperature for a further 15 minutes. 18.8 g (108 mmol) of the compound according to Example (XXIV-3), dissolved in 40 ml of THF, are then added dropwise at 0° C. and the mixture is stirred at this temperature for 30 minutes. The acid chloride prepared according to A, dissolved in 40 ml of TBF, is then added dropwise at 0° C. and the mixture is stirred at room temperature for 1 hour. 350 ml of MTB ether and a few drops of water are then added and the mixture is extracted twice with 10% strength ammonium chloride solution, dried and concentrated. The crude product (40 g) is purified by column chromatography (mobile phase cyclohexane/ethyl acetate 10/1). Yield 27.0 g (64% of theory), oil.

$^1$H-NMR (CDCl$_3$, 400 MHz):

δ=0.80–0.95 m, 3H, CH$_2$C$\underline{H}_3$
1.42 s, 3H, C—C$\underline{H}_3$
1.65–2.05 m, 2H, C$\underline{H}_2$CH$_3$
2.15–2.35 m, 9H, ArC$\underline{H}_3$
3.10–3.45 m, 2H, SC$\underline{H}_2$
3.70–3.80 m, 6H, OC$\underline{H}_3$
6.70–7.30 m, 6H, Ar—$\underline{H}$

EXAMPLE (I-4-a-1)

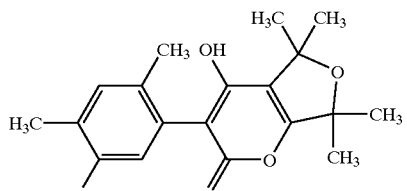

6.7 g (30 mmol) of 2-(2,4,5-trimethylphenyl)-chlorocarbonylketene are heated at 200° C. with 4.3 g (30 mmol) of 4,5-dihydro-2,2,5,5-tetramethyl-3-(2H)-furanone for 4 hours. After column chromatography over silica gel using toluene/ethanol 20:1 as the mobile phase, 4.6 g (Δ46% of theory) of melting point: 182–184° C. are obtained.

The following compounds of the formula (I-4-a) are obtained analogously and in accordance with the general information on the preparation:

TABLE 8

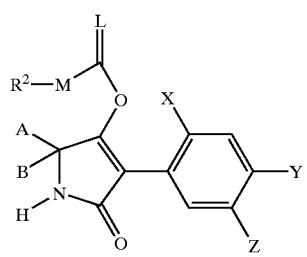

(I-4-a)

| Example No. | X | Y | Z | A | D | Melting point ° C. |
|---|---|---|---|---|---|---|
| I-4-a-2 | CH₃ | CH₃ | CH₃ | —CO—(CH₂)₃— | | 134–137 |
| I-4-a-3 | CH₃ | CH₃ | CH₃ | CH₃ | 4-F-Phenyl | 216–218 |
| I-4-a-4 | CH₃ | CH₃ | CH₃ | CH₃ | 2-Pyridyl | 130–132 |
| I-4-a-5 | CH₃ | CH₃ | CH₃ | CH₃ | | 65–68 |
| I-4-a-6 | CH₃ | CH₃ | CH₃ | CH₃ | 4-Cl-Phenyl— | 192–194 |

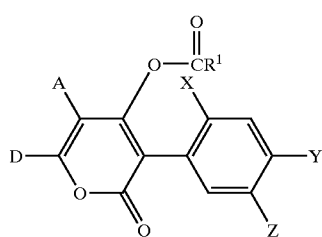

EXAMPLE (I-4-b-1)

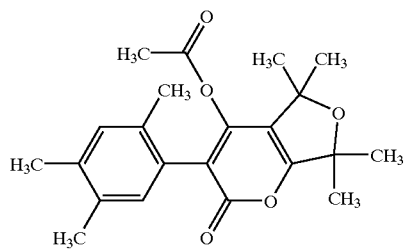

2.5 g (7.5 mmol) of the compound (I-4-a-1) are initially introduced into 25 ml of ethyl acetate, 0.75 g of triethylamine is added, and 0.6 g of acetyl chloride in 20 ml of ethyl acetate is added dropwise at 0° C. The mixture is stirred at room temperature for 20 hours, the precipitate is separated off and the product is washed twice with 50 ml of half-concentrated sodium chloride solution, dried over sodium sulphate and evaporated in vacuo. The residue is chromatographed over silica gel using toluene/acetone 50:1.

Yield: 0.8 g (Δ m29% of theory) of melting point: 143–144° C.

The compounds of the formula I-4-b listed in the following table were prepared analogously to Example I-4-b-1 and in accordance with the general information on the preparation:

TABLE 9

(I-4-b)

| Example No. | X | Y | Z | A | D | R¹ | Melting point: [° C.] σ ¹H-NMR (CDCl₃): δ [ppm] |
|---|---|---|---|---|---|---|---|
| I-4-b-2 | CH₃ | CH₃ | CH₃ | CH₃ | 4-F-Phenyl | CH₃ | 141–143 |
| I-4-b-3 | CH₃ | CH₃ | CH₃ | CH₃ | 2-Pyridyl | CH₃ | 135–136 |
| I-4-b-4 | CH₃ | CH₃ | CH₃ | CH₃ | 2-Pyridyl | C(CH₃)—(CH₂OCH₃)₂ | 8.68(1H, d), 7.98 (1H, d), 7.80(1H, t), 2.33(3H, s), 2.23 (3H, s), 2.20(3H, s), 2.15(3H, s) |
| I-4-b-5 | CH₃ | CH₃ | CH₃ | CH₃ | cyclopentyl | CH₃ | 137–139 |

EXAMPLE (I-4-c-1)

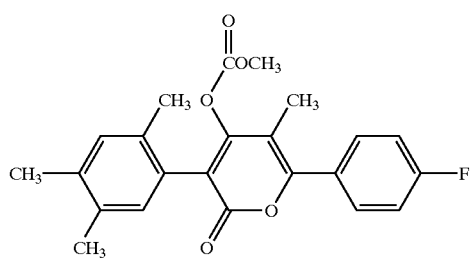

1.7 g (5 mmol) of the compound (I-a-3) are initially introduced into 20 ml of ethyl acetate, 0.5 g (5 mmol) of triethylamine is added, and 0.5 g (5 mmol) of methyl chloroformate in 5 ml of ethyl acetate is added dropwise at 0° C. The mixture is stirred at room temperature for 20 hours, the precipitate is separated off and the product is washed twice with 50 ml of half-concentrated sodium chloride solution, dried over sodium sulphate and evaporated in vacuo. The residue is chromatographed over silica gel using toluene/acetone 30/1. Yield 1.0 g (51% of theory) of melting point 144 to 146° C.

The following compounds of the formula (I-4-c) are obtained analogously and in accordance with the general information on the preparation:

EXAMPLE (XXIII-1)

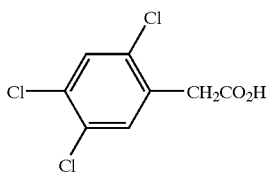

247 g (1.162 mol) of the compound according to Example (XXIV-1) (75% pure) are added dropwise to a mixture of 100 g (1.785 mol) of KOH in 130 ml of water and 260 ml of methanol at room temperature and the mixture is heated under reflux for 5 hours. After cooling, it is diluted with 300 ml of water and extracted with ethyl acetate. The aqueous phase is acidified with half-concentrated hydrochloric acid and the precipitate is filtered off with suction and dried.

Yield: 77 g (45% of theory), melting point: 119–121° C.

EXAMPLE (XXIII-2)

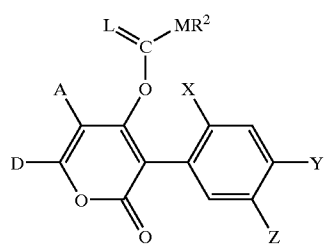

TABLE 10

(I-4-c)

| Example No. | X | Y | Z | A | D | R² | L | M | Melting point ° C. |
|---|---|---|---|---|---|---|---|---|---|
| I-4-c-2 | $CH_3$ | $CH_3$ | $CH_3$ | $CH_3$ | 2-Pyridyl | $CH_3$ | O | O | 160–162 |
| I-4-c-3 | $CH_3$ | $CH_3$ | $CH_3$ | $CH_3$ | 2-Pyridyl | $CH(CH_3)-C_2H_5$ | O | O | 107–109 |

EXAMPLE (I-5-a-1)

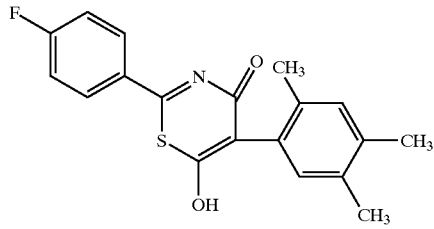

2.2 g (10 mmol) of 2-(2,4,5-trimethylphenyl)-chlorocarbonylketene are heated at 50° C. with 1.6 g (10 mmol) of 4-fluorothiobenzamide in 80 ml of toluene for 6 hours. The precipitate is separated off, washed with cyclohexane and dried. 2.8 g (82% of theory) of melting point 215 to 216° C. are obtained.

2,4,5-Trichloro-phenylacetic acid, melting point: 112–115° C., is obtained analogously to Example (XXIII-1).

Preparation of 2,4,5-trimethyl-phenylacetic acid

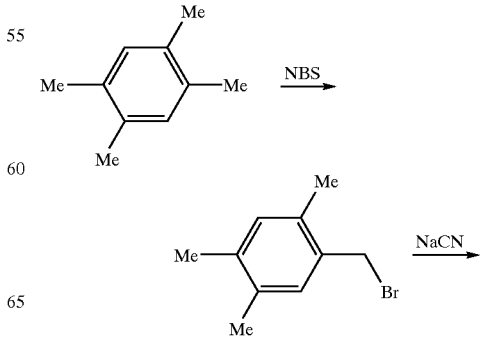

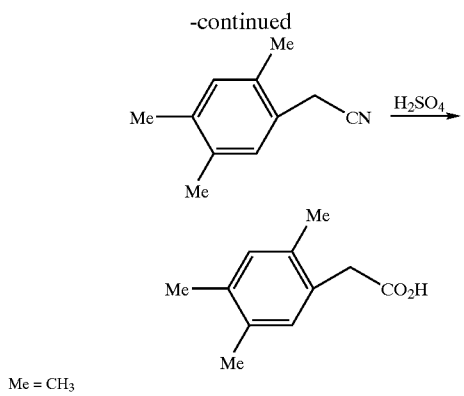

Me = CH$_3$

EXAMPLE (XXIII-3)

286 g (1.4 mol) of 66% pure 1,2,4,5-tetramethylbenzene are dissolved in 563 ml of carbon tetrachloride, and 27.5 g (0.15 mol) of N-bromosuccinimide and 0.4 g of benzoyl chloride are introduced in succession at room temperature. The mixture is heated to 80° C. and 248 g (1.39 mol) of N-bromosuccinimide are added in portions. Thereafter, the mixture is subsequently stirred at 80° C. for a further 30 minutes and is then cooled to room temperature. The solid is filtered off with suction and the solvent is stripped off under 20 mbar via a solids bridge. The residue is then distilled under a high vacuum and 226 g (66% of theory) of 2,4,5-trimethylbenzyl bromide having a boiling point of 95° C. under 0.05 mbar and a purity of 86% are obtained.

A solution of 226 g (0.91 mol) of 2,4,5-trimethyl-benzyl bromide (86% pure) in 94 ml of toluene is added dropwise to a solution of 57 g (1.16 mol) of sodium cyanide in 63 ml of water and 0.6 g of Aliquat 336 at 60 to 80° C., and the mixture is then subsequently stirred at 80° C. for 4 hours. After cooling to room temperature, the phases are separated and the organic phase is washed twice with water and twice with saturated NaCl solution, dried and concentrated. After distillation, 103 g (70%) of 2,4,5-trimethyl-benzyl cyanide having a purity of 99% and a boiling point of 120° C. under 0.2 mbar are obtained.

2118 ml of concentrated sulphuric acid are added dropwise to 2662 ml of water at room temperature and the solution is heated to 90° C. 355 g (2.23 mol) of 2,4,5-trimethyl-benzyl cyanide are metered into the half-concentrated sulphuric acid at this temperature and the mixture is subsequently stirred at 100° C. for 8 hours. After cooling, the reaction mixture is poured into ice-water, while stirring vigorously, and filtered with suction. The solid is washed several times with water and then with petroleum ether and dried. 358 g (90% of theory) of 2,4,5-trimethylphenylacetic acid having a melting point of 123–125° C. are obtained.

The novel phenyl acetic acids of formula (XXIII) listed in the following Table 11 were prepared analogously to Examples (XXIII-1) and (XXIII-3) and in accordance with the general information on the preparation:

TABLE 11

(XXIII)

| Example No. | X | Y | Z | melting point ° C. |
|---|---|---|---|---|
| XXIII-4 | Cl | Br | CH$_3$ | 118–120 |
| XXIII-5 | Cl | CN | CH$_3$ | 164–169 |
| XXIII-6 | Br | CH$_3$ | Cl | 123–125 |
| XXIII-7 | Br | CH$_3$ | CH$_3$ | 122 |
| XXIII-8 | CH$_3$ | Br | Cl | 148–150 |
| XXIII-9 | F | Cl | OCH$_3$ | |
| XXIII-10 | Cl | —O—CF$_2$—O— | | 115–119 |
| XXIII-11 | Cl | Cl | CH$_3$ | 101 |
| XXIII-12 | CH$_3$ | Br | CH$_3$ | 141 |
| XXIII-13 | Cl | CH$_3$ | Cl | 112 |
| XXIII-14 | Br | —(CH$_2$)$_3$— | | 143 |
| XXIII-15 | Cl | Cl | F | 118 |

The compounds of formula (XXIII) are novel excepted the compounds in which X, Y, Z=CH$_3$ and in which X, Y, Z=Cl.

EXAMPLE (XXIV-3)

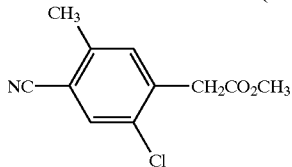

35 g (0.143 mol) of methyl 2-chloro-4-bromo-5-methylphenylacetate and 31 g of CuCN are heated under reflux in 350 ml of dimethylformamide for 1 day. The solvent is stripped of under vacuum, the residue is portitioned between water and tert butyl-methylether, the organic phase is dried and evaporated.

Yield: 18 g.

The novel phenyl acetic acid esters of formula (XXXIV) listed in Table 12 were prepared analogously to Example (XXXIV).

TABLE 12

(XXIV)

| Example No. | X | Y | Z | physic. constant |
|---|---|---|---|---|
| XXIV-4 | Cl | Br | CH$_3$ | mp.: 41–43° C. |
| XXIV-5 | Br | CH$_3$ | Cl | mp.: 37–38° C. |
| XXIV-6 | Br | CH$_3$ | CH$_3$ | Kp$_{0.03\text{mbar}}$ 89–91° C. |
| XXIV-7 | CH$_3$ | Br | Cl | Kp$_{0.07\text{mbar}}$ 107–110° C. |
| XXIV-8 | Cl | —O—CF$_2$—O— | | oil |
| XXIV-9 | Cl | Cl | CH$_3$ | Kp$_{0.4\text{mbar}}$ 89–91° C. |
| XXIV-10 | CH$_3$ | Br | CH$_3$ | Kp$_{0.03\text{mbar}}$ 96–98° C. |
| XXIV-11 | Br | —(CH$_2$)$_3$— | | Kp$_{0.2\text{mbar}}$ 130–135° C. |

The compounds of formula (XXIV) are novel except the compound in which X, Y, Z=CH$_3$ and in which X, Y, Z=Cl.

EXAMPLE (XXIV-1)

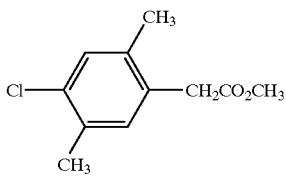

700 ml of a 30% strength methanolic solution of sodium methylate are added dropwise to a solution of 347 g (0.948 mol) of the compound according to Example (XXV-1) (74.3% pure) in 410 ml of methanol at room temperature, the mixture is heated under reflux for 5 hours and cooled to room temperature and 110 ml of concentrated sulphuric acid are added dropwise. The mixture is boiled under reflux for 1 hour, the methanol is distilled off and the solid residue is taken up in water. The organic phase is separated off and the aqueous phase is extracted twice with 1.5 l of methylene chloride. The combined organic phases are dried over $Na_2SO_4$ and concentrated.

Yield: 247 g of a dark oil Δ 92% of theory having a content of 75% (gas chromatography).

EXAMPLE (XXIV-2)

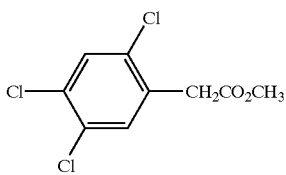

Methyl 2,4,5-trichloro-phenylacetate is obtained analogously to Example (XXIV-1) as a dark oil in a yield of 95% of theory and a purity of 80% (gas chromatography).

EXAMPLE (XXV-1)

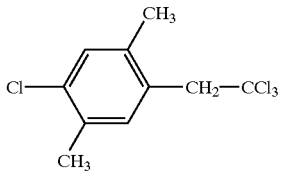

2205 g (22.7 mol) of 1,1-dichloroethene are added dropwise to a thoroughly cooled mixture of 229.7 g (2.272 mol) of tert-butyl nitrite and 254.8 g (1.775 mol) of anhydrous copper(II) chloride in 990 ml of anhydrous acetonitrile, the mixture being kept at below 30° C. A mixture of 232 g (1.49 mol) of 4-chloro-2,5-dimethylaniline and 1500 ml of anhydrous acetonitrile is then added dropwise at a temperature of below 30° C. The mixture is stirred at room temperature until the evolution of gas has ended and is then poured cautiously into 6 l of 20% strength HCl and extracted several times with a total of 6 l of methyl tert-butyl ether (MTBE). The combined organic phases are washed with 20% strength HCl, dried and concentrated. The oil which remains is rectified.

Yield: 347 g of dark oil Δ 63% of theory having, a content of 74% (gas chromatography).

EXAMPLE (XXV-2)

2-(2,4,5-Trichlorophenyl)-1,1,1-trichloroethane was obtained analogously to Example (XXV-1) in the form of a dark oil in a yield of 81% of theory with a content of 78%.

The 1,1,1-trichloro-2-phenyl-ethanes of formula (XXV) listed in Table 13 were prepared analogously to Example (XXV-1):

TABLE 13

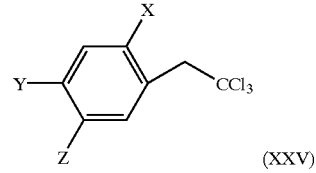

(XXV)

| Example No. | X | Y | Z | physic. constant |
|---|---|---|---|---|
| XXV-3 | Cl | Br | $CH_3$ | mp.: 82–84° C. |
| XXV-4 | Br | $CH_3$ | Cl | oil* |
| XXV-5 | Br | $CH_3$ | $CH_3$ | oil* |
| XXV-6 | $CH_3$ | Br | Cl | oil* |
| XXV-7 | Cl | —O—$CF_2$—O— | | oil* |
| XXV-8 | Cl | Cl | $CH_3$ | mp.: 70–72° C. |
| XXV-9 | $CH_3$ | Br | $CH_3$ | oil* |
| XXV-10 | Br | —$(CH_2)_3$— | | oil |

The oils were used without further purification for the preparation of the compounds of formula (XXIV). The compounds of formula (XXV) are novel except the compound in which X, Y, Z=Cl.

Synthesis of 2,4,5-trimethylphenylcarbonylketene

Methyl 2,4,5-trimethylphenylacetate

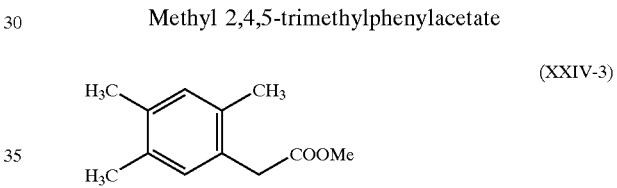

(XXIV-3)

100 g (0.56 mol) of 2,4,5-trimethylphenylacetic acid were dissolved in 230 ml of methanol, 6 ml of concentrated hydrochloric acid were added and the mixture was heated under reflux for 10 hours. It was then cooled to room temperature and the methanol was removed in vacuo. The residue was stirred into a solution of 53 g of sodium carbonate, dissolved in 260 ml of water, and the organic phase was taken up in 200 ml of toluene. The organic phase was separated off, dried and concentrated and the residue was distilled. 48.6 g of methyl 2,4,5-trimethylphenylacetate having a boiling point of 86° C. under 0.2 mbar were obtained.

Dimethyl 2-(2,4,5-trimethylpentyl)-malonate

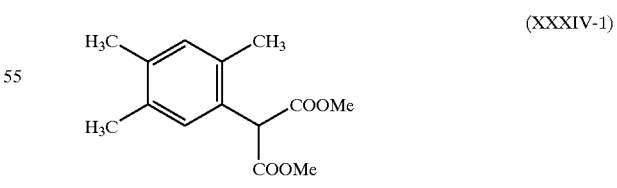

(XXXIV-1)

18.6 g (0.62 mol, 80% pure) of sodium hydride were initially introduced into 384 ml of dimethyl carbonate and the mixture was heated to about 80° C. 48 g (0.25 mol) of methyl 2,4,5-trimethylphenylacetate, dissolved in 100 ml of dimethyl carbonate, were then added dropwise and the mixture was heated under reflux for 4 hours. It was cooled to room temperature, the excess sodium hydride was destroyed with ethanol and the mixture was then poured into 1500 ml of ice-water. A pH of 4 to 5 was established with 6 N hydrochloric acid and the organic phase was taken up in toluene. The organic phase was separated off, dried and concentrated and the residue was employed in the next stage without further purification. 51.6 g of dimethyl 2-(2,4,5-trimethylphenyl)-malonate were obtained as an oil.

$^1$H-NMR (CDCl$_3$): δ=7.12 (s, 1H); 6.98 (s, 1H); 4.84 (s, 1H); 3.75 (s, 6H); 2.27 (s, 3H); 2.23 (s, 3H); 2.21 ppm (s, 3H).

2-(2,4,5-Trimethylphenyl)-malonic acid

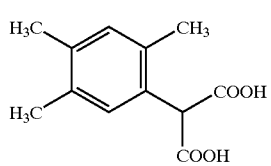

(XXXIII-1)

51.6 g (0.21 mol) of dimethyl 2-(2,4,5-trimethylphenyl)-malonate were added dropwise to a mixture of 180 ml of methanol and 38.1 g (0.68 mol) of potassium hydroxide, dissolved in 92 ml of water, at room temperature. The mixture was then heated under reflux for 5 hours and then cooled to room temperature again and concentrated.

The residue was stirred into ice-water and the mixture was washed with a little toluene. The aqueous solution was acidified to a pH of 1 with concentrated hydrochloric acid, while cooling with ice, and the precipitate was filtered off with suction and dried. 30.3 g of 2-(2,4,5-trimethylphenyl)-malonic acid were obtained.

$^1$H-NMR (d$_6$-DMSO): δ=7.03 (s, 1H); 6.95 (s, 1H); 4.66 (s, 1H); 2.17 (s, 3H); 2.16 ppm (s, 6H).

2,4,5-Trimethylphenylchlorocarbonyl ketene

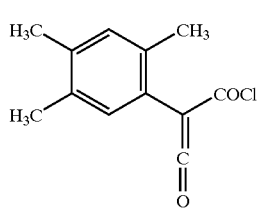

(VI-1)

30 g of 2-(2,4,5-trimethylphenyl)-malonic acid were suspended in 60 ml of toluene at 50 to 60° C. and 62.5 ml of thionyl chloride were added dropwise. The mixture was then heated at 90 to 100° C. for 15 hours. It was then cooled, the volatile constituents were driven off with an inert gas and the excess thionyl chloride was distilled off. 30.6 g of 2,4,5-trimethylphenylchlorocarbonyl ketene were isolated as the residue.

$^1$H-NMR (CDCl$_3$) δ=7.07 (s, 2H), 2.27 (s, 3H); 2.22 (s, 3H); 2.21 ppm (s, 3H).

Use Examples

Example A

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test, for example, the compounds according to Preparation Examples I-4-b-1 and I-a-4 caused a destruction of 100% after 7 days at an active concentration of, for example, 0.1%.

Example B

Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified periods of time, the destruction in % is determined. 100% means that all the caterpillars have been killed; 0% means that none of the caterpillars have been killed.

In this test, for example, the compounds according to Preparation Examples I-1-a-1, I-1-b-2, I-1-c-1, I-4-a-3, I-4-a-1, I-4-b-1 and I-4-a-4 caused a destruction of 100% after 7 days at an active compound concentration of, for example, 0.1%.

Example C

Spodoptera Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*) while the leaves are still moist.

After the specified periods of time, the destruction in % is determined. 100% means that all the caterpillars have been killed; 0% means that none of the caterpillars have been killed.

In this test, for example, the compounds according to Preparation Examples I-1-a-1, I-1-2, I-4-a-3, I-4-a-1, I-4-b-1 and I-4-a-4 caused a destruction of 100% after 7 days at an active compound concentration of, for example, 0.1%.

Example D

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with caterpillars of the rice green leafhopper (*Nephotettix cincticeps*) while the seedlings are still moist.

After the specified periods of time, the destruction in % is determined. 100% means that all the caterpillars have been killed; 0% means that none of the caterpillars have been killed.

In this test, for example, the compounds according to Preparation Examples I2-a-2, I2-a-3, I2-b-4, I-2-b-5, I-1-a-1, I-1-b-2, I-1-c-1, I1-b-1, I1-b-3. I1-c-2, I-1-c-3, I-4-a-3 and I-4-a-4 caused a destruction of 100% after 6 days at an active compound concentration of, for example, 0.1%.

Example E

Myzus Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested by the peach aphid (*Myzus persicae*) are treated by being dipped into the preparation of the active compound of the desired concentration.

After the specified periods of time, the destruction in % is determined. 100% means that all the caterpillars have been killed; 0% means that none of the caterpillars have been killed.

In this test, for example, the compounds according to Preparation Examples 1-2-a-1, I-2-b-4, I-1-b-2, I-1-b-3, I-1-c-2 and I-4-a-4 caused a destruction of 100% after 6 days at an active compound concentration of, for example, 0.1%.

Example F

Tetranychus Test (OP-resistant/Dipping Treatment)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested by the two-spotted spider mite (*Tetranychus urticae*) are treated by being dipped into the preparation of the active compound of the desired concentration.

After the specified periods of time, the destruction in % is determined. 100% means that all the caterpillars have been killed; 0% means that none of the caterpillars have been killed.

In this test, for example, the compounds according to Preparation Examples 1-2-b-2, I-2-b-1, I-1-b-2 and I-4-b-1 caused a destruction of at least 98% after 13 days at an active compound concentration of, for example, 0.1%.

Example G

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive.

After three weeks, the degree of damage to the plants is rated in % damage in comparison to the development of the untreated control.

The figures denote:

0%=no action (like untreated control)

100%=total destruction

In this test, for example, the compound according to Preparation Example I-4-a-3 caused damage of 90% to *Alopecurus myosuroids*, 9.6% to *Avena fatua* and 95% to *Setaria viridis* when applied in an amount of, for example, 500 g/ha, coupled with good tolerance by *Beta vulgaris*.

Example H

Test with Fly Larvae/Development-inhibiting Action

Test animals: All larval stages of *Lucilia cuprina* (OP-resistant)

[pupae and adults (without contact with the active compound)]

Solvent:
  35 parts by weight of ethylene glycol monomethyl ether
  35 parts by weight of nonylphenol polyglycol ether To produce a suitable formulation, 3 parts by weight of active compound are mixed with seven parts of the above-mentioned solvent/emulsifier mixture and the emulsion concentrate thus obtained is diluted with water to the particular desired concentration.

30 to 50 larvae per concentration are introduced onto horse-meat (1 cm$^3$), in glass tubes, onto which 500 µl of the dilution to be tested are pipetted. The glass tubes are placed in plastic beakers, the base of which is covered with beach sand, and are stored in a climatically controlled room (26° C.±1.5° C., 70% relative humidity ±10%). The action is checked after 24 hours and 48 hours (larvicidal action). After emergence of the larvae (about 72 hours), the glass tubes are removed and perforated plastic lids are placed on the beakers. After 1½ times the development period (hatching of the control flies), the flies which have hatched and the pupae/pupae cases are counted.

The criterion for the action is the onset of death among the treated larvae after 48 hours (larvicidal effect) or the inhibition of hatching of adults from the pupae or the inhibition of pupae formation. The criterion for the in vitro action of a substance is the inhibition of flea development or a halt in development before the adult stage. 100% larvicidal action means that all the larvae have died after 48 hours. 100% development-inhibiting action means that no adult flies have hatched.

In this test, for example, the compound according to Preparation Example I-4-a-1 caused an action of 100% at an active compound concentration of, for example, 1000 ppm.

Example I

Test with Boophilus Microplus Resistant/SP-resistant Parkhurst Strain

Test animals: Adult satiated females

Solvent: Dimethyl sulphoxide 20 mg of active compound are dissolved in 1 ml of dimethyl sulphoxide, and lower concentrations are prepared by dilution in the same solvent.

The test is carried out as a 5-fold determination. 1 μl of the solutions is injected into the abdomen and the animals are transferred to dishes and kept in a climatically controlled room. The action is determined via the inhibition of oviposition. 100% means that no tick has laid.

In this test, for example, the compounds according to Preparation Examples I-4-a-1 and I-4-b-1 had an action of 100% at an active compound concentration of, for example, 20 μg per animal.

What is claimed is:

1. A compound of the formula (I)

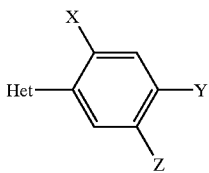

(I)

in which

X represents halogen, $C_1-C_6$-alkyl, $C_2-C_6$-alkenyl, $C_2-C_6$-alkinyl, $C_1-C_6$-alkoxy, $C_1-C_4$-halogenoalkyl, $C_1-C_4$-halogenoalkoxy, cyano or nitro, Y represents hydrogen, halogen, $C_1-C_6$-alkyl, $C_1-C_6$-alkoxy, $C_1-C_4$-halogenoalkyl, $C_1-C_4$-halogenoalkoxy, cyano or nitro, Z represents halogen, $C_1-C_6$-alkyl, $C_1-C_6$-alkoxy, $C_1-C_4$-halogenoalkyl, $C_1-C_4$-halogenoalkoxy, hydroxyl, cyano, nitro, or phenoxy, phenylthio, thiazolyloxy, pyridinyloxy, pyrimidinyloxy, pyrazolyloxy, phenyl-$C_1-C_4$-alkoxy or phenyl-$C_1-C_4$-alkylthio which are in each case optionally substituted by halogen, $C_1-C_4$-alkyl, $C_1-C_4$-alkoxy, $C_1-C_4$-halogenoalkyl, $C_1-C_4$-halogenoalkoxy, nitro or cyano, Het represents

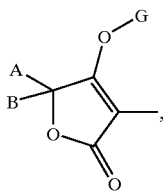

(2)

A represents hydrogen, or represents $C_1-C_{12}$-alkyl, $C_2-C_8$-alkenyl, $C_1-C_{10}$-alkoxy-$C_1-C_8$-alkyl, poly-$C_1-C_8$-alkoxy-$C_1-C_8$-alkyl or $C_1-C_{10}$-alkylthio-$C_1-C_6$-alkyl which are in each case optionally substituted by halogen, or represents $C_3-C_8$-cycloalkyl which is optionally substituted by halogen, $C_1-C_6$-alkyl or $C_1-C_6$-alkoxy and in which one or two methylene groups are optionally replaced by oxygen and/or sulphur, or represents phenyl, naphthyl, phenyl-$C_1-C_6$-alkyl, naphthyl-$C_1-C_6$-alkyl or hetaryl having 5 to 6 ring atoms and one to three heteroatoms from the series consisting of oxygen, sulphur and nitrogen, which are in each case optionally substituted by halogen, $C_1-C_6$-alkyl, $C_1-C_6$-halogenoalkyl, $C_1-C_6$-alkoxy, $C_1-C_6$-halogenoalkoxy, cyano or nitro, B represents hydrogen, $C_1-C_{12}$-alkyl or $C_1-C_8$-alkoxy-$C_1-C_6$-alkyl, G represents hydrogen (a), or represents one of the groups

(b)

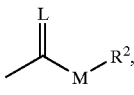

(c)

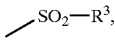

(d)

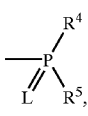

(e)

E, or (f)

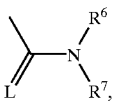

(g)

wherein

E represents one metal ion equivalent or an ammonium ion,

L represents oxygen or sulphur,

M represents oxygen or sulphur, $R^1$ represents $C_1-C_{20}$-alkyl, $C_2-C_{20}$-alkenyl, $C_1-C_8$-alkoxy-$C_1-C_8$-alkyl, $C_1-C_8$-alkylthio-$C_1-C_8$-alkyl or poly-$C_1-C_8$-alkoxy-$C_1-C_8$-alkyl which are in each case optionally substituted by halogen, or represents $C_3-C_8$-cycloalkyl which is optionally substituted by halogen, $C_1-C_6$-alkyl or $C_1-C_6$-alkoxy and in which one or two methylene groups are optionally replaced by oxygen and/or sulphur, or represents phenyl which is optionally substituted by halogen, cyano, nitro, $C_1-C_6$-alkyl, $C_1-C_6$-alkoxy, $C_1-C_6$-halogenoalkyl, $C_1-C_6$-halogenoalkoxy, $C_1-C_6$-alkylthio or $C_1-C_6$-alkylsulphonyl, or represents phenyl-$C_1-C_6$-alkyl which is optionally substituted by halogen, nitro, cyano, $C_1-C_6$-alkyl, $C_1-C_6$-alkoxy, $C_1-C_6$-halogenoalkyl or $C_1-C_6$-halogenoxalkoxy, or represents 5- or 6- membered hetaryl having one or two heteroatoms from the series consisting of oxygen, sulphur and nitrogen which is optionally substituted by halogen or $C_1-C_6$-alkyl or represents phenoxy-$C_1-C_6$-alkyl which is optionally substituted by halogen or $C_1-C_6$-alkyl or represents 5- or 6-membered hetaryloxy-$C_1-C_6$-alkyl which has one or two heteroatoms from the series consisting of oxygen, sulphur and nitrogen and is optionally substituted by halogen, amino or $C_1-C_6$-alkyl, $R^2$ represents $C_1-C_{20}$-alkyl, $C_2-C_{20}$-alkenyl, $C_1-C_8$-alkoxy-$C_2-C_8$-alkyl or poly-$C_1-C_8$-alkoxy-$C_2-C_8$-alkyl which are in each case optionally substituted by halogen, or represents $C_3-C_8$-cycloalkyl which is optionally substituted by halogen, $C_1-C_6$-alkyl or $C_1-C_6$-alkoxy, or represents phenyl or benzyl which are in each case optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy, $R^3$ represents $C_1$–$C_8$-alkyl which is optionally substituted by halogen, or phenyl or benzyl which are in each case optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ and $R^5$ independently of one another represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio which are in each case optionally substituted by halogen, or represent phenyl, phenoxy or phenylthio which are in each case optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another represent hydrogen, or represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl which are in each case optionally substituted by halogen, or represent phenyl or benzyl which are in each case optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical which is optionally substituted by $C_1$–$C_6$-alkyl and in which one methylene group is optionally replaced by oxygen or sulphur.

2. A compound of the formula (I) according to claim 1, in which

X represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Y represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Z represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxy, cyano or nitro, or phenoxy or benzyloxy which are in each case optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, Het represent

(2)

A represents hydrogen, or represents $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl which are in each case optionally substituted by fluorine or chlorine, or represents $C_3$–$C_7$-cycloalkyl which is optionally substituted by fluorine or chlorine, $C_1$–$C_4$-alkyl or $C_1$–$C_4$-alkoxy and in which one or two methylene groups are optionally replaced by oxygen and/or sulphur, or represents phenyl, furanyl, pyridyl, imidazolyl, triazolyl, pyrazolyl, indolyl, thiazolyl, thienyl or phenyl-$C_1$–$C_4$-alkyl which are in each case optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, B represents hydrogen, $C_1$–$C_{10}$-alkyl or $C_1$–$C_6$-alkoxy-$C_1$–$C_4$-alkyl, G represents hydrogen (a), or represents one of the groups

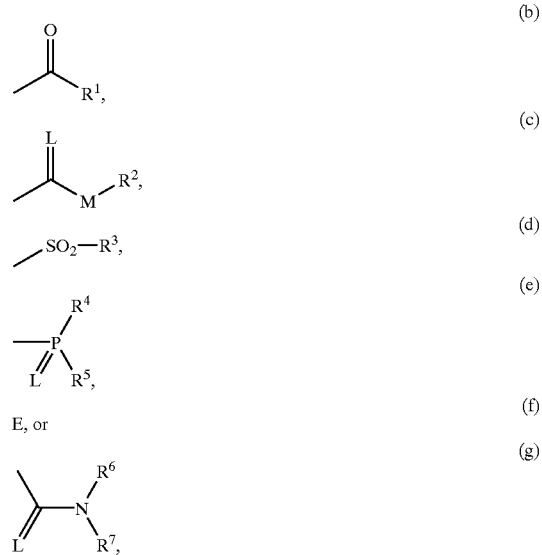

wherein

E represents one metal ion equivalent or an ammonium ion,

L represents oxygen or sulphur,

M represents oxygen or sulphur, $R^1$ represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl which are in each case optionally substituted by fluorine or chlorine, or represents $C_3$–$C_7$-cycloalkyl which is optionally substituted by fluorine, chlorine, $C_1$–$C_5$-alkyl or $C_1$–$C_5$-alkoxy and in which one or two methylene groups are optionally replaced by oxygen and/or sulphur, or represents phenyl which is optionally substituted by fluorine, chlorine, bromine, cyano, nitro, $C_1$–$C_4$-alkyl, $C_1$–$C_4$-alkoxy, $C_1$–$C_4$-halogenoalkyl, $C_1$–$C_4$-halogenoalkoxy, $C_1$–$C_4$-alkylthio or $C_1$–$C_4$-alkylsulphonyl, or represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_4$-halogenoalkyl or $C_1$–$C_4$-halogenoxalkoxy, or represents pyrazolyl, thiazolyl, pyridyl, pyrimidyl, furanyl or thienyl which are in each case optionally substituted by fluorine, chlorine, bromine or $C_1$–$C_4$-alkyl, or represents phenoxy-$C_1$–$C_5$-alkyl which is optionally substituted by fluorine, chlorine, bromine or $C_1$–$C_4$-alkyl or represents pyridyloxy-$C_1$–$C_5$-alkyl, pyrimidyloxy-$C_1$–$C_5$-alkyl or thiazolyloxy-$C_1$–$C_5$-alkyl which are in each case optionally substituted by fluorine, chlorine, bromine, amino or $C_1$–$C_4$-alkyl, $R^2$ represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy- C₂–C₆-alkyl which are in each case optionally substituted by fluorine or chlorine, or represents C₃–C₇-cycloalkyl which is optionally substituted by fluorine, chlorine, C₁–C₄-alkyl or C₁–C₄-alkoxy, or represents phenyl or benzyl which are in each case optionally substituted by fluorine, chlorine, bromine, cyano, nitro, C₁–C₄-alkyl, C₁–C₃-alkoxy, C₁–C₃-halogenoalkyl or C₁–C₃-halogenoalkoxy, R³ represents C₁–C₆-alkyl which is optionally substituted by fluorine or chlorine, or phenyl or benzyl which are in each case optionally substituted by fluorine, chlorine, bromine, C₁–C₄-alkyl, C₁–C₄-alkoxy, C₁–C₂-halogenoalkyl, C₁–C₂-halogenoalkoxy, cyano or nitro, R⁴ and R⁵ independently of one another represent C₁–C₆-alkyl, C₁–C₆-alkoxy, C₁–C₆-alkylamino, di-(C₁–C₆-alkyl)amino, C₁–C₆-alkylthio or C₃–C₄-alkenylthio which are in each case optionally substituted by fluorine or chlorine, or represent phenyl, phenoxy or phenylthio which are in each case optionally substituted by fluorine, chlorine, bromine, nitro, cyano, C₁–C₃-alkoxy, C₁–C₃-halogenoalkoxy, C₁–C₃-alkylthio, C₁–C₃-halogenoalkylthio, C₁–C₃-alkyl or C₁–C₃-halogenoalkyl, R⁶ and R⁷ independently of one another represent hydrogen, or represent C₁–C₆-alkyl, C₃–C₆-cycloalkyl, C₁–C₆-alkoxy, C₃–C₆-alkenyl or C₁–C₆-alkoxy-C₂–C₆-alkyl which are in each case optionally substituted by fluorine or chlorine, or represent phenyl or benzyl which are in each case optionally substituted by fluorine, chlorine, bromine, C₁–C₅-alkyl, C₁–C₅-halogenoalkyl or C₁–C₅-alkoxy, or together represent a C₃–C₆-alkylene radical which is optionally substituted by C₁–C₄-alkyl and in which one methylene group is optionally replaced by oxygen or sulphur.

3. A compound of the formula (I) according to claim 1, in which

X represents fluorine, chlorine, bromine, methyl, ethyl, propyl, butyl, iso-butyl, iso-propyl, tert-butyl, methoxy, ethoxy, propoxy, iso-propoxy, trifluoromethyl, trifluoromethoxy, difluoromethoxy, cyano or nitro, Y represents hydrogen, fluorine, chlorine, bromine, methyl, ethyl, propyl, iso-propyl, butyl, iso-butyl, tert-butyl, methoxy, ethoxy, propoxy, iso-propoxy, trifluoromethyl, trifluoromethoxy, difluoromethoxy, cyano or nitro, Z represents fluorine, chlroine, bromine, methyl, ethyl, propyl, butyl, iso-butyl, iso-propyl, tert-butyl, methoxy, ethoxy, propoxy, iso-propoxy, trifluoromethyl, trifluoromethoxy, difluoromethoxy, cyano or nitro, Het represents

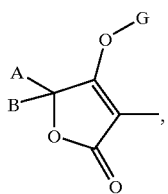
(2)

A represents hydrogen, or represents C₁–C₈-alkyl, C₂–C₄-alkenyl, C₁–C₆-alkoxy-C₁–C₄-alkyl, poly-C₁–C₄-alkoxy-C₁–C₄-alkyl or C₁–C₆-alkylthio-C₁–C₄-alkyl which are in each case optionally substituted by fluorine or chlorine, or represents C₃–C₆-cycloalkyl which is optionally substituted by fluorine, chlorine, methyl or methoxy and in which one or two methylene groups are optionally replaced by oxygen and/or sulphur, or represents phenyl, pyridyl, or benzyl which are in each case optionally substituted by fluorine, chlorine, bromine, methyl, ethyl, n-propyl, iso-propyl, methoxy, ethoxy, trifluoromethyl, trifluoromethoxy, cyano or nitro, B represents hydrogen, C₁–C₈-alkyl or C₁–C₄-alkoxy-C₁–C₂-alkyl, G represents hydrogen (a), or represents one of the groups

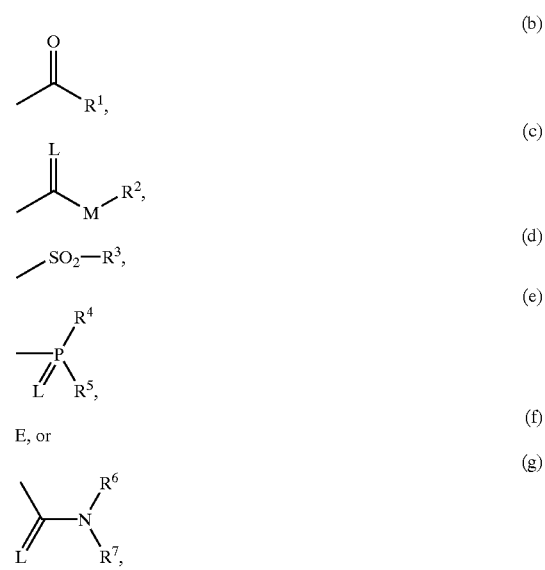

wherein

E represents one metal ion equivalent or an ammonium ion,

L represents oxygen or sulphur,

M represents oxygen or sulphur,

R¹ represents C₁–C₁₄-alkyl, C₂–C₁₄-alkenyl, C₁–C₄-alkoxy-C₁–C₄-alkyl, C₁–C₆-alkylthio-C₁–C₄-alkyl or poly-C₁–C₄-alkoxy-C₁–C₆-alkyl which are in each case optionally substituted by fluorine or chlorine, or represents C₃–C₆-cycloalkyl which is optionally substituted by fluorine, chlorine, methyl, ethyl, n-propyl, i-propyl, n-butyl, i-butyl, tert-butyl, methoxy, ethoxy, n-propoxy, iso-propoxy and in which one or two methylene groups are optionally replaced by oxygen and/or sulphur, or represents phenyl which is optionally substituted by fluorine, chlorine, bromine, cyano, nitro, methyl, ethyl, n-propyl, i-propyl, methoxy, ethoxy, trifluoromethyl, trifluoromethoxy, methylthio, ethylthio, methylsulphonyl or ethylsulfonyl, or represents benzyl which is optionally substituted by fluorine, chlorine, bromine, methyl, ethyl, n-propyl, i-propyl, methoxy, ethoxy, trifluoromethyl or trifluoromethoxy, or represents furanyl, thienyl or pyridyl which are in each case optionally substituted by fluorine, chlorine, bromine, methyl or ethyl, or represents phenoxy-$C_1$–$C_4$-alkyl which is optionally substituted by fluorine, chlorine, bromine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl which are in each case optionally substituted by fluorine, chlorine, bromine, amino, methyl or ethyl, $R^2$ represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl which are in each case optionally substituted by fluorine or chlorine, or represents $C_3$–$C_6$-cycloalkyl which is optionally substituted by fluorine, chlorine, methyl, ethyl, n-propyl, iso-propyl or methoxy, or represents phenyl or benzyl which are in each case optionally substituted by fluorine, chlorine, bromine, cyano, nitro, methyl, ethyl, n-propyl, i-propyl, methoxy, ethoxy, trifluoromethyl or trifluormethoxy, $R^3$ represents methyl, ethyl, propyl, iso-propyl, butyl or tert-butyl which is optionally substituted by fluorine or chlorine, or phenyl or benzyl which are in each case optionally substituted by fluorine, chlorine, bromine, methyl, ethyl, iso-propyl, tert-butyl, methoxy, ethoxy, iso-propoxy, trifluoromethyl, trifluormethoxy, cyano or nitro, $R^4$ and $R^5$ independently of one another represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio which are in each case optionally substituted by fluorine or chlorine, or represent phenyl, phenoxy or phenylthio which are in each case optionally substituted by fluorine, chlorine, bromine, nitro, cyano, methyl, methoxy, trifluoromethyl or trifluoromethoxy, $R^6$ and $R^7$ independently of one another represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl which are in each case optionally substituted by fluorine or chlorine, or represent phenyl or benzyl which are in each case optionally substituted by fluorine, chlorine, bromine, methyl, methoxy or trifluoromethyl, or together represent a $C_5$–$C_6$-alkylene radical which is optionally substituted by methyl or ethyl and in which one methylene group is optionally replaced by oxygen or sulphur.

4. A process for the preparation of a compound of the formula (I) according to claim 1, wherein to obtain (B) a compound of the formula (I-2-a)

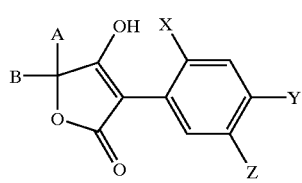

(I-2-a)

in which
A, B, X, Y and Z have the abovementioned meanings, a compound formula (III)

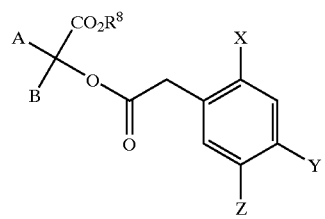

(III)

in which
A, B, X, Y, Z and $R^8$ have the abovementioned meanings,
are subjected to intramolecular condensation in the presence of a diluent and in the presence of a base,
and, optionally the compounds of formula (I-2-a) are then
(F)α) reacted with an acid halide of the formula (VIII)

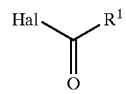

(VIII)

in which
$R^1$ has the meaning given in claim 2 and
Hal represents halogen, or
β) reacted with a carboxylic acid anhydride of the formula (IX)

$R^1$—CO—O—CO—$R^1$ (IX)

in which
$R^1$ has the abovementioned meaning,
optionally in the presence of a diluent and optionally in the presence of an acid-binding agent, or
(G) reacted with chloroformic acid esters or chloroformic acid thioesters of the formula (X)

$R^2$—M—CO—Cl (X)

in which
$R^2$ and M have the meanings given in claim 2,
optionally in the presence of a diluent and optionally in the presence of an acid-binding agent, or
(H)α) reacted with a chloromonothioformic acid ester or chlorothioformic acid ester of the formula (XI)

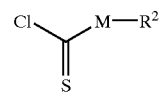

(XI)

in which
M and $R^2$ have the abovementioned meanings, optionally in the presence of a diluent and optionally in the presence of an acid-binding agent, or
β) reacted with carbon disulphide and then with compounds of the formula (XII)

$R^2$—Hal (XII)

in which
$R^2$ has the abovementioned meaning and
Hal represents chlorine, bromine or iodine, optionally in the presence of a diluent and optionally in the presence of a base, or (I) reacted with sulphonic acid chlorides of the formula (XIII)

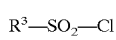         (XIII)

in which
R$^3$ has the meaning given in claim 2,
optionally in the presence of a diluent and optionally in the presence of an acid-binding base, or (J) reacted with phosphorus compounds of the formula (XIV)

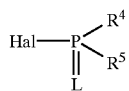         (XIV)

in which
L, R$^4$ and R$^5$ have the abovementioned meanings and
Hal represents halogen,
optionally in the presence of a diluent and in the presence of an acid-binding base, or (K) reacted with a metal compound or amine of the formula (XV) or (XVI)

         (XV)

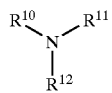         (XVI)

in which
Me represents a mono- or divalent metal,
t represents the number 1 or 2 and
R$^{10}$, R$^{11}$ and R$^{12}$ independently of one another represent hydrogen or alkyl,
optionally in the presence of a diluent, or (L)α) reacted with isocyanoates or isothiocyanates of the formula (XVII)

         (XVII)

in which
R$^6$ and L have the meanings given in claim 2,
optionally in the presence of a diluent and optionally in the presence of a catalyst, or β) reacted with carbamic acid chlorides or thiocarbamic acid chlorides of the formula (XVIII)

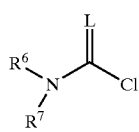         (XVIII)

in which
L, R$^6$ and R$^7$ have the abovementioned meanings,
optionally in the presence of a diluent and optionally in the presence of an acid-binding agent.

5. Process for the preparation of pest compositions and herbicides, characterized in that compounds of the formula (I) according to claim 1 are mixed with extenders and/or surface-active agents.

6. A pesticidal or herbicidal composition comprising a pesticidally or herbicidally effective amount of a compound according to claim 1 and an extender.

7. A method of combatting unwanted pests or vegetation which comprises administering to such pests or vegetation or to a locus from which it is desired to exclude such pests or vegetation a pesticidally or herbicidally effective amount of a compound according to claim 1.

* * * * *

UNITED STATES PATENT AND TRADEMARK OFFICE
CERTIFICATE OF CORRECTION

PATENT NO.    : 6,511,942 B1
DATED         : January 28, 2003
INVENTOR(S)   : Folker Lieb, et al.

It is certified that error appears in the above-identified patent and that said Letters Patent is hereby corrected as shown below:

Column 99,
Line 51, delete, "chlroine" and substitute -- chlorine --

Signed and Sealed this

Tenth Day of June, 2003

JAMES E. ROGAN
*Director of the United States Patent and Trademark Office*